(12) United States Patent
Zhang et al.

(10) Patent No.: US 10,414,718 B2
(45) Date of Patent: Sep. 17, 2019

(54) DEZOCINE ANALOGUE

(71) Applicant: SHANDONG DANHONG PHARMACEUTICAL CO., LTD., Shandong (CN)

(72) Inventors: Yang Zhang, Shanghai (CN); Wentao Wu, Shanghai (CN); Zhixiang Li, Shanghai (CN); Guangwen Yang, Shanghai (CN); Yongbo Fang, Shanghai (CN); Tao Zhang, Shanghai (CN); Wei Gu, Shanghai (CN); Shuhui Chen, Shanghai (CN); Fei Wang, Shanghai (CN); Jian Li, Shanghai (CN)

(73) Assignee: Shandong Danhong Pharmaceutical Co., Ltd., Shandong (CN)

(*) Notice: Subject to any disclaimer, the term of this patent is extended or adjusted under 35 U.S.C. 154(b) by 0 days.

(21) Appl. No.: 16/066,852

(22) PCT Filed: Jan. 4, 2017

(86) PCT No.: PCT/CN2017/070126
§ 371 (c)(1),
(2) Date: Jun. 28, 2018

(87) PCT Pub. No.: WO2017/118375
PCT Pub. Date: Jul. 13, 2017

(65) Prior Publication Data
US 2019/0010114 A1    Jan. 10, 2019

(30) Foreign Application Priority Data
Jan. 4, 2016 (CN) .......................... 2016 1 0003868

(51) Int. Cl.
| C07C 215/64 | (2006.01) |
| C07D 313/20 | (2006.01) |
| C07C 255/59 | (2006.01) |
| C07C 217/74 | (2006.01) |
| C07C 219/26 | (2006.01) |

(52) U.S. Cl.
CPC .......... *C07C 215/64* (2013.01); *C07C 217/74* (2013.01); *C07C 219/26* (2013.01); *C07C 255/59* (2013.01); *C07D 313/20* (2013.01); *C07C 2601/02* (2017.05); *C07C 2601/14* (2017.05); *C07C 2603/80* (2017.05)

(58) Field of Classification Search
CPC .. C07D 313/20; C07D 337/06; C07D 225/06; C07C 215/64
See application file for complete search history.

(56) References Cited

U.S. PATENT DOCUMENTS

| 3,836,670 A | * | 9/1974 | Freed | .................... | A61K 31/137 |
| | | | | | 514/546 |
| 3,869,512 A | * | 3/1975 | Freed | .................... | C07C 49/755 |
| | | | | | 560/107 |
| 3,931,328 A | * | 1/1976 | Freed | .................... | C07C 49/747 |
| | | | | | 568/326 |
| 3,937,736 A | * | 2/1976 | Freed | .................... | C07C 49/697 |
| | | | | | 568/327 |
| 3,957,872 A | * | 5/1976 | Freed | .................... | C07C 49/675 |
| | | | | | 564/299 |

(Continued)

FOREIGN PATENT DOCUMENTS

| CN | 102503840 A | 6/2012 | |
| GB | 1363658 A | * 8/1974 | ............. C07C 45/68 |

(Continued)

OTHER PUBLICATIONS

M. Freed et al., 16 Journal of Medicinal Chemistry, 595-599 (1973) (Year: 1973).*
M. Freed et al., 19 Journal of Medicinal Chemistry, 476-480 (1976) (Year: 1976).*
M. Freed et al., 19 Journal of Medicinal Chemistry, 560-562 (1976) (Year: 1976).*
Priority Application CN201610003868.6 (Withdrawn before publication) dated Apr. 8, 2016.
Maehr, J. Chem. Ed., vol. 62, pp. 114-120, 1985.
Remington, The Science and Practice of Pharmacy, 21st Ed., Lippincott, Williams & Wilkins, 2005.

(Continued)

*Primary Examiner* — Alexander R Pagano
(74) *Attorney, Agent, or Firm* — Harness, Dickey & Pierce, P.L.C.

(57) ABSTRACT

Disclosed in the present disclosure is a Dezocine analog, and particularly disclosed are compounds represented by formula (I), (II) and (III), a pharmaceutically acceptable salt or tautomer thereof.

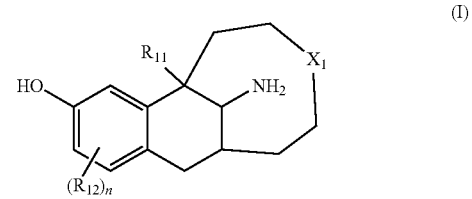

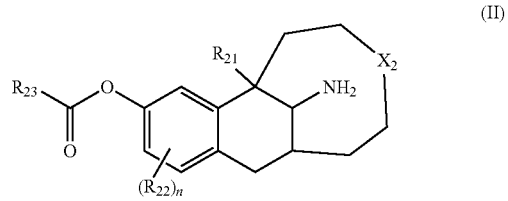

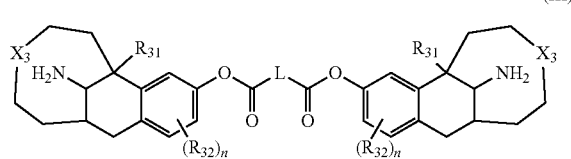

14 Claims, No Drawings

(56) References Cited

U.S. PATENT DOCUMENTS

| | | | | | |
|---|---|---|---|---|---|
| 3,976,693 | A | * | 8/1976 | Freed | .................... C07C 251/44 564/265 |
| 3,976,696 | A | * | 8/1976 | Freed | .................... C07C 215/70 564/427 |
| 3,979,434 | A | * | 9/1976 | Freed | ........................... 560/124 |
| 4,001,326 | A | * | 1/1977 | Freed | .................... C07C 49/675 560/124 |
| 4,001,331 | A | * | 1/1977 | Freed | .................... C07C 49/675 549/416 |
| 4,034,041 | A | | 7/1977 | Freed et al. | |
| 4,049,701 | A | * | 9/1977 | Freed | ........................... 560/103 |

FOREIGN PATENT DOCUMENTS

| | | | |
|---|---|---|---|
| JP | S57-47176 | B1 | 10/1982 |
| WO | WO-2019007285 | A1 * | 1/2019 |

OTHER PUBLICATIONS

Berge et al., "Pharmaceutical Salts", Journal of Pharmaceutical Science, vol. 66, pp. 1-19, 1977.
International Search report of PCT/CN2017/070126 dated Apr. 11, 2017.
Written Opinion dated May 25, 2018 of PCT/CN2017/070126.
Partial European Search Report issued in related EP Application No. 17735813.2 dated Nov. 7, 2018.
Meier E. Freed et al, "Bridged aminotetralins. 4. resolution of potent analgesics of the bridged aminotetralin type", Journal of Medicinal Chemistry, 1976, vol. 19, No. 4, pp. 560-562.
Meier E. Freed et al, "Bridged aminotetralins as novel potent analgesic substances", Journal of Medicinal Chemistry, 1973, vol. 16, No. 6, pp. 595-599.
Notification of Reasons for Refusals and Search Report issued in Japanese patent application No. 2018-553293 dated May 28, 2019.

* cited by examiner

DEZOCINE ANALOGUE

CROSS-REFERENCE TO RELATED APPLICATIONS

This application is a National Stage of International Application No. PCT/CN2017/070126, filed on Jan. 4, 2017, and published in Chinese as WO2017/118375 A1 on Jul. 13, 2017. This application claims the priority to Chinese Patent Application No. 201610003868.6, filed on Jan. 4, 2016. The entire disclosures of the above applications are incorporated herein by reference.

FIELD

Disclosed in the present disclosure is a Dezocine analogue, and particularly disclosed are compounds represented by formula (I), (II) and (III), a pharmaceutically acceptable salt or tautomer thereof.

BACKGROUND

This section provides background information related to the present disclosure which is not necessarily prior art.

Dezocine, the chemical name of which is (−)-[5R-(5α,11α,13S*)]-13-amino-5,6,7,8,9,10,11,12-octahydro-5-methyl-5,11-methan obenzocyclodecen-3-ol, is a typical opioid alkaloid analgesic developed by the Swedish company Astra. This type of drugs work by agonizing the opioid receptor. The analgesic effect of Dezocine is stronger than Pentazocine and Dezocine is not only a κ receptor agonist but also a μ antagonist. Dezocine is less addictive and is suitable for the treatment of moderate to severe pain after surgery, visceral colic, and pain of terminal cancer patients. With favourable tolerability and safety, Dezocine is expected to become an opioid alkaloid analgesic with good market prospects.

The structure of Dezocine is as follows:

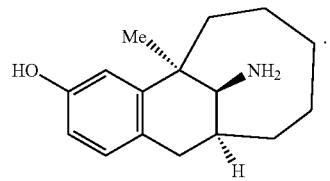 [SMILES: C[C@@]12CCCCC[C@@H](Cc3ccc(O)cc31)[C@@H]2N]

SUMMARY

This section provides a general summary of the disclosure, and is not a comprehensive disclosure of its full scope or all of its features.

The present disclosure provides a compound represented by formula (I), (II) and (III), a pharmaceutically acceptable salt or a tautomer thereof

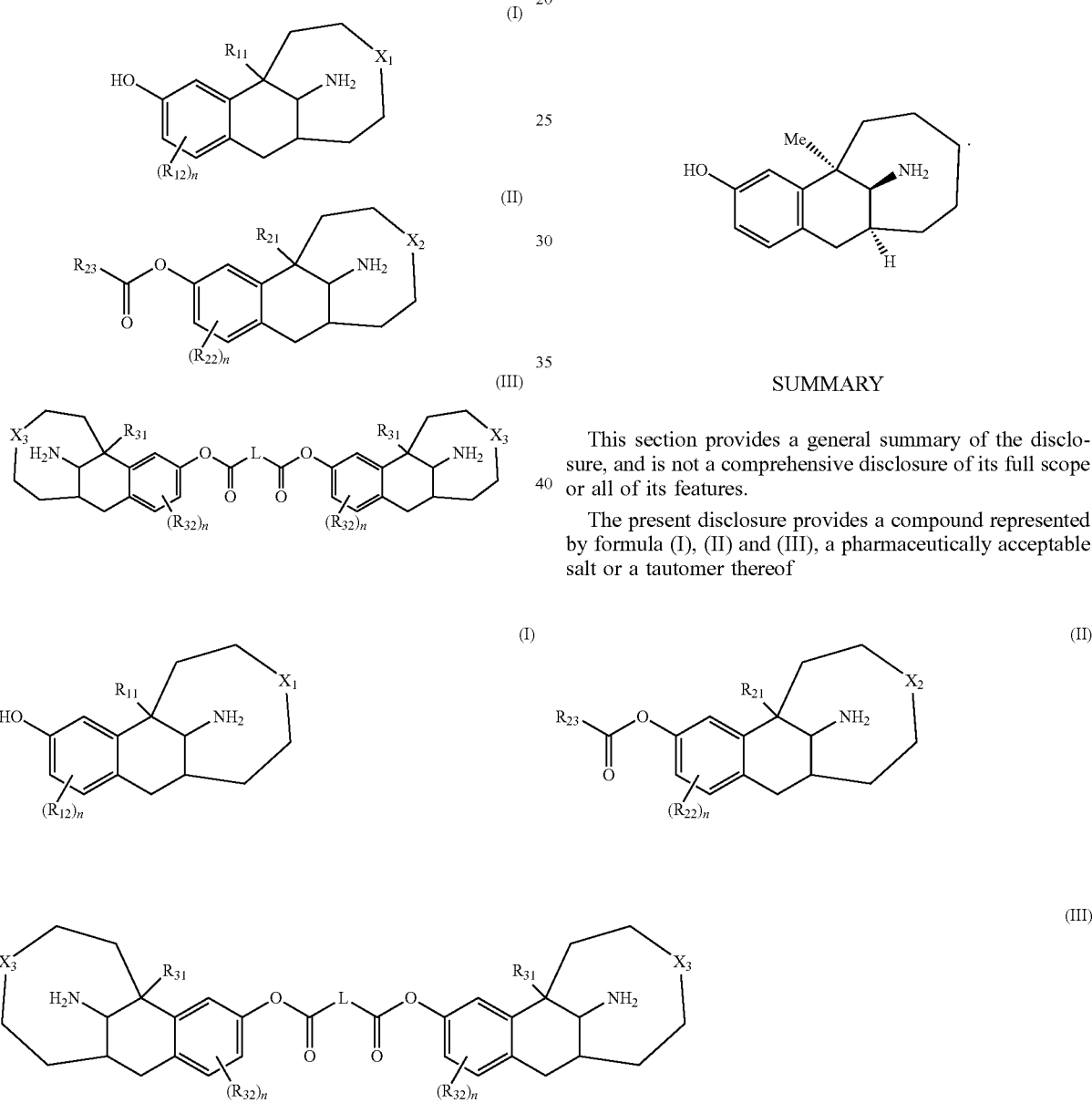

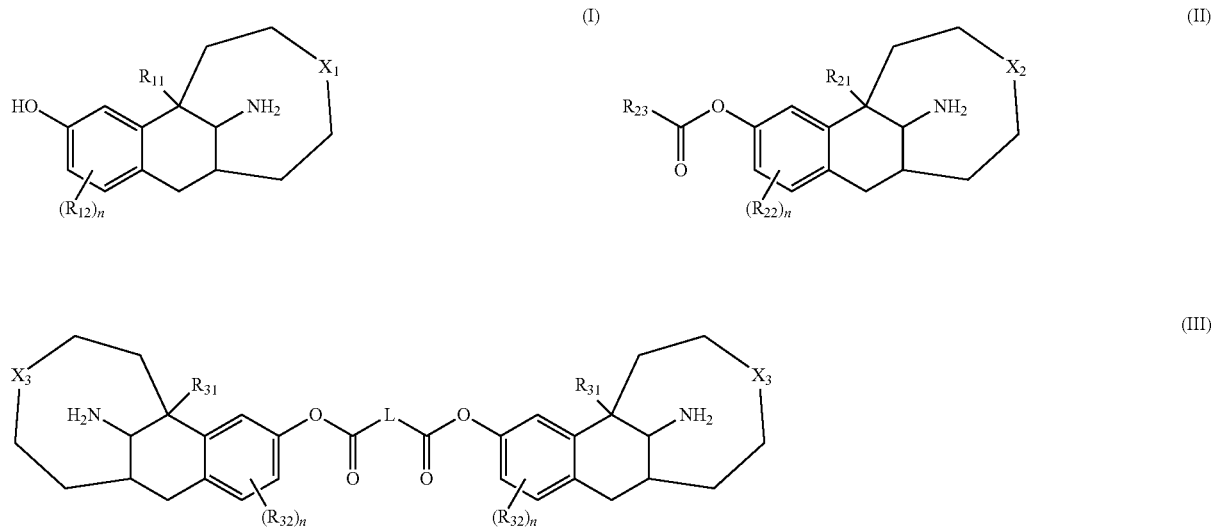

wherein, $X_1$, $X_2$, $X_3$ are each independently selected from a single bond, $CH_2$, $C(RR)$, $NH$, $N(R)$, $O$ or $S$;

$R_{12}$ is selected from H, F, Cl, Br, I, CN, OH, $NH_2$, or the group consisting of $C_{1-6}$ alkyl or heteroalkyl, 3-7 membered cycloalkyl or heterocycloalkyl, and 5-7 membered aryl or heteroaryl, each of which is optionally substituted by 1, 2, or 3 R; and, when X is $CH_2$, $R_{12}$ is not H;

$R_{22}$, $R_{32}$ are each independently selected from H, F, Cl, Br, I, CN, OH, $NH_2$, or the group consisting of $C_{1-6}$ alkyl or heteroalkyl, 3-7 membered cycloalkyl or heterocycloalkyl, and 5-7 membered aryl or heteroaryl, each of which is optionally substituted by 1, 2, or 3 R;

n is 1, 2, or 3;

$R_{11}$, $R_{21}$, $R_{31}$ are each independently selected from the group consisting of $C_{1-6}$ alkyl and $C_{1-6}$ heteroalkyl, each of which is optionally substituted by 1, 2, or 3 R;

$R_{23}$ is selected from the group consisting of $C_{1-12}$ alkyl, $C_{1-12}$ heteroalkyl, $C_{3-7}$ cycloalkyl, and 3-7 membered heterocycloalkyl, each of which is optionally substituted by 1, 2, or 3 R;

L is selected from the group consisting of $C_{1-12}$ alkyl, $C_{1-12}$ heteroalkyl, $C_{3-7}$ cycloalkyl, and 3-7 membered heterocycloalkyl, each of which is optionally substituted by 1, 2, or 3 R;

said "hetero" represents O, S, or N, the number of which is selected from 1, 2 or 3 in any of the above cases;

said R is selected from F, Cl, Br, I, CN, OH, $NH_2$, $C_{1-3}$ alkyl, or $C_{1-3}$ heteroalkyl;

said $C_{1-3}$ alkyl or $C_{1-3}$ heteroalkyl is each optionally substituted by 1, 2, or 3 substituent(s) selected from the group consisting of F, Cl, Br, I, CN, OH, and $NH_2$;

two geminal or ortho R optionally connect to the same atom forming 3-6 cycloalkyl or heterocycloalkyl.

In some embodiments of the present disclosure, $R_{12}$ is selected from H, F, Cl, Br, I, CN, OH, $NH_2$, or the group consisting of $C_{1-5}$ alkyl or heteroalkyl, 3-5 membered cycloalkyl or heterocycloalkyl, 5-6 membered aryl or heteroaryl, each of which is optionally substituted by 1, 2, or 3 R; and when X is $CH_2$, $R_{12}$ is not H.

In some embodiments of the present disclosure, each of $R_{22}$ and $R_{32}$ is independently selected from H, F, Cl, Br, I, CN, OH, $NH_2$, or the groups consisting of $C_{1-5}$ alkyl or heteroalkyl, 3-5 membered cycloalkyl or heterocycloalkyl, and 5-6 membered aryl or heteroaryl, each of which is optionally substituted by 1, 2, or 3 R.

In some embodiments of the present disclosure, $R_{12}$ is selected from H, F, Cl, Br, I, CN, OH, $NH_2$, or the group consisting of $C_{1-5}$ alkyl or heteroalkyl, 3-5 membered cycloalkyl or heterocycloalkyl, 5-6 membered aryl or heteroaryl, each of which is optionally substituted by 1, 2, or 3 R; and when X is $CH_2$, $R_{12}$ is not H;

each of $R_{22}$ and $R_{32}$ is independently selected from H, F, Cl, Br, I, CN, OH, $NH_2$, or the group consisting of $C_{1-5}$ alkyl or heteroalkyl, 3-5 membered cycloalkyl or heterocycloalkyl, and 5-6 membered aryl or heteroaryl, each of which is optionally substituted by 1, 2, or 3 R.

In some embodiments of the present disclosure, $R_{12}$ is selected from H, F, Cl, Br, I, CN, OH, $NH_2$, Me,

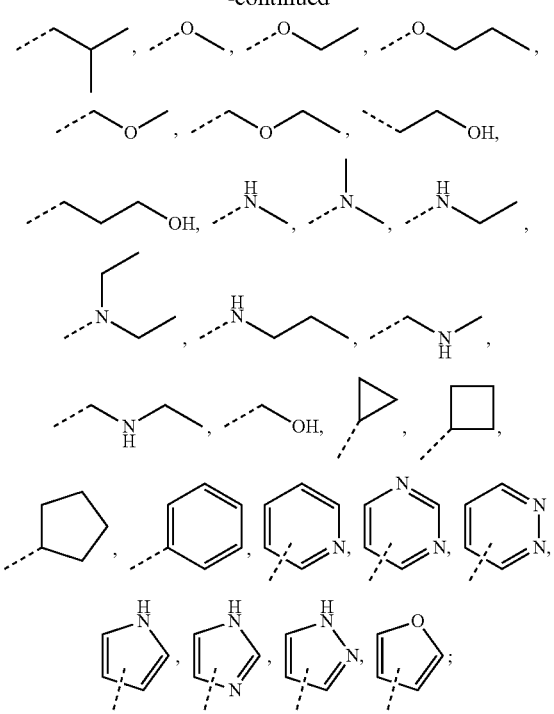

and, when X is $CH_2$, $R_{12}$ is not H.

In some embodiments of the present disclosure, each of $R_{22}$ and $R_{32}$ is independently selected from H, F, Cl, Br, I, CN, OH, $NH_2$, Me,

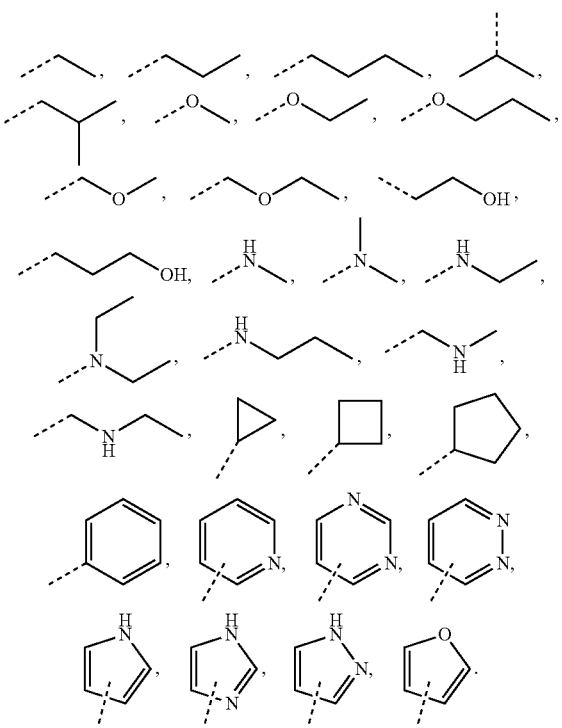

In some embodiments of the present disclosure, $R_{12}$ is selected from H, F, Cl, Br, I, CN, OH, $NH_2$, Me, and when X is CH₂, R₁₂ is not H;
each of R₂₂ and R₃₂ is independently selected from H, F, Cl, Br, I, CN, OH, NH₂, Me, In some embodiments of the present disclosure, R₁₂ is selected from H, F, Cl, Br, I, CN, OH, NH₂, Me, and when X is CH₂, R₁₂ is not H.

In some embodiments of the present disclosure, each of R₂₂ and R₃₂ is independently selected from H, F, Cl, Br, I, CN, OH, NH₂, Me, In some embodiments of the present disclosure, R₁₂ is selected from H, F, Cl, Br, I, CN, OH, NH₂, Me, and, when X is CH₂, R₁₂ is not H;
each of R₂₂ and R₃₂ is independently selected from H, F, Cl, Br, I, CN, OH, NH₂, Me, In some embodiments of the present disclosure, each of R₁₁, R₂₁, and R₃₁ is independently selected from Me, trifluoromethyl, monofluoromethyl, In some embodiments of the present disclosure, L is selected from (CH₂)₄, (CH₂)₅, (CH₂)₆, (CH₂)₇, (CH₂)₈, (CH₂)₉, (CH₂)₁₀,

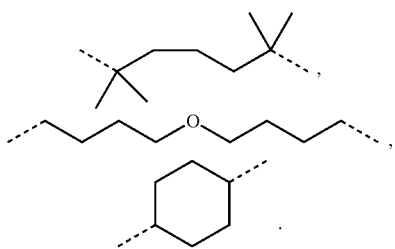

In some embodiments of the present disclosure, R$_{23}$ is selected from

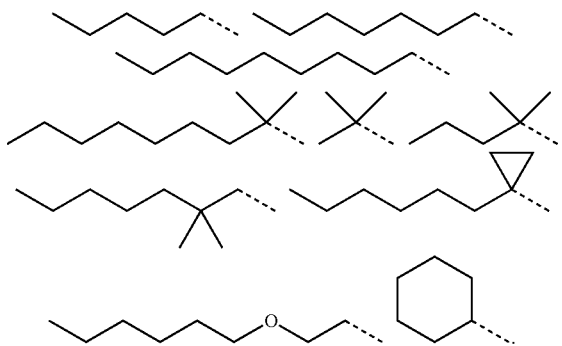

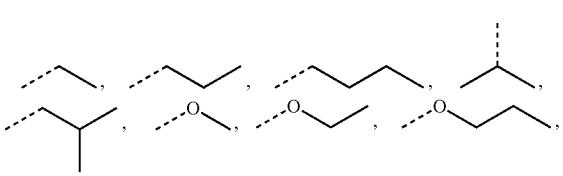

In some embodiments of the present disclosure, R$_{12}$ is selected from H, F, Cl, Br, I, CN, OH, NH$_2$, or the group consisting of C$_{1-5}$ alkyl or heteroalkyl, 3-5 membered cycloalkyl or heterocycloalkyl, 5-6 membered aryl or heteroaryl, each of which is optionally substituted by 1, 2, or 3 R; and, when X is CH$_2$, R$_{12}$ is not H, other variables are defined as above.

In some embodiments of the present disclosure, each of R$_{22}$ and R$_{32}$ is independently selected from H, F, Cl, Br, I, CN, OH, NH$_2$, or the group consisting of C$_{1-5}$ alkyl or heteroalkyl, 3-5 membered cycloalkyl or heterocycloalkyl, and 5-6 membered aryl or heteroaryl, each of which is optionally substituted by 1, 2, or 3 R, other variables are defined as above.

In some embodiments of the present disclosure, R$_{12}$ is selected from H, F, Cl, Br, I, CN, OH, NH$_2$, or the group consisting of C$_{1-5}$ alkyl or heteroalkyl, 3-5 membered cycloalkyl or heterocycloalkyl, 5-6 membered aryl or heteroaryl, each of which is optionally substituted by 1, 2, or 3 R; and, when X is CH$_2$, R$_{12}$ is not H, other variables are defined as above; each of R$_{22}$ and R$_{32}$ is independently selected from H, F, Cl, Br, I, CN, OH, NH$_2$, or the group consisting of C$_{1-5}$ alkyl or heteroalkyl, 3-5 membered cycloalkyl or heterocycloalkyl, 5-6 membered aryl or heteroaryl, each of which is optionally substituted by 1, 2, or 3 R, other variables are defined as above.

In some embodiments of the present disclosure, R$_{12}$ is selected from H, F, Cl, Br, I, CN, OH, NH$_2$, Me,

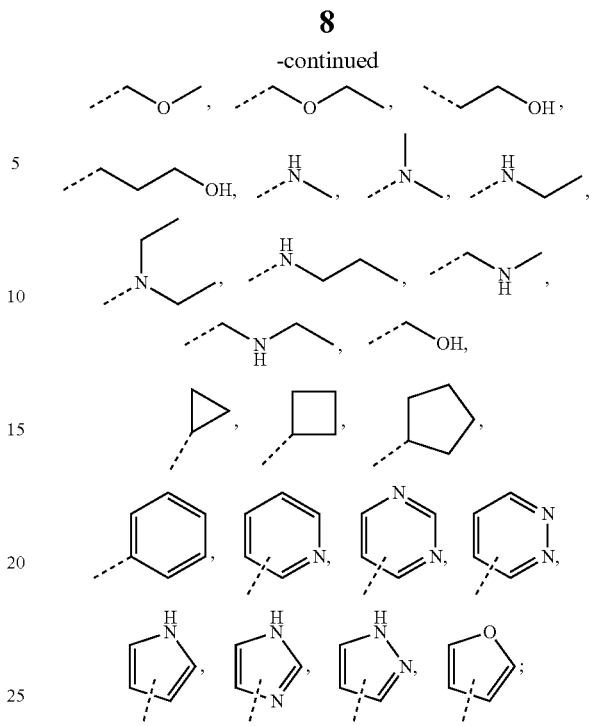

and, when X is CH$_2$, R$_{12}$ is not H, other variables are defined as above.

In some embodiments of the present disclosure, each of R$_{22}$ and R$_{32}$ is independently selected from H, F, Cl, Br, I, CN, OH, NH$_2$, Me,

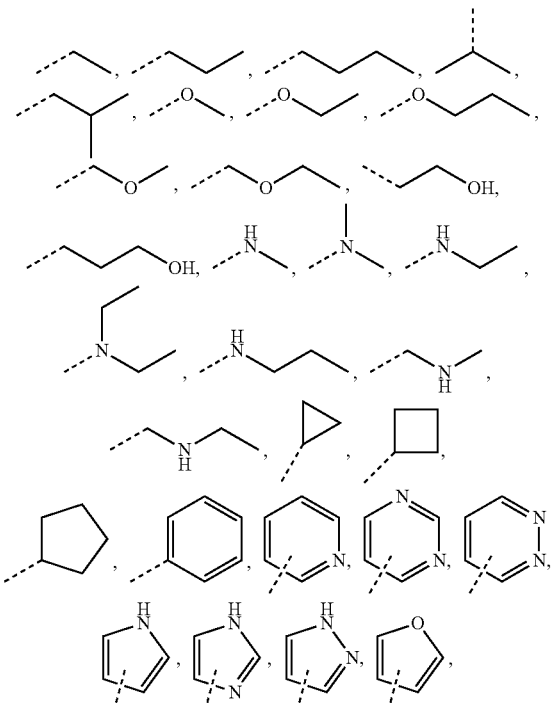

other variables are defined as above.

In some embodiments of the present disclosure, R$_{12}$ is selected from H, F, Cl, Br, I, CN, OH, NH$_2$, Me,

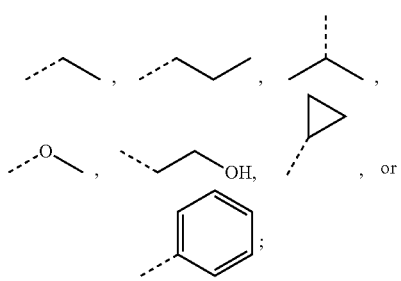

and, when X is CH$_2$, R$_{12}$ is not H, other variables are defined as above.

In some embodiments of the present disclosure, each of R$_{22}$ and R$_{32}$ is independently selected from H, F, Cl, Br, I, CN, OH, NH$_2$, Me,

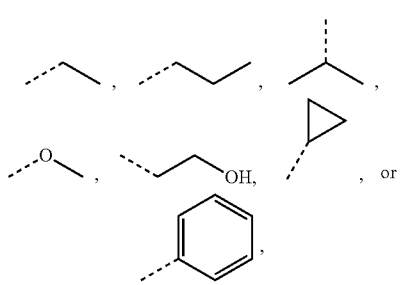

other variables are defined as above.

In some embodiments of the present disclosure, each of R$_{11}$, R$_{21}$, and R$_{31}$ is independently selected from Me,

trifluoromethyl, monofluoromethyl,

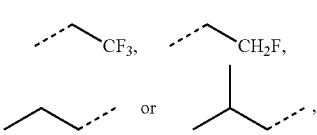

other variables are defined as above.

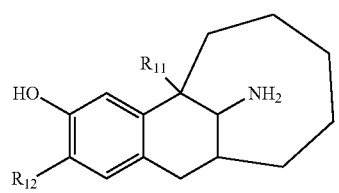

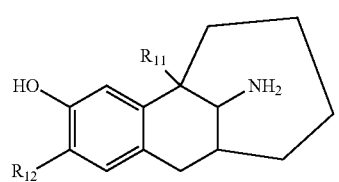

In some embodiments of the present disclosure, L is selected from (CH$_2$)$_4$, (CH$_2$)$_5$, (CH$_2$)$_6$, (CH$_2$)$_7$, (CH$_2$)$_8$, (CH$_2$)$_9$, (CH$_2$)$_{10}$,

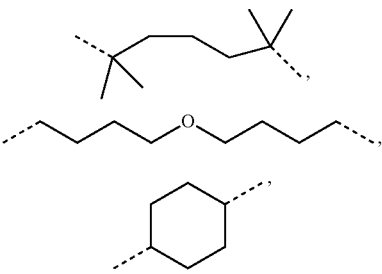

other variables are defined as above.

In some embodiments of the present disclosure, R$_{23}$ is selected from

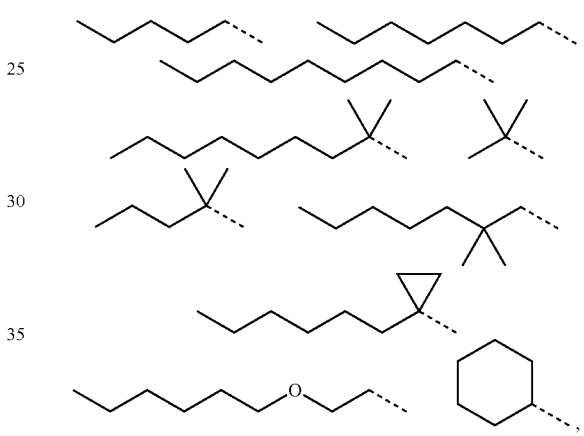

other variables are defined as above.

Some other embodiments of the present disclosure are derived from any combination of the above-mentioned variables.

In some embodiments of the present disclosure, the compound, pharmaceutically acceptable salt or tautomer thereof, is selected from the group consisting of

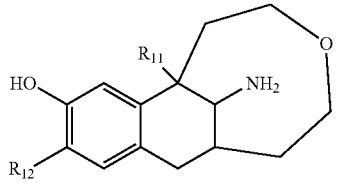

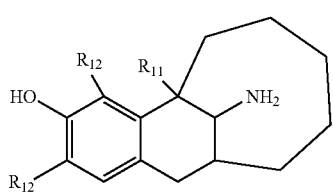

-continued
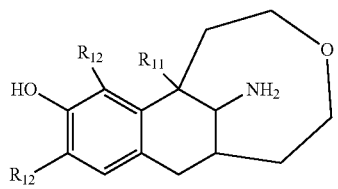
I-5
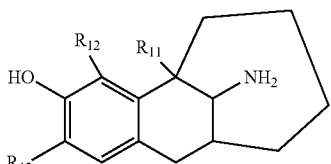
I-6
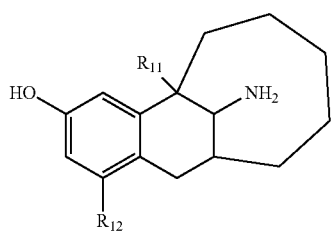
I-7
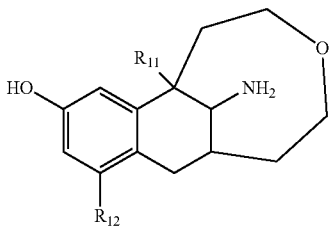
I-8
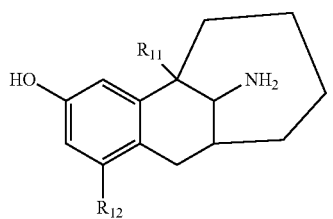
I-9
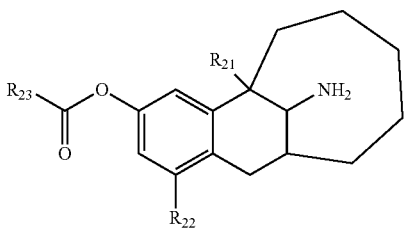
II-1
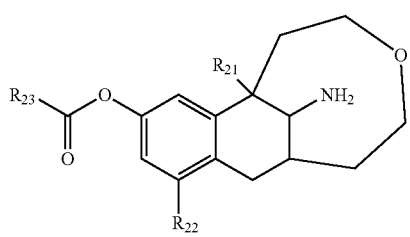
II-2
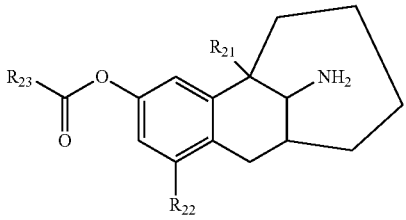
II-3
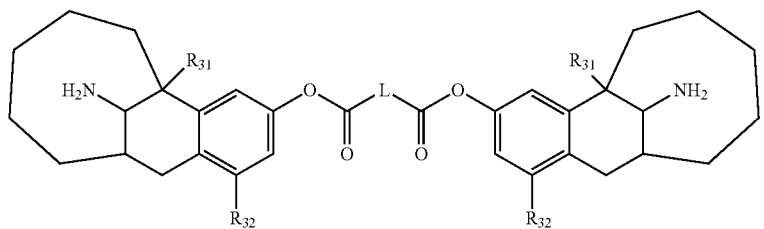
III-1
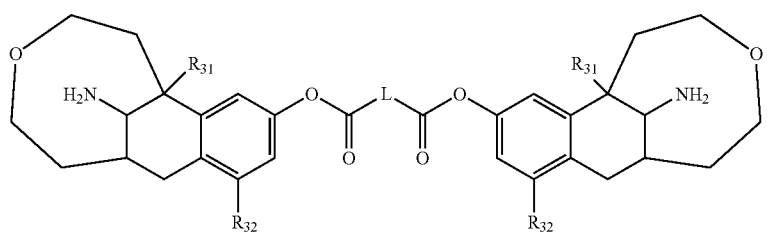
III-2
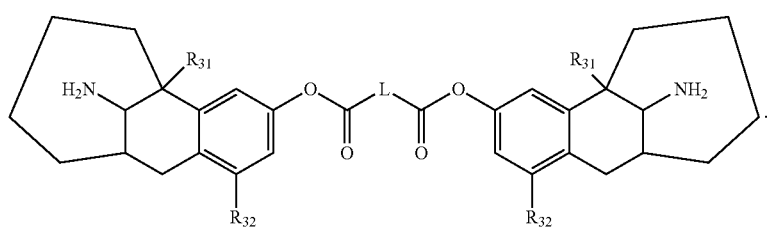
III-3 wherein, L, $R_{11}$, $R_{12}$, $R_{21}$, $R_{22}$, $R_{23}$, $R_{31}$ and $R_{32}$ are defined as above.
The present disclosure also provides a compound selected from the group consisting of
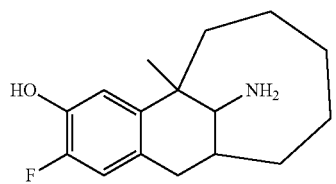
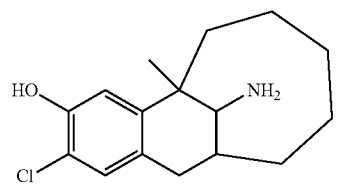
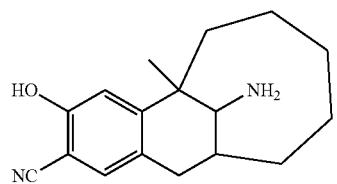
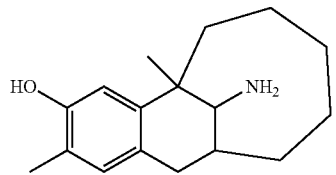
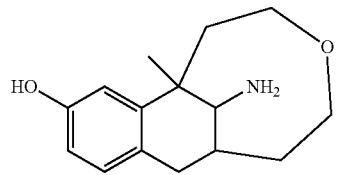
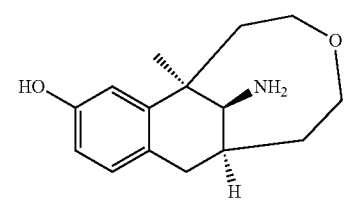
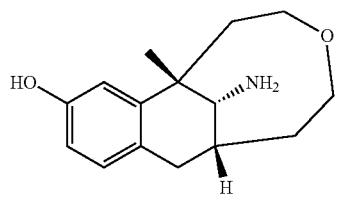
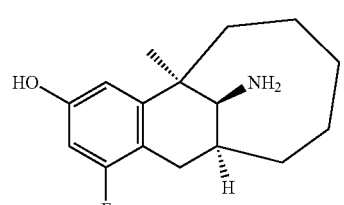
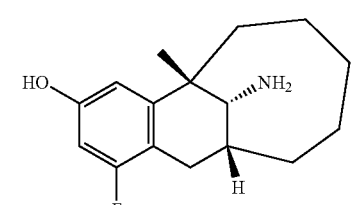
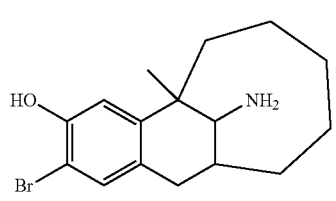
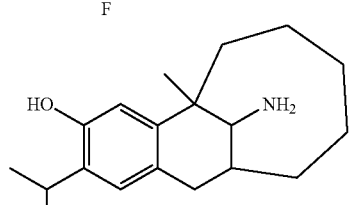
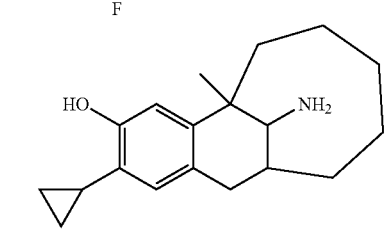
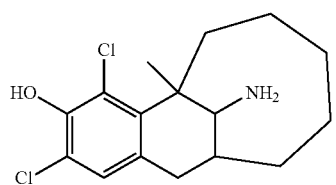
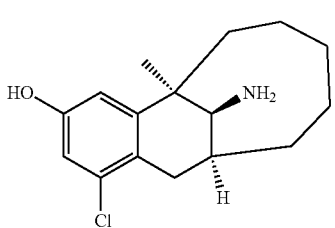
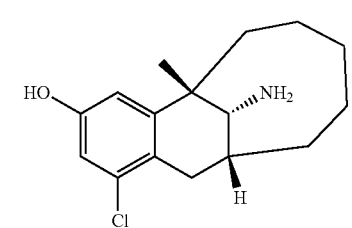
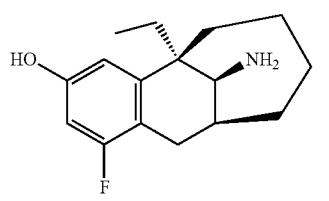
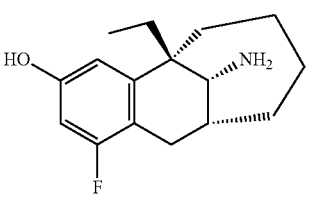
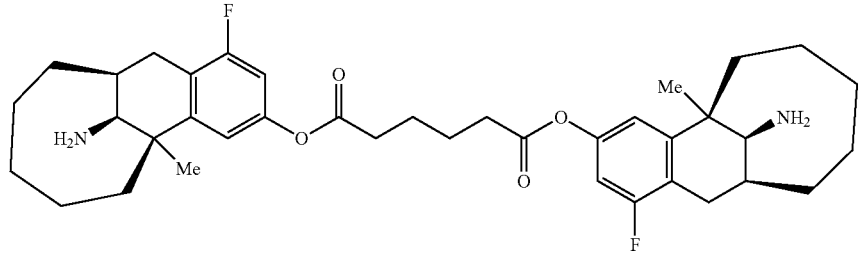

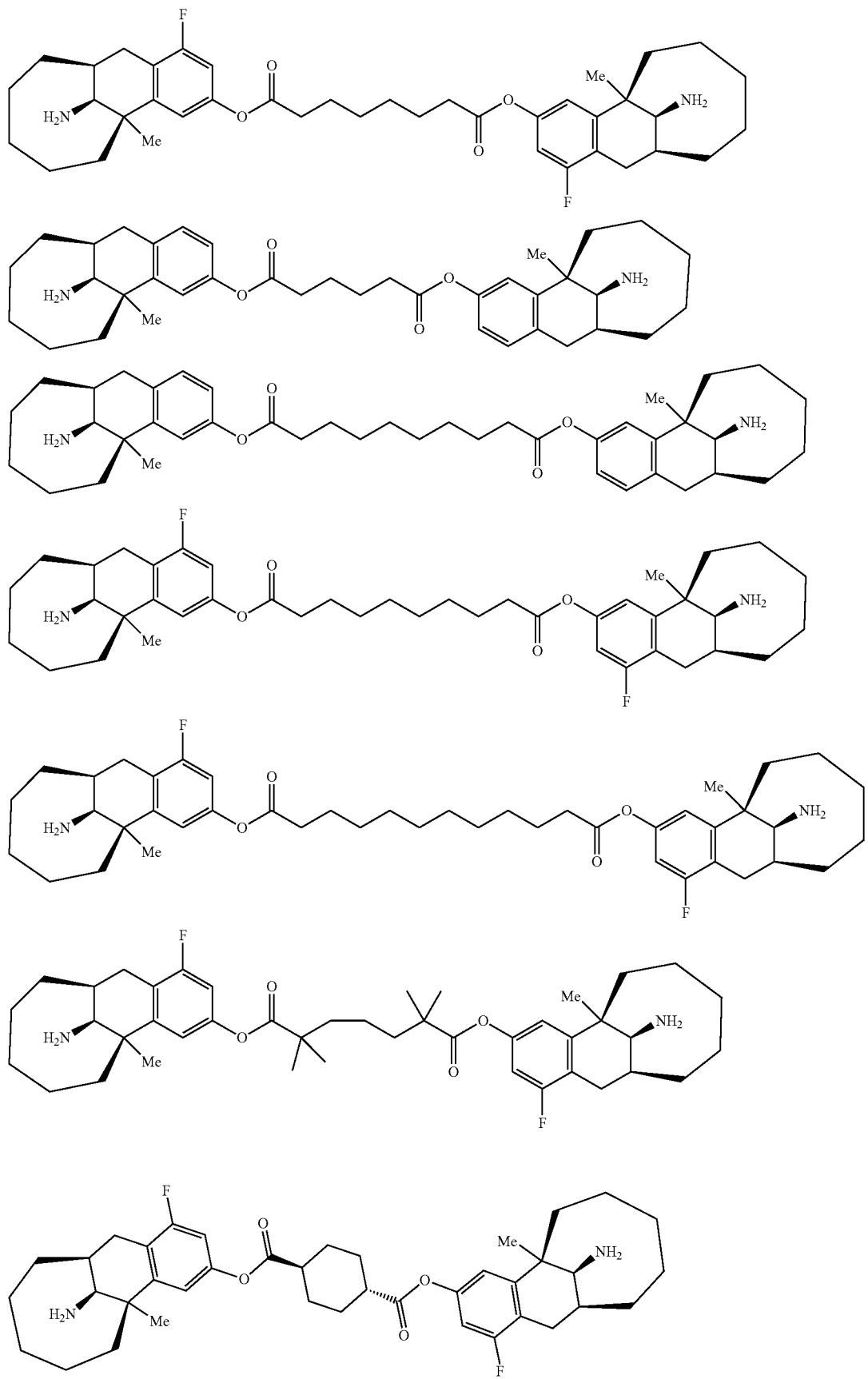

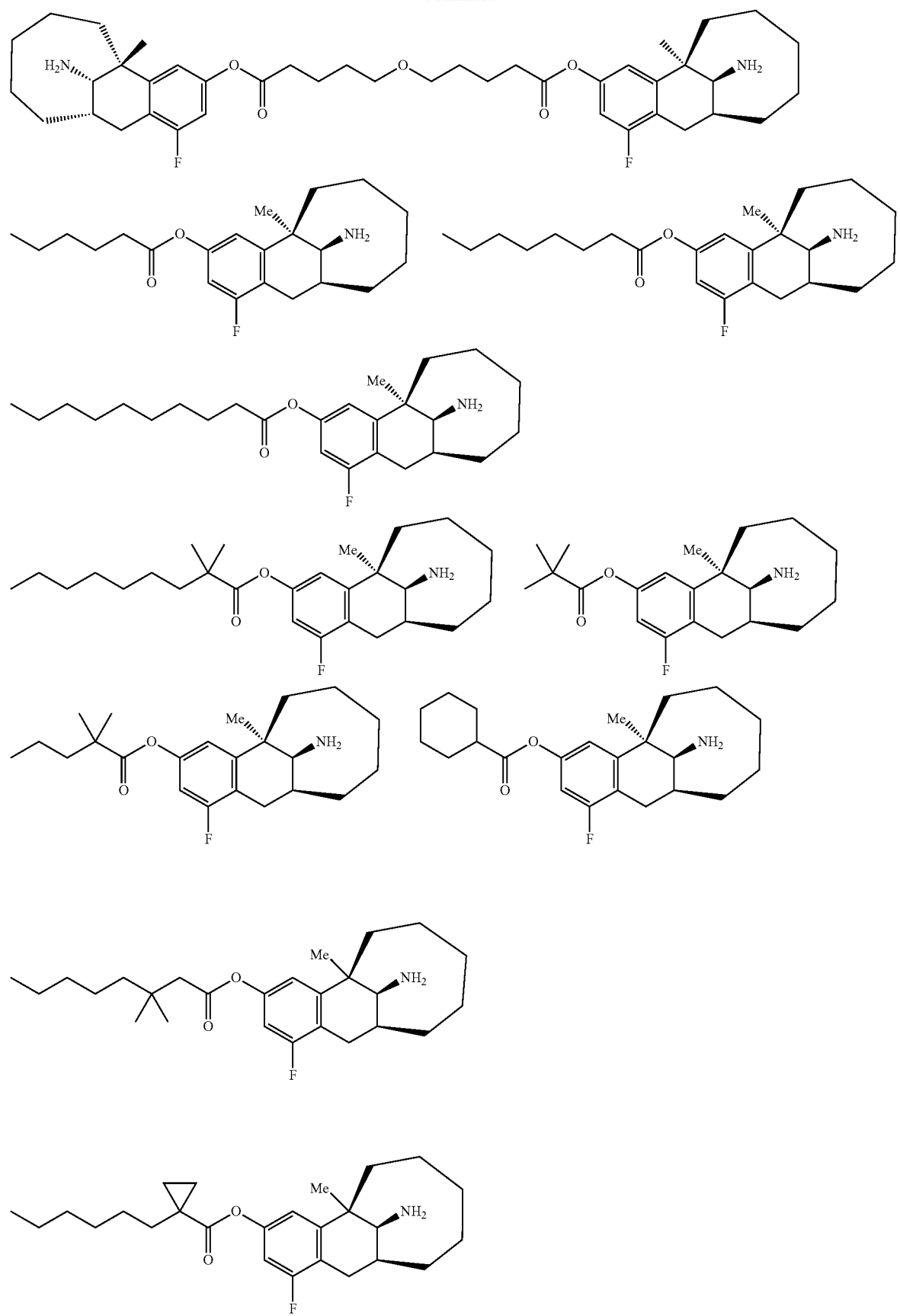

-continued
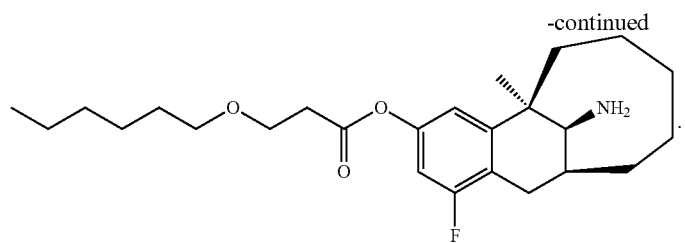
The present disclosure also provides a compound selected from the group consisting of
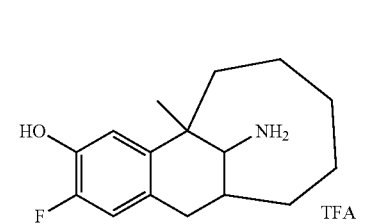
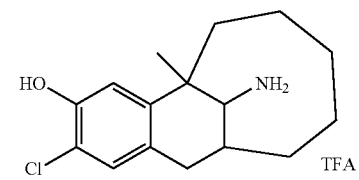
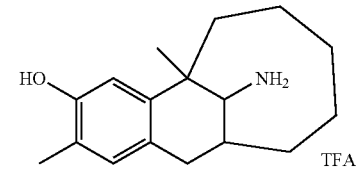
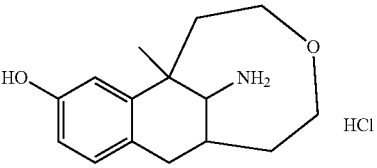
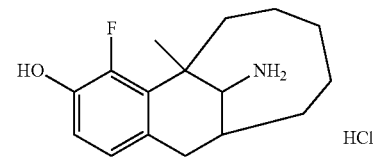
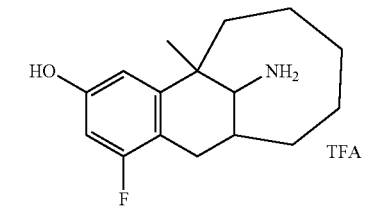
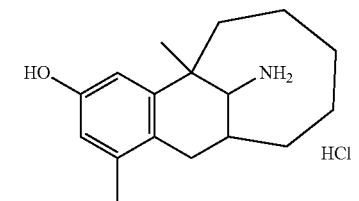
-continued
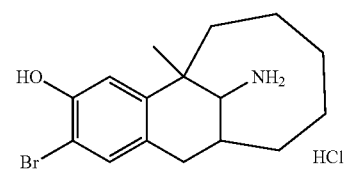
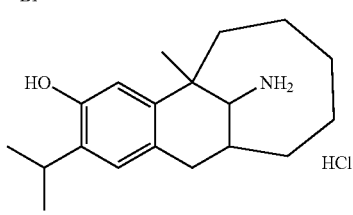
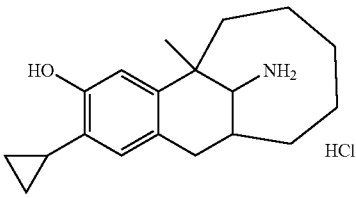
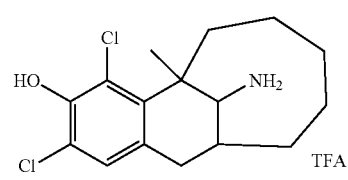
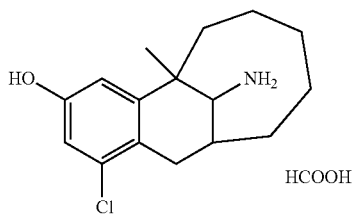
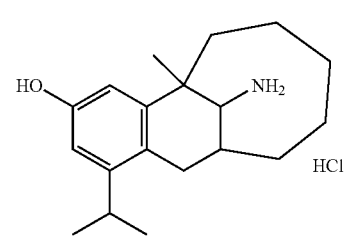

-continued

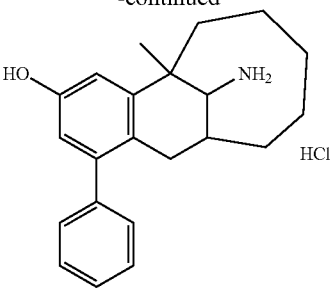

-continued

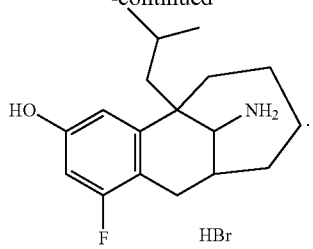

The present disclosure also provides a pharmaceutical composition comprising a therapeutically effective dose of the compound represented by formula (I), (II) and (III) or the pharmaceutically acceptable salt thereof and a pharmaceutically acceptable carrier.

The present disclosure also provides a use of the compound or the pharmaceutically acceptable salt thereof or the pharmaceutical composition in analgesic drugs.

Further areas of applicability will become apparent from the description provided herein. The description and specific examples in this summary are intended for purposes of illustration only and are not intended to limit the scope of the present disclosure.

Unless otherwise indicated, the following terms and phrases used in this document are intended to have the following meanings. A specific term or phrase should not be considered indefinite or unclear in the absence of a particular definition, but should be understood in the ordinary sense. When a trade name appears herein, it is intended to refer to its corresponding commodity or active ingredient thereof.

$C_{1-6}$ is selected from $C_1$, $C_2$, $C_3$, $C_4$, $C_5$ and $C_6$; $C_{3-7}$ is selected from $C_3$, $C_4$, $C_5$, $C_6$ and $C_7$.

$C_{1-12}$ alkyl or heteroalkyl, $C_{3-12}$ cyclo-group or heterocyclohydrocarbyl, $C_{1-12}$ alkyl or heteroalkyl substituted by $C_{3-12}$ cyclohydrocarbyl or heterocyclohydrocarbyl include but not limited to:

$C_{1-12}$ alkyl, $C_{1-12}$ alkylamino, N,N-di($C_{1-12}$ alkyl) amino, $C_{1-12}$ alkoxy, $C_{1-12}$ alkanoyl, $C_{1-12}$ alkoxycarbonyl, $C_{1-12}$ alkylsulfonyl, $C_{1-12}$ alkylsulfinyl, $C_{3-12}$ cycloalkyl, $C_{3-12}$ cycloalkylamino, $C_{3-12}$ heterocycloalkyl amino, $C_{3-12}$ cycloalkyloxy, $C_{3-12}$ cycloalkyl acyl, $C_{3-12}$ cycloalkyloxycarbonyl, $C_{3-12}$ cycloalkylsulfonyl, $C_{3-12}$ cycloalkylsulfinyl, 5-12 membered aryl or heteroaryl, 5-12 membered aralkyl or heteroaralkyl;

methyl, ethyl, n-propyl, isopropyl, —CH$_2$C(CH$_3$)(CH$_3$)(OH), cyclopropyl, cyclobutyl, propyl methylene, cyclopropionyl, benzyloxy, trifluoromethyl, aminomethyl, hydroxymethyl, methoxy, formyl, methoxycarbonyl, methylsulfonyl, methylsulfinyl, ethoxy, acetyl, ethanesulfonyl, ethoxycarbonyl, dimethylamino, diethylamino, dimethylaminocarbonyl, di ethyl aminocarbonyl;

N(CH$_3$)$_2$, NH(CH$_3$), —CH$_2$CF$_3$, —CH$_2$CH$_2$CF$_3$, —CH$_2$CH$_2$F, —CH$_2$CH$_2$S(=O)$_2$CH$_3$, —CH$_2$CH$_2$CN, —CH$_2$CH(OH)(CH$_3$)$_2$, —CH$_2$CH(F)(CH$_3$)$_2$, —CH$_2$CH$_2$F, —CH$_2$CF$_3$, —CH$_2$CH$_2$CF$_3$, —CH$_2$CH$_2$NH$_2$, —CH$_2$CH$_2$OH, —CH$_2$CH$_2$OCH$_3$, —CH$_2$CH$_2$CH$_2$OCH$_3$, —CH$_2$CH$_2$N(CH$_3$)$_2$, —S(=O)$_2$CH$_3$, —CH$_2$CH$_2$S(=O)$_2$CH$_3$; and phenyl, thiazolyl, biphenyl, naphthyl, cyclopentyl, furyl, 3-pyrrolinyl, pyrrolidinyl, 1,3-oxopentyl, pyrazolyl, 2-pyrazolinyl, pyrazolidinyl, imidazolyl, oxazolyl, thiazolyl, 1,2,3-azolyl, 1,2,3-triazolyl, 1,2,4-triazolyl, 1,3,4-thiadiazolyl, 4H-pyranyl, pyridyl, piperidinyl, 1,4-dioxanyl, morpholinyl, pyridazinyl, pyrimidinyl, pyrazinyl, piperazinyl, 1,3,5-trithianyl, 1,3,5-triazinyl, benzofuranyl, benzothiophenyl, indolyl, benzimidazolyl, benzothiazolyl, purinyl, quinolyl, isoquinolyl, cinnolinyl or quinoxalinyl;

The term "pharmaceutically acceptable" is used herein in terms of those compounds, materials, compositions, and/or dosage forms, which are suitable for use in contact with human and animal tissues within the scope of reliable medical judgment, with no excessive toxicity, irritation, allergic reactions or other problems or complications, commensurate with a reasonable benefit/risk ratio.

The term "pharmaceutically acceptable salt" refers to salts of the compounds of the present disclosure that are prepared from the compounds having particular substituents of the present disclosure with relatively non-toxic acids or bases. When compounds of the present disclosure contain relatively acidic functional groups, base addition salts can be obtained by bringing the neutral form of these compounds into contact with a sufficient amount of base in pure solution or suitable inert solvent. Pharmaceutically acceptable base addition salts include salts of sodium, potassium, calcium, ammonium, organic amine or magnesium or similar salts. When compounds of the present disclosure contain relatively basic functional groups, acid addition salts can be obtained by bringing the neutral form of these compounds into contact with a sufficient amount of acid in pure solution or suitable inert solvent. Examples of pharmaceutically acceptable acid addition salts include inorganic acid salts, wherein said inorganic acids include, for example, hydrochloric acid, hydrobromic acid, nitric acid, carbonic acid, bicarbonate, phosphoric acid, monohydrogen phosphate, dihydrogen phosphate, sulfuric acid, hydrogen sulfate, hydroiodic acid, phosphorous acid, and the like; and organic acid salts, wherein said organic acids include, for example, acetic acid, propionic acid, isobutyric acid, maleic acid, malonic acid, benzoic acid, succinic acid, suberic acid, fumaric acid, lactic acid, mandelic acid, phthalic acid, benzenesulfonic acid, p-toluenesulfonic acid, citric acid, tartaric acid, and methanesulfonic acid, and the like; and salts of amino acid (such as arginine and the like), and salts of organic acids such as glucuronic acid and the like (refer to Berge et al., "Pharmaceutical Salts", Journal of Pharmaceutical Science 66: 1-19 (1977)). Certain specific compounds of the present disclosure contain basic and acidic functional groups that can be converted to any base or acid addition salt.

Preferably, through bringing the salt into contact with base or acid in a conventional manner, then separating the parent compound, the neutral form of the compound is thereby regenerated. The difference between the parent form of a compound and its various salt forms lies in certain physical properties, such as different solubility in polar solvents.

"Pharmaceutically acceptable salt" used in this document belongs to derivatives of the compounds of the present disclosure, wherein, the parent compound is modified by forming salt with acid or base. Examples of pharmaceutically acceptable salts include but are not limited to: inorganic acids or organic acid salts of basic moietys such as amines, alkali metal or organic salts of acidic moietys such as carboxylic acids, and the like. Pharmaceutically acceptable salts include conventional non-toxic salts or quaternary ammonium salts of the parent compound, such as the salts formed by non-toxic inorganic acids or organic acids. The conventional non-toxic salts include but are not limited to those salts derived from inorganic acids and organic acids, wherein said inorganic acids or organic acids are selected from 2-acetoxybenzoic acid, 2-hydroxyethanesulfonic acid, acetic acid, ascorbic acid, benzenesulfonic acid, benzoic acid, bicarbonate, carbonic acid, citric acid, edetic acid, ethanedisulfonic acid, ethanesulfonic acid, fumaric acid, glucoheptose, gluconic acid, glutamic acid, glycolic acid, hydrobromic acid, hydrochloric acid, hydroiodide, hydroxyl, hydroxynaphthalene, isethionic acid, lactic acid, lactose, dodecyl sulfonic acid, maleic acid, malic acid, mandelic acid, methanesulfonic acid, nitric acid, oxalic acid, pamoic acid, pantothenic acid, phenylacetic acid, phosphoric acid, polygalactanal acid, propionic acid, salicylic acid, stearic acid, subacetic acid, succinic acid, sulfamic acid, sulfanilic acid, sulfuric acid, tannin, tartaric acid and p-toluenesulfonic acid.

The pharmaceutically acceptable salts of the present disclosure can be synthesized from the parent compound that contains an acidic or basic moiety by conventional chemical methods. In general, such salts can be prepared by reacting the free acid or base forms of these compounds with a stoichiometric amount of appropriate base or acid in water or an organic solvent or a mixture of the two. Generally, non-aqueous media such as ether, ethyl acetate, ethanol, isopropanol or acetonitrile are preferred.

In addition to salt forms, the compounds provided by the present disclosure also exist in prodrug forms. Prodrugs of the compounds described herein are those compounds that readily undergo chemical changes under physiological conditions to to be converted into the compounds of the present disclosure. Additionally, prodrugs can be converted to the compounds of the present disclosure by chemical or biochemical methods in vivo environment.

Certain compounds of the present disclosure can exist in unsolvated forms or solvated forms, including hydrated forms. In general, the solvated forms are equivalent to unsolvated forms, and both are encompassed within the scope of the present disclosure. Certain compounds of the present disclosure can have asymmetric carbon atoms (optical centers) or double bonds. Racemate, diastereomer, geometric isomer and individual isomer are all included within the scope of the present disclosure.

The graphic representations of racemic, ambiscalemic and scalemic or enantiomerically pure compounds used herein are taken from Maehr J. Chem. Ed. 1985, 62, 114-120. Unless otherwise specified, the absolute configuration of a stereogenic center is represented using wedge and dashed bonds ($\nearrow$ ...""), and the relative configuration of a stereogenic center is represented by $\nearrow$ ...". When the compounds described herein contain olefinic double bond or other geometric asymmetric centers, they include E, Z geometric isomers unless otherwise specified. Likewise, all tautomeric forms are included within the scope of the present disclosure.

The compounds of the present disclosure can have particular geometric or stereoisomeric forms. The present disclosure contemplates all such compounds, including cis and trans isomers, (−)- and (+)-enantiomers, (R)- and (S)-enantiomers, diastereoisomers, (D)-isomers, (L)-isomers, and racemic mixtures and other mixtures, for example, enantiomer or diastereoisomer enriched mixtures, all of which belong to the scope of the present disclosure. The substituents such as alkyl can have additional asymmetric carbon atoms. All these isomers and mixtures thereof are included within the scope of the present disclosure.

Optically active (R)- and (S)-isomers, or D and L isomers can be prepared using chiral synthesis or chiral reagents or other conventional techniques. If one kind of enantiomer of certain compound of the present disclosure is to be obtained, the pure desired enantiomer can be obtained by asymmetric synthesis or derivative action of chiral auxiliary followed by separating the resulting diastereomeric mixture and cleaving the auxiliary group. Alternatively, when the molecule contains a basic functional group (such as amino) or acidic functional group (such as carboxyl), the compound reacts with an appropriate optically active acid or base to form a salt of diastereomeric isomer which is then subjected to diastereomeric resolution through conventional methods in the art to give pure enantiomer. In addition, the enantiomers and diastereoisomers are generally separated through chromatography which uses a chiral stationary phase and optionally combines with a chemical derivative method (for example, generating carbamate generated from amine).

The compounds of the present disclosure can contain unnatural proportions of atomic isotopes at one or more of the atoms that constitute the compounds. For example, the compounds can be radiolabeled with radioactive isotopes, such as tritium ($^3$H), iodine-125 ($^{125}$I) or C-14 ($^{14}$C). All isotopic variations of the compounds of the present disclosure, whether radioactive or not, are encompassed within the scope of the present disclosure.

The term "pharmaceutically acceptable carrier" refers to any agent or carrier medium which is capable of delivering an effective amount of the active substances of the present disclosure, does not interfere with the biological activity of the active substances and has no toxic side effects on the host or patient. The representative carrier includes water, oil, vegetable and mineral, cream base, lotion base, ointment base and the like. These bases include suspending agents, thickeners, penetration enhancers and the like. Their formulations are well known to the skilled in the cosmetic field or topical pharmaceutical field. The additional information about the carrier can be referred to *Remington: The Science and Practice of Pharmacy,* 21st Ed, Lippincott, Williams & Wilkins (2005), the disclosure of which is incorporated herein by reference.

The term "excipient" generally refers to a carrier, a diluent and/or a medium required for formulating an effective pharmaceutical composition.

For drug or pharmacologically active agent, the term "effective dose" or "therapeutically effective dose" refers to a nontoxic but sufficient amount to achieve the desired effect of the drug or agent. For oral dosage forms of the present disclosure, an "effective dose" of an active substance in the composition refers to an amount required for achieving the desired effect when combining with another active substance in the composition. An effective amount varies from person to person and is determined depending on the age and general condition of the recipient as well as the specific active substance. The appropriate effective amount in an individual case can be determined by the skilled in the art based on routine experiment.

The term "active ingredient", "therapeutic agent", "active substance" or "active agent" refers to a chemical entity which can effectively treat the target disorder, disease or condition.

The term "substituted" means one or more hydrogen atoms on a specific atom are substituted with substituents, including deuterium and hydrogen variants, as long as the valence of the specific atom is normal and the substituted compound is stable. When the substituent is a ketone (that is =O), it means two hydrogen atoms are substituted. Positions on an aromatic ring cannot be substituted with a ketone. The term "optionally substituted" means an atom can be replaced by a substituent or not, unless otherwise specified, the type and number of the substituents may be arbitrary as long as being chemically achievable.

When any variable (such as R) occurs in the composition or structure of the compound more than one time, the definition of the variable at each occurrence is independent. Thus, for example, if a group is substituted with 0-2 R, the group can be optionally substituted with up to two R, wherein the definition of R at each occurrence is independent. Moreover, a combination of substituents and/or variants thereof is allowed only when the combination results in a stable compound.

When the number of a linking group is 0, such as —(CRR)$_0$—, it means that the linking group is a single bond.

When one of the variables is selected from a single bond, it means that the two groups linked by the single bond are connected directly. For example, when L in A-L-Z represents a single bond, the structure of A-L-Z is actually A-Z.

When a substituent is vacant, it means that the substituent does not exist. For example, when X is vacant in A-X, the structure of A-X is actually A.

When a bond of a substituent can be cross-linked to two atoms on a ring, such substituent can be bonded to any atom of the ring. When the enumerative substituent do not indicate by which atom it is linked to a compound included in the general chemical formula but not specifically mentioned, such substituent can be bonded by any of its atoms. A combination of substituents and/or variants thereof is allowed only when such combination can result in a stable compound. For example, the structural unit

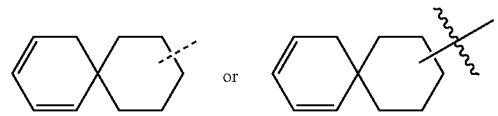

means that it can be substituted at any position on cyclohexyl or cyclohexadiene.

Unless otherwise specified, the term "halo" or "halogen" by itself or as part of another substituent refers to a fluorine, chlorine, bromine or iodine atom. Furthermore, the term "haloalkyl" is meant to include monohaloalkyl and polyhaloalkyl. For example, the term "halo(C$_1$-C$_4$)alkyl" is intended to include, but not limited to, trifluoromethyl, 2,2,2-trifluoroethyl, 4-chlorobutyl, 3-bromopropyl and the like.

Examples of haloalkyl include, but not limited to: trifluoromethyl, trichloromethyl, pentafluoroethyl and pentachloroethyl. "Alkoxy" represents any alkyl defined above having a specified number of carbon atoms attached by an oxygen bridge. C$_{1-6}$ alkoxy includes C$_1$, C$_2$, C$_3$, C$_4$, C$_5$ and C$_6$ alkoxy. Examples of alkoxy include, but not limited to: methoxy, ethoxy, n-propoxy, isopropoxy, n-butoxy, sec-butoxy, tert-butoxy, n-pentyloxy and S-pentoxy. "Cycloalkyl" includes a saturated cyclic group, such as cyclopropyl, cyclobutyl or cyclopentyl. 3-7 cycloalkyl includes C$_3$, C$_4$, C$_5$, C$_6$ and C$_7$ cycloalkyl. "Alkenyl" includes a linear or branched hydrocarbon chain, wherein one or more carbon-carbon double bonds can be present in any stable site on the chain, such as vinyl and propenyl.

The term "halo" or "halogen" refers to fluorine, chlorine, bromine and iodine.

Unless otherwise specified, the term "hetero" means a heteroatom or a heteroatom group (i.e., an atom group containing a heteroatom), including all atoms except carbon (C) and hydrogen (H), and also including atom groups containing the above heteroatoms. The related examples include oxygen (O), nitrogen (N), sulfur (S), silicon (Si), germanium (Ge), aluminum (Al), boron (B), —O—, —S—, =O, =S, —C(=O)O—, —C(=O)—, —C(=S)—, —S(=O), —S(=O)$_2$—, and optionally substituted —C(=O)N(H)—, —N(H)—, —C(=NH)—, —S(=O)$_2$N(H)— or —S(=O)N(H)—.

Unless otherwise specified, the term "ring" represents a substituted or unsubstituted cycloalkyl, heterocycloalkyl, cycloalkenyl, heterocycloalkenyl, cycloalkynyl, heterocycloalkynyl, aryl or heteroaryl. The so-called ring includes a single ring, a double ring, a spiral ring, a ring system having two rings sharing one bond or a bridged ring. The number of atoms on the ring is usually defined as the member number of the ring, for example, a "5-7 membered ring" means that 5 to 7 atoms are arranged in a circle. Unless otherwise specified, the ring optionally contains 1 to 3 heteroatoms. Therefore, a "5-7 membered ring" includes, for example, phenyl, pyridinyl and piperidinyl; on the other hand, the term "5-7 membered heterocycloalkyl ring" includes pyridyl and piperidinyl, but excluding phenyl. The term "ring" also includes a ring system containing at least one ring, wherein each ring independently meets the above definition.

Unless otherwise specified, the term "heterocycle" or "heterocyclo" means stable monocyclic, bicyclic or tricyclic rings containing heteroatoms or heteroatom groups, which can be saturated, partially unsaturated or unsaturated (aromatic) and can contain carbon atoms and 1, 2, 3 or 4 ring heteroatoms independently selected from N, O and S, wherein the above any heterocycle can be fused to a benzene ring to form a bicyclic ring. Nitrogen and sulfur heteroatoms can optionally be oxidized (i.e., NO and S(O) p). Nitrogen atom can be substituted or unsubstituted (i.e., N or NR, wherein R is H or other substituents already defined herein). The heterocycle can be attached to the pendant group of any heteroatom or carbon atom to form a stable structure. If the resulting compound is stable, the heterocycle described herein may have a substitution on a carbon or nitrogen position. Nitrogen atom in the heterocycle is optionally quaternized. In a preferred embodiment, when the total number of S and O atoms in the heterocycle is more than 1, these heteroatoms are not adjacent to each other. In another preferred embodiment, the total number of S and O atoms in the heterocycle is not more than 1. As used herein, the term "aromatic heterocyclic group" or "heteroaryl" refers to a stable 5-, 6- or 7-membered monocyclic or bicyclic or 7-, 8-, 9- or 10-membered bicyclic heterocyclic aromatic ring which contains carbon atoms and 1, 2, 3 or 4 ring heteroatoms independently selected from N, O and S. Nitrogen atom can be substituted or unsubstituted (i.e., N or NR, wherein R is H or other substituents already defined herein). Nitrogen and sulfur heteroatoms may optionally be oxidized (i.e., NO and S(O) p). It is worth noting that the total number of S and O atoms in an aromatic heterocycle is not more than one. Bridged ring is also included in the definition of heterocycle. A bridged ring is formed when one or more atoms (ie, C, O, N or S) link two non-adjacent carbon or nitrogen atoms. A preferred bridged ring includes, but not limited to: one carbon atom, two carbon atoms, one nitrogen atom, two nitrogen atoms and one carbon-nitrogen group. It is worth noting that a bridge always converts a monocyclic ring to a tricyclic ring. In a bridged ring, the substituents on the ring may also be present on the bridge.

Examples of the heterocyclic compounds include, but are not limited to: acridinyl, azocinyl, benzimidazolyl, benzofuranyl, benzomercaptofuranyl, benzomercaptophenyl, benzoxazolyl, benzoxazolinyl, benzothiazolyl, benzotriazolyl, benzotetrazolyl, benzoisoxazolyl, benzoisothiazolyl, benzoimidazolinyl, carbazolyl, 4aH-carbazolyl, carbolinyl, chromanyl, chromene, cinnolinyl decahydroquinolinyl, 2H,6H-1,5,2-dithiazinyl, dihydrofuro[2,3-b]tetrahydrofuranyl, furanyl, furazanyl, imidazolidinyl, imidazolinyl, imidazolyl, 1H-indazolyl, indolenyl, indolinyl, indolizinyl, indolyl, 3H-indolyl, isobenzofuranyl, isoindolyl, isoindolinyl, isoquinolinyl, isothiazolyl, isoxazolyl, methylenedioxyphenyl, morpholinyl, naphthyridinyl, octahydro-isoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, hydroxindolyl, pyrimidinyl, phenanthridinyl, phenanthrolinyl, phenazine, phenothiazine, benzoxanthinyl, phenoloxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyrido-oxazolyl, pyrido-imidazolyl, pyrido-thiazolyl, pyridinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, isothiazolylthienyl, thienyl, thieno-oxazolyl, thieno-thiazolyl, thieno-imidazolyl, triazinyl, 1,2,3-triazolyl, 1,2,4-triazolyl, 1,2,5-triazolyl, 1,3,4-triazolyl and xanthenyl. Also included are fused-ring compounds and spiro compounds.

Unless otherwise specified, the term "hydrocarbyl" or subordinate concept thereof (such as alkyl, alkenyl, alkynyl, and phenyl, etc.), by itself or as part of another substituent, means a linear, branched chain or cyclic hydrocarbon radicals or any combinations thereof. They can be fully saturated, mono- or polyunsaturated, can be mono-, di- or poly-substituted, can be a monovalent (such as methyl), divalent (such as methylene) or multivalent (such as methenyl), can also include divalent or multivalent radicals and have a specified number of carbon atoms (for example, $C_1$-$C_{12}$ indicates 1 to 12 carbon atoms, $C_{1-12}$ is selected from $C_1$, $C_2$, $C_3$, $C_4$, $C_5$, $C_6$, $C_7$, $C_8$, $C_9$, $C_{10}$, $C_{11}$ and $C_{12}$; $C_{3-12}$ is selected from $C_3$, $C_4$, $C_5$, $C_6$, $C_7$, $C_8$, $C_9$, $C_{10}$, $C_{11}$ and $C_{12}$). The term "hydrocarbyl" includes, but is not limited to aliphatic hydrocarbyl and aromatic hydrocarbyl. The aliphatic hydrocarbyl includes linear and cyclic hydrocarbyl, specifically includes but not limited to an alkyl, alkenyl, and alkynyl. The aromatic hydrocarbyl includes but is not limited to 6-12 membered aromatic hydrocarbyl such as phenyl, naphthyl and the like. In some embodiments, the term "alkyl" means a linear or branched radical or a combination thereof which can be fully saturated, mono- or polyunsaturated, and can include a divalent or multivalent radical. Examples of saturated hydrocarbyl radicals include, but are not limited to, methyl, ethyl, n-propyl, isopropyl, n-butyl, tert-butyl, isobutyl, sec-butyl, cyclohexyl, (cyclohexyl)methyl, cyclopropylmethyl, and homologs or isomers of n-amyl, n-hexyl, n-heptyl, n-octyl and other atom groups. The unsaturated alkyl has one or more double or triple bonds. Examples of unsaturated alkyl include but are not limited to, vinyl, 2-propenyl, butenyl, crotyl, 2-isopentenyl, 2-(butadienyl), 2,4-pentadienyl, 3-(1,4-pentadienyl), ethynyl, 1- and 3-propynyl, 3-butynyl, and more advanced homologs and isomers.

Unless otherwise specified, the term "heterohydrocarbyl" or subordinate concept thereof (such as heteroalkyl, heteroalkenyl, heteroalkynyl, and heteroaryl, etc.), by itself or as part of another substituent, means a stable linear, branched or cyclic hydrocarbon radical or any combinations thereof, which have a specified number of carbon atoms and at least one heteroatom. In some embodiments, the term "heteroalkyl" by itself or in combination with another term represents a stable linear chain, branched hydrocarbon radical or combinations thereof which have a specified number of carbon atoms and at least one hetero atom. In a typical embodiment, a heteroatom is selected from B, O, N and S, wherein nitrogen and sulfur atoms are optionally oxidized and the nitrogen atom is optionally quaternized. Heteroatom or heteroatom radicals can be located at any interior position in a heterohydrocarbyl, including the position where the hydrocarbyl attaches to the rest part of the molecule. But terms "alkoxy", "alkylamino" and "alkylthio" (or thioalkyl) are used by their conventional meanings and refer to those alkyl groups connected to the rest part of the molecule via an oxygen atom, an amino or a sulfur atom respectively. Examples include, but are not limited to, —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$—S(O)—$CH_3$, —$CH_2$—$CH_2$—S(O)$_2$—$CH_3$, —CH=CH—O—$CH_3$, —$CH_2$—CH=N—$OCH_3$ and —CH=CH—N($CH_3$)—$CH_3$. Up to two consecutive heteroatoms can be present, such as, —$CH_2$—NH—$OCH_3$.

Terms "alkoxy", "alkylamino" and "alkylthio" (or thioalkyl) are used by their conventional meanings and refer to those alkyl groups connected to the remainder of the molecule via an oxygen atom, an amino or a sulfur atom respectively.

Unless otherwise specified, the term "cyclohydrocarbyl", "heterocyclohydrocarbyl" or the subordinate concept thereof (such as aryl, heteroaryl, cycloalkyl, heterocycloalkyl, cycloalkenyl, heterocycloalkenyl, cycloalkynyl, heterocycloalkynyl, etc.) by itself or in combination with another term represents cyclized "hydrocarbyl" or "heterohydrocarbyl". Furthermore, for heterohydrocarbyl or heterocyclohydrocarbyl (e.g. heteroalkyl, and heterocycloalkyl), one heteroatom can occupy the position where the heterocycle attaches to the remainder position of the molecule. Examples of cycloalkyl include, but are not limited to, cyclopentyl, cyclohexyl, 1-cyclohexenyl, 3-cyclohexenyl, cycloheptyl and the like. Non-limiting examples of heterocycloalkyl include 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydro-thiophen-2-yl, tetrahydro-thiophen-3-yl, 1-piperazinyl and 2-piperazinyl.

Unless otherwise specified, the term "alkyl" is used to denote a linear chain or branched saturated hydrocarbon group, can be mono-substituted (such as —$CH_2F$) or poly-substituted (such as —$CF_3$), can be monovalent (such as methyl), divalent (such as methylene) or multivalent (such as methenyl). Examples of alkyl include methyl (Me), ethyl (Et), propyl (such as n-propyl and isopropyl), butyl (such as n-butyl, isobutyl, s-butyl, t-butyl), pentyl (such as n-pentyl, isopentyl, neopentyl) and the like.

Unless otherwise specified, "alkenyl" refers to an alkyl group having one or more carbon-carbon double bonds at any position on the chain, can be mono-substituted or poly-substituted, and can be monovalent, divalent or multivalent. Examples of alkenyl include ethenyl, propenyl, butenyl, pentenyl, hexenyl, butadienyl, pentadienyl, hexadienyl, and the like.

Unless otherwise specified, "alkynyl" refers to an alkyl group having one or more carbon-carbon triple bonds at any position on the chain, can be mono-substituted or poly-substituted, and can be monovalent, divalent or multivalent. Examples of alkynyl groups include ethynyl, propynyl, butynyl, pentynyl, hexynyl, and the like.

Unless otherwise specified, cycloalkyl includes any stable cyclic or polycyclic hydrocarbyl, and any carbon atom is saturated, can be mono-substituted or poly-substituted, can be monovalent, divalent or multivalent. Examples of these cycloalkyl include, but are not limited to, cyclopropyl, norbornanyl, [2.2.2]bicyclooctane, [4.4.0]bicyclodecanyl and the like.

Unless otherwise specified, cycloalkenyl includes any stable cyclic or polycyclic hydrocarbyl having one or more unsaturated carbon-carbon single bonds at any position on the ring, can be mono-substituted or poly-substituted, and can be monovalent, divalent or multivalent. Examples of these cycloalkenyl include, but are not limited to, cyclopentenyl, cyclohexenyl and the like.

Unless otherwise specified, cycloalkynyl includes any stable cyclic or polycyclic hydrocarbyl having one or more carbon-carbon triple bonds at any position on the ring, can be mono-substituted or poly-substituted, and can be monovalent, divalent or multivalent.

Unless otherwise specified, the term "halo" or "halogen" by itself or as part of another substituent refers to fluorine, chlorine, bromine or iodine atom. Furthermore, the term "haloalkyl" is meant to include monohaloalkyl and polyhaloalkyl. For example, the term "halo($C_1$-$C_4$)alkyl" is intended to include, but not limited to, trifluoromethyl, 2,2,2-trifluoroethyl, 4-chlorobutyl, 3-bromopropyl and the like. Examples of haloalkyl include, but not limited to: trifluoromethyl, trichloromethyl, pentafluoroethyl and pentachloroethyl.

"Alkoxy" represents any alkyl defined above having a specified number of carbon atoms attached by an oxygen bridge. $C_{1-6}$ alkoxy includes $C_1$, $C_2$, $C_3$, $C_4$, $C_5$ and $C_6$ alkoxy. Examples of alkoxy include, but not limited to: methoxy, ethoxy, n-propoxy, isopropoxy, n-butoxy, sec-butoxy, tert-butoxy, n-pentyloxy and S-pentoxy.

Unless otherwise specified, the term "aryl" means a polyunsaturated aromatic substituent, can be mono-, di- or poly-substituted, can be a monovalent, divalent or multivalent, can be a single ring or multiple rings (such as one to three rings; wherein at least one ring is aromatic), which are fused together or linked covalently. The term "heteroaryl" refers to an aryl (or ring) containing one to four heteroatoms. In an illustrative example, the heteroatom is selected from B, O, N and S, wherein nitrogen and sulfur atoms are optionally oxidized and the nitrogen atom is optionally quaternized. A heteroaryl may attach to the rest part of a molecule via a heteroatom. Non-limiting examples of aryl or heteroaryl include phenyl, naphthyl, biphenyl, pyrrolyl, pyrazolyl, imidazolyl, pyrazinyl, oxazolyl, phenyl-oxazolyl, isoxazolyl, thiazolyl, furanyl, thienyl, pyridyl, pyrimidinyl benzothiazolyl, purinyl, benzimidazolyl, indolyl, isoquinolyl, quinoxalinyl, quinolyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl and 6-quinolyl. The substituents of any of the above aryl and heteroaryl ring systems are selected from the acceptable substituents described below.

For the sake of convenience, when combined with other terms (such as aryloxy, arylthio, arylalkyl), the aryl includes all the aryl and heteroaryl rings as defined above. Thus, the term "aralkyl" is meant to include those radicals (such as benzyl, phenethyl, pyridylmethyl, and the like) where an aryl is attached to an alkyl including an alkyl where the carbon atom (such as methylene) has been replaced by an atom such as oxygen, for example, phenoxymethyl, 2-pyridyloxy, 3-(1-naphthyloxy)propyl, and the like.

The term "leaving group" refers to a functional group or atom which can be substituted by another functional group or atom through a substitution reaction (such as an affinity substitution reaction). For example, representative leaving groups include triflate; chlorine, bromine and iodine; sulfonate groups, such as mesylate, tosylate, p-bromobenzenesulfonate, p-toluenesulfonates and the like; acyloxy, such as acetoxy, trifluoroacetoxy and the like.

The term "protecting group" includes, but is not limited to "nitrogen protecting group", "hydroxyl protecting group" or "sulphur protecting group." The term "amino protecting group" means a protecting group suitable for blocking side reactions on nitrogen of the amino. Representative amino protecting groups include, but are not limited to: formyl; acyl, such as alkanoyl (e.g. acetyl, trichloroacetyl or trifluoroacetyl); alkoxycarbonyl, such as tert-butoxycarbonyl (Boc); arylmethoxycarbonyl such as benzyloxycarbonyl (Cbz) and 9-fluorenylmethoxycarbonyl (Fmoc); arylmethyl such as benzyl (Bn), trityl (Tr), 1,1-bis-(4'-methoxyphenyl) methyl; silyl such as trimethylsilyl (TMS) and tert-butyldimethylsilyl (TBS) and the like. The term "hydroxy protecting group" refers to a protecting group suitable for blocking side reactions on the hydroxyl group. Representative hydroxy protecting groups include, but are not limited to: alkyl such as methyl, ethyl and t-butyl; acyl, e.g. alkanoyl (e.g. acetyl); arylmethyl such as benzyl (Bn), p-methoxybenzyl (PMB), 9-fluorenylmethyl (Fm), and diphenylmethyl (benzhydryl, DPM); silyl such as trimethylsilyl (TMS) and tert-butyl dimethyl silyl (TBS) and the like.

The compounds of the present disclosure can be prepared by a variety of synthetic methods well known to the skilled, including the following specific embodiments, the embodiments formed by the following specific embodiments in combination with other chemical synthesis methods and the equivalent replacement well known to the skilled in the art. The preferred embodiments include, but are not limited to the examples of the present disclosure.

All solvents used in the present disclosure are commercially available.

The present disclosure employs the following abbreviations: aq represents water; eq represents equivalent and equal; Tol represents toluene; mCPBA represents m-chloroperoxybenzoic acid; TBAB represents tetrabutylammonium bromide; THF represents tetrahydrofuran; DMF represents N,N-dimethylformamide; Pd(dppf)Cl$_2$ represents [1,1'-bis(diphenylphosphino)ferrocene]dichloropalladium; Pd$_2$(dba)$_3$ represents tris(dibenzylideneacetone)dipalladium; AC$_2$O represents acetic anhydride; NBS represents N-bromosuccinimide; MeCN represents acetonitrile; Boc represents tert-butyloxy carbonyl group, which is an amine protecting group; Boc$_2$O represents di-tert-butyl dicarbonate; DCM represents dichloromethane; NCS represents N-chlorosuccinimide; NF SI represents N-fluoro-N-(phenylsulfonyl)benzenesulfonamide; BuLi represents n-butyllithium; TEA represents triethylamine; Pd/C represents palladium on carbon catalyst; AcOH represents glacial acetic acid; AcONa represents sodium acetate; Pd(OAc)$_2$ represents palladium acetate; xPhos represents 2-dicyclohexylphosphino-2',4',6'-triisopropylbiphenyl; DMA represents dimethylacetamide.

Compounds are named manually or by ChemDraw® software, the commercially available compounds use their vendor directory names.

DETAILED DESCRIPTION

The present disclosure will be specifically described below by way of examples, but the scope of the present disclosure is not limited thereto.

Example 1: Preparation of Compound 1

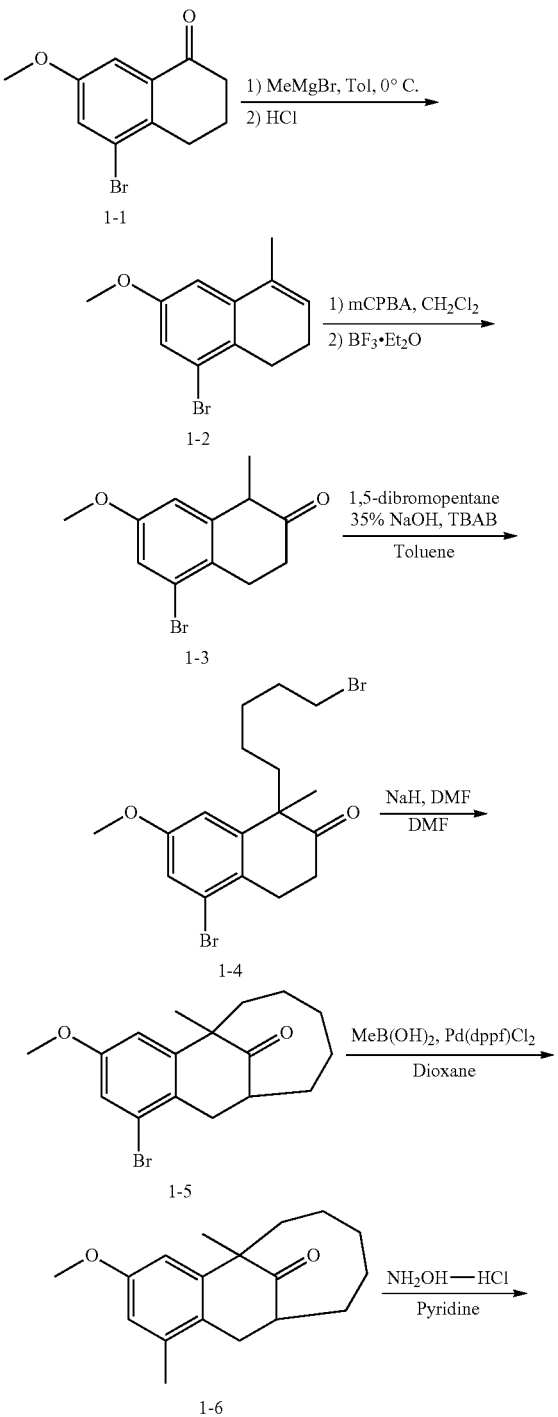

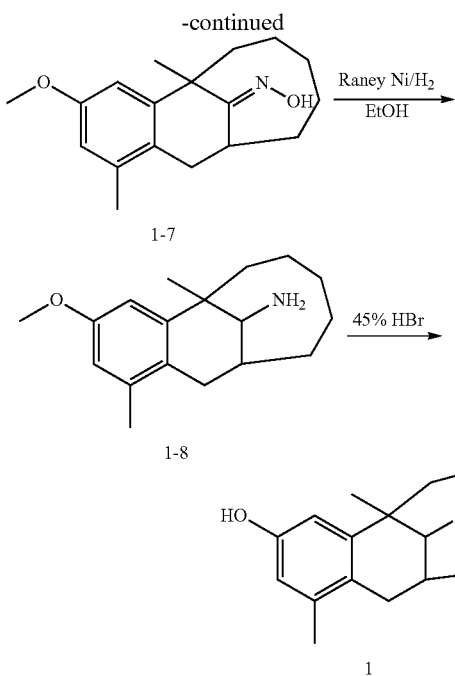

Step 1: Preparation of Compound 1-2

Under nitrogen atmosphere, a solution of MeMgBr in ether (16.33 mL, 48.99 mmol) was slowly added dropwise to a solution of compound 1-1 (5.00 g, 19.60 mmol) in toluene (100 mL) at 0° C. After the reaction temperature was slowly raised to 25° C., the mixture was further stirred for 3 hours. The reaction was quenched with saturated $NH_4Cl$ solution (100 mL) and the aqueous phase was extracted with ethyl acetate (150 mL×3). The combined organic phase was washed with saturated brine (50 mL), dried over anhydrous $Na_2SO_4$ and concentrated in vacuo to approximately 100 mL. The remaining solution was added with aqueous HCl (6M, 20 mL), the mixture was stirred vigorously at 25° C. for 3 hours and extracted with ethyl acetate (200 mL×3). The combined organic phase was washed with saturated brine (100 mL), dried over anhydrous $Na_2SO_4$ and concentrated in vacuo. The residue was purified by silica gel column chromatography (eluent: petroleum ether/ethyl acetate=30/1 to 20/1) to give product 1-2 as a colorless oil (4.00 g, yield: 80.62%). $^1$H NMR (400 MHz, $CDCl_3$): δ 6.97 (d, J=2.4 Hz, 1H), 6.79 (d, J=2.4 Hz, 1H), 5.92 (dt, $J_1$=1.2 Hz, $J_2$=4.4 Hz, 1H), 3.82 (s, 3H), 2.84 (t, J=8.0 Hz, 2H), 2.27 (ddt, $J_1$=2.0 Hz, $J_2$=4.4 Hz, $J_3$=8.0 Hz, 2H), 2.04 (q, J=1.6 Hz, 3H).

The following compounds were synthesized according to a method similar to that of compound 1-2:

| Coumpound number | Structure | Spectrogram |
|---|---|---|
| 2-2 | 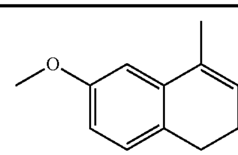 | $^1$H NMR (400 MHz, $CDCl_3$): δ 7.06-7.04 (d, J = 8.0 Hz, 1H), 6.82-6.81 (d, J = 2.4 Hz, 1H), 6.71-6.68 (dd, $J_1$ = 2.8 Hz, $J_2$ = 2.4 Hz, 1H), 5.89-5.87 (m, 1H), 3.81 (s, 1H), 2.72-2.66 (m, 2H), 2.24-2.22 (m, 2H), 2.05-2.04 (m, 3H). |
| 3-2 | 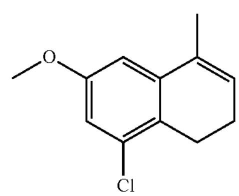 | $^1$H NMR (400 MHz, $CDCl_3$): δ 6.77 (d, J = 2.8 Hz, 1H), 6.73 (d, J = 2.0 Hz, 1H), 5.92 (s, 1H), 3.81 (s, 3H), 2.82 (t, J = 8.0 Hz, 2H), 2.23-2.28 (m, 2H), 2.03 (d, J = 1.6 Hz, 3H). |
| 4-2 | 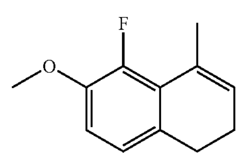 | $^1$H NMR (400 MHz, $CDCl_3$): δ 6.84 (t, J = 8.4 Hz, 1H), 6.74 (t, J = 8.0 Hz, 1H), 5.88-5.90 (m, 1H), 3.87 (s, 3H), 2.64 (t, J = 7.2 Hz, 2H), 2.15-2.22 (m, 5H). |
| 5-2 | 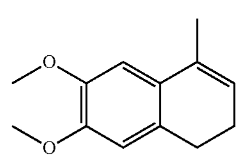 | $^1$H NMR (400 MHz, $CDCl_3$): δ 6.82 (s, 1H), 6.72 (s, 1H), 5.78 (m, 1H), 3.92 (s, 3H), 3.91 (s, 3H), 2.73 (t, J = 8.0 Hz, 2H), 2.27 (ddt, $J_1$ = 2.0 Hz, $J_2$ = 4.4 Hz, $J_3$ = 8.0 Hz, 2H), 2.06 (s, 3H). |
| 6-2 | 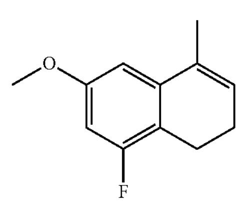 | $^1$H NMR (400 MHz, $CDCl_3$): δ 6.63 (dd, $J_1$ = 2.4 Hz, $J_2$ = 10.0 Hz, 1H), 6.54 (dd, $J_1$ = 2.4 Hz, $J_2$ = 10.8 Hz, 1H), 5.93 (t, J = 4.4 Hz, 1H), 3.84 (s, 3H), 2.75-2.67 (m, 2H), 2.23 (td, $J_1$ = 2.0 Hz, $J_2$ = 6.4 Hz, 2H), 2.03 (q, J = 1.6 Hz, 3H). |

| Compound number | Structure | Spectrogram |
|---|---|---|
| 7-2 | (Br-, OMe substituted dihydronaphthalene with methyl) | ¹H NMR (400 MHz, CDCl₃): δ 7.01 (d, J = 1.6 Hz, 1H), 6.90 (s, 1H), 5.91-5.85 (m, 1H), 3.82 (s, 3H), 2.70 (t, J = 8.0 Hz, 2H), 2.27 (ddt, J₁ = 2.0 Hz, J₂ = 4.4 Hz, J₃ = 8.0 Hz, 2H), 2.01 (s, 3H). |

Step 2: Preparation of Compound 1-3

M-chloroperoxybenzoic acid (4.1 g, 18.96 mmol) was added to a solution of compound 1-2 (4.00 g, 15.80 mmol) in dichloromethane (80 mL) at 0° C. The mixture was stirred at 0° C. for 30 minutes, and then the reaction was quenched by sequential addition of Na₂SO₃ and saturated solution of NaHCO₃ (1:1, 15 mL). The aqueous phase was extracted with dichloromethane (100 mL×3). The combined organic phase was washed with saturated brine (50 mL), dried over anhydrous Na₂SO₄, filtered and concentrated in vacuo to approximately 50 mL. Boron trifluoride etherate complex (0.2 mL) was added to the remaining solution at 0° C. and the mixture was further stirred at 0° C. for 1 hour. After the reaction was quenched by addition of saturated solution of Na₂CO₃ (10 mL), the aqueous phase was extracted with dichloromethane (100 mL×3). The combined organic phase was washed with saturated brine (100 mL), dried over anhydrous Na₂SO₄, filtered and concentrated in vacuo. The residue was purified by silica gel column chromatography (eluent: petroleum ether/ethyl acetate=30/1 to 20/1) to give product 1-3 as a white solid (3.00 g, yield: 70.05%). ¹H NMR (400 MHz, CDCl₃): δ 7.04-7.05 (d, J=2.8 Hz, 1H), 6.74-6.73 (d, J=2.8 Hz, 1H), 3.81 (s, 3H), 3.51 (m, 1H), 3.31-3.29 (m, 1H), 3.11 (m, 1H), 2.64-2.51 (m, 2H), 1.47 (d, J=7.2 Hz, 3H).

The following compounds were synthesized according to a method similar to that of compound 1-3:

| Compound number | Structure | Spectrogram |
|---|---|---|
| 2-3 | (methoxy-tetralone with methyl) | ¹H NMR (400 MHz, CDCl₃): δ 7.15-7.11 (dd, J₁ = 2.8 Hz, J₂ = 2.4 Hz, 1H), 6.77-6.75 (m, 2H), 3.81 (s, 3H), 3.53-3.49 (m, 1H), 3.05-3.01 (m, 2H), 2.64-2.59 (m, 1H), 2.52-2.48 (m, 1H), 1.48-1.46 (d, J = 6.8 Hz, 3H). |
| 3-3 | (methoxy, Cl-substituted tetralone with methyl) | ¹H NMR (400 MHz, CDCl₃): δ 6.85 (d, J = 2.4 Hz, 1H), 6.67 (d, J = 2.0 Hz, 1H), 3.82 (s, 3H), 3.54-3.45 (m, 1H), 3.48-3.25 (m, 1H), 3.24-3.23 (m, 1H), 3.09-3.05 (m, 1H), 2.61-2.45 (m, 2H), 1.45 (d, J = 7.2 Hz, 3H). |
| 4-3 | (methoxy, F-substituted tetralone with methyl) | ¹H NMR (400 MHz, CDCl₃): δ 6.92 (d, J = 8.4 Hz, 1H), 6.83 (t, J = 8.0 Hz, 1H), 3.89 (s, 3H), 3.79-3.75 (m, 1H), 3.18-3.07 (m, 1H), 3.01-2.91 (m, 1H), 2.77-2.73 (m, 1H), 2.52-2.48 (m, 1H), 1.43 (d, J = 7.6 Hz, 3H). |
| 5-3 | (dimethoxy tetralone with methyl) | ¹H NMR (400 MHz, CDCl₃): δ 6.74 (m, 2H), 3.90 (s, 6H), 3.49-3.41 (m, 1H), 3.10-3.05 (m, 2H), 2.65-2.49 (m, 2H), 1.47 (d, J = 7.2 Hz, 3H). |
| 6-3 | (methoxy, F-substituted tetralone with methyl) | ¹H NMR (400 MHz, CDCl₃): δ 6.57-6.48 (m, 2H), 3.79 (s, 3H), 3.49 (d, J = 7.2 Hz, 1H), 3.22-3.05 (m, 1H), 3.03-2.86 (m, 1H), 2.67-2.37 (m, 2H), 1.45 (s 3H). |

| Compound number | Structure | Spectrogram |
|---|---|---|
| 7-3 | 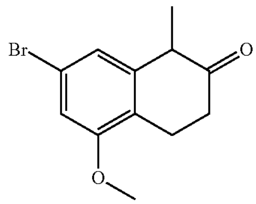 | $^1$H NMR (400 MHz, CDCl$_3$): δ 6.96 (s, 1H), 6.91 (s, 1H), 3.84 (s, 3H), 3.51-3.41 (m, 1H), 3.17-3.10 (m, 1H), 2.96-2.88 (m, 1H), 2.64-2.42 (m, 2H), 1.47 (d, J = 7.2 Hz, 3H). |

Step 3: Preparation of Compound 1-4

Under nitrogen atmosphere, tetrabutylammonium bromide (492.79 mg, 1.86 mmol) was added to a mixture solution of compound 1-3 (5.00 g, 18.58 mmol) and 1,5-dibromopentane (12.82 g, 55.73 mmol) in toluene (50 mL) at 25° C. After the mixture was cooled to 0° C. under an ice bath, 35% aqueous solution of NaOH (36 g, 315.80 mmol) was slowly added dropwise. The reaction mixture was stirred at 0° C. for 2 hours, then warmed to 25° C. and stirred for 14 hours. The aqueous phase was extracted with ethyl acetate (100 mL×3). The combined organic phase was washed with saturated brine (100 mL), dried over anhydrous Na$_2$SO$_4$, filtered and concentrated in vacuo. The residue was purified by silica gel column chromatography (eluent: petroleum ether/ethyl acetate=30/1 to 20/1) to give product 1-4 as a colorless oil (4.50 g, yield: 57.9%). $^1$H NMR (400 MHz, CDCl$_3$): δ 7.07 (d, J=2.4 Hz, 1H), 6.81 (d, J=2.4 Hz, 1H), 3.83 (s, 3H), 3.33 (t, J=6.8 Hz, 2H), 3.26-3.14 (m, 1H), 3.09-2.98 (m, 1H), 2.77-2.65 (m, 1H), 2.65-2.55 (m, 1H), 2.14 (ddd, J$_1$=13.2 Hz, J$_2$=12.0 Hz, J$_3$=4.4 Hz, 1H), 1.76 (quin, J=7.2 Hz, 2H), 1.65 (dd, J$_1$=12.4 Hz, J$_2$=4.4 Hz, 1H), 1.40 (s, 3H), 1.38-1.30 (m, 2H), 1.08-0.83 (m, 2H).

The following compounds were synthesized according to a method similar to that of compound 1-4:

| Compound number | Structure | Spectrogram |
|---|---|---|
| 2-4 | 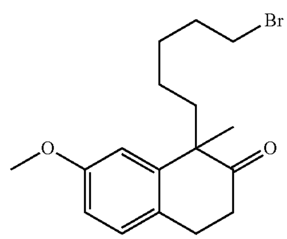 [SMILES: COc1ccc2c(c1)C(C)(CCCCCBr)C(=O)CC2] | $^1$H NMR (400 MHz, CDCl$_3$): δ 7.09 (d, J = 8.4 Hz, 1H), 6.81 (d, J = 2.4 Hz, 1H), 6.76 (dd, J$_1$ = 2.4 Hz, J$_2$ = 8.4 Hz, 1H), 3.82 (s, 3H), 3.31 (t, J = 6.8 Hz, 2H), 3.01-2.96 (m, 2H), 2.73-2.64 (m, 1H), 2.61-2.53 (m, 1H), 2.16-2.06 (m, 1H), 1.74 (quin, J = 7.2 Hz, 2H), 1.68-1.59 (m, 1H), 1.39 (s, 3H), 1.35-1.27 (m, 2H), 1.03-0.88 (m, 2H). |
| 3-4 | 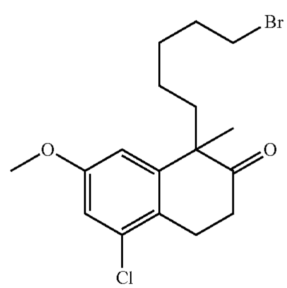 [SMILES: COc1cc(Cl)c2c(c1)C(C)(CCCCCBr)C(=O)CC2] | $^1$H NMR (400 MHz, CDCl$_3$): δ 6.87 (d, J = 2.4 Hz, 1H), 6.74 (d, J = 2.4 Hz, 1H), 3.84 (s, 3H), 3.41-3.29 (m, 1H), 3.24-3.10 (m, 1H), 3.05-2.95 (m, 1H), 2.70-2.50 (m, 2 H), 2.15-2.05 (m, 1H), 1.79-1.50 (m, 3H), 1.41-1.24 (m, 5H), 1.00-0.83 (m, 2H). |
| 4-4 | 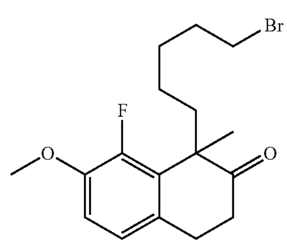 [SMILES: COc1ccc2c(c1F)C(C)(CCCCCBr)C(=O)CC2] | $^1$H NMR (400 MHz, CDCl$_3$): δ 6.93-6.80 (m, 2H), 3.89 (s, 3H), 3.31 (t, J = 7.2 Hz, 2H), 3.04-2.88 (m, 2H), 2.82-2.71 (m, 1H), 2.58-2.50 (m, 1H), 2.25-2.21 (m, 1H), 2.08-1.94 (m, 1H), 1.74 (m, 2H), 1.51 (s, 3H), 1.44-1.25 (m, 2H), 1.05-0.98 (m, 1H), 0.87-0.73 (m, 1H). |

| Compound number | Structure | Spectrogram |
|---|---|---|
| 5-4 | 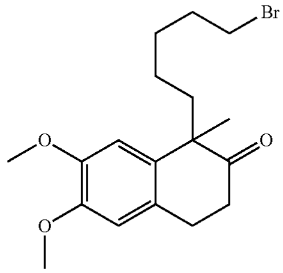 [SMILES: COc1cc2c(cc1OC)C(C)(CCCCCBr)C(=O)CC2] | $^1$H NMR (400 MHz, CDCl$_3$): δ 6.74 (s, 1H), 6.65 (s, 1H), 3.89 (s, 6H), 3.31 (t, J = 6.8 Hz, 2H), 3.05-2.95 (m, 2H), 2.72-2.57 (m, 2H), 2.14 (ddd, J$_1$ = 13.2 Hz, J$_2$ = 12.0 Hz, J$_3$ = 4.4 Hz, 1H), 1.80-1.7 (m, 2H), 1.65-1.55 (m, 1H), 1.49-1.25 (m, 5H), 1.08-0.83 (m, 2H). |
| 6-4 | 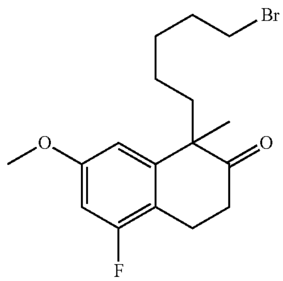 [SMILES: COc1cc(F)c2c(c1)C(C)(CCCCCBr)C(=O)CC2] | $^1$H NMR (400 MHz, CDCl$_3$): δ 6.68-6.47 (m, 2H), 3.83 (s, 3H), 3.33 (t, J = 6.8 Hz, 2H), 3.06 (s, 1H), 2.97-2.83 (m, 1H), 2.73-2.48 (m, 2H), 2.13 (dd, J$_1$ = 4.8 Hz, J$_2$ = 13.2 Hz, 1H), 1.82-1.71 (m, 2H), 1.69-1.59 (m, 1H), 1.41 (s, 3H), 1.30 (s, 2H), 1.09-0.83 (m, 2H). |
| 7-4 | 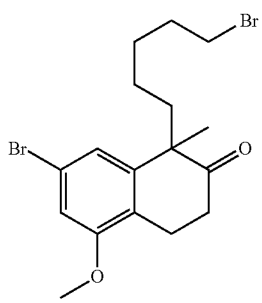 [SMILES: COc1cc(Br)cc2c1CCC(=O)C2(C)CCCCCBr] | $^1$H NMR (400 MHz, CDCl$_3$): δ 6.98 (s, 1H), 6.84 (s, 1H), 3.80 (s, 3H), 3.26 (t, J = 6.8 Hz, 2H), 3.10-3.01 (m, 1H), 2.81-2.75 (m, 1H), 2.65-2.45 (m, 2H), 2.14 (ddd, J$_1$ = 13.2 Hz, J$_2$ = 12.0 Hz, J$_3$ = 4.4 Hz, 1H), 1.80-1.6 (m, 3H), 1.40 (s, 3H), 1.38-1.30 (m, 2H), 1.08-0.83 (m, 2H). |
| 8-1 | 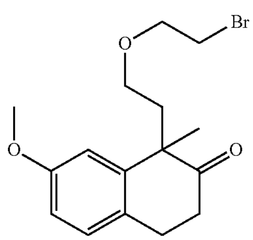 [SMILES: COc1ccc2c(c1)C(C)(CCOCCBr)C(=O)CC2] | $^1$H NMR (400 MHz, CDCl$_3$): δ 7.10 (d, J = 8.4 Hz, 1H), 6.82-6.75 (m, 2H), 3.82 (s, 3H), 3.60-3.34 (m, 2H), 3.33-3.31 (m, 2H), 3.23-3.20 (m, 2H), 3.10-3.00 (m, 1H), 3.00-2.90 (m, 1H), 2.75-2.66 (m, 2H), 2.66-2.54 (m, 1H), 1.92-1.87 (m, 1H), 1.43 (s, 3H). |

Step 4: Preparation of Compound 1-5

Under nitrogen atmosphere, NaH (60% wt, 688.6 mg, 17.23 mmol) was added to a solution of compound 1-4 (4.00 g, 9.57 mmol) in DMF (80 mL) at 25° C. The reaction mixture was stirred at room temperature for 10 minutes, then heated to 60° C. and stirred for 1 hour. After being cooled to room temperature, the reaction solution was poured into ice water (400 mL). The aqueous phase was extracted with ethyl acetate (400 mL×3). The combined organic phase was washed with saturated brine (300 mL), dried over anhydrous Na$_2$SO$_4$, filtered and concentrated in vacuo. The residue was purified by silica gel column chromatography (eluent: petroleum ether/ethyl acetate=30/1 to 20/1) to give product 1-5 (1.50 g, yield: 46.48%). $^1$H NMR (400 MHz, CDCl$_3$): δ 7.06 (d, J=2.4 Hz, 1H), 6.81 (d, J=2.4 Hz, 1H), 3.82 (s, 3H), 3.26 (dd, J$_1$=4.4 Hz, J$_2$=16.8 Hz, 1H), 3.08-2.99 (m, 1H), 2.79 (dd, J$_1$=4.0 Hz, J$_2$=9.6 Hz, 1H), 2.45-2.35 (m, 1H), 1.94-1.83 (m, 1H), 1.82-1.72 (m, 2H), 1.70-1.48 (m, 4H), 1.42-1.30 (m, 5H).

The following compounds were synthesized according to a method similar to that of compound 1-5:

| Compound number | Structure | Spectrogram |
|---|---|---|
| 2-5 | 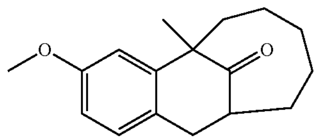 [SMILES: COc1ccc2c(c1)C1(C)CCCCCC(C2)C1=O] | $^1$H NMR (400 MHz, CDCl$_3$): δ 7.07 (d, J = 8.0 Hz, 1H), 6.81 (d, J = 2.4 Hz, 1H), 6.74 (dd, J$_1$ = 2.4 Hz, J$_2$ = 8.0 Hz, 1H), 3.85-3.79 (m, 3H), 3.08-2.97 (m, 2H), 2.76 (qd, J$_1$ = 5.2 Hz, J$_2$ = 9.6 Hz, 1H), 2.48-2.36 (m, 1H), 1.95-1.85 (m, 1H), 1.79-1.70 (m, 2H), 1.65-1.50 (m, 4H), 1.37 (s, 3H), 1.34-1.24 (m, 2H). |
| 3-5 | 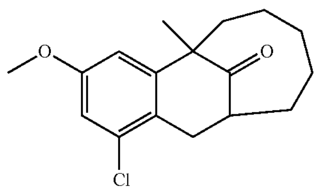 [SMILES: COc1cc(Cl)c2c(c1)C1(C)CCCCCC(C2)C1=O] | $^1$H NMR (400 MHz, CDCl$_3$): δ 6.85 (d, J = 2.0 Hz, 1H), 6.74 (d, J = 2.8 Hz, 1H), 3.21 (dd, J$_1$ = 17.2 Hz, J$_2$ = 4.8 Hz, 1H), 3.01 (dd, J$_1$ = 16.4 Hz, J$_2$ = 5.6 Hz, 1H), 2.79-2.70 (m, 1H), 2.45-2.30 (m, 1H), 1.95-1.70 (m, 3H), 1.64-1.45 (m, 3H), 1.29-1.26 (m, 5H). |
| 4-5 | 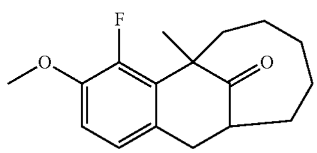 [SMILES: COc1ccc2c(c1F)C1(C)CCCCCC(C2)C1=O] | MS (m/z): 276.9 (M + 1). |
| 5-5 | 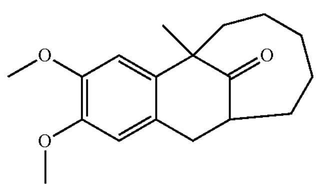 [SMILES: COc1cc2c(cc1OC)C1(C)CCCCCC(C2)C1=O] | $^1$H NMR (400 MHz, CDCl$_3$): δ 6.73 (s, 1H), 6.64 (s, 1H), 3.88 (s, 6H), 3.12-3.03 (m, 1H), 2.98-2.90 (m, 1H), 2.81-2.72 (m, 1H), 2.41-2.29 (m, 1H), 2.00-1.86 (m, 1H), 1.82-1.71 (m, 2H), 1.66-1.47 (m, 4H), 1.36 (s, 3H), 1.35-1.28 (m, 2H), 0.92-0.81 (m, 1H). |
| 6-5 | 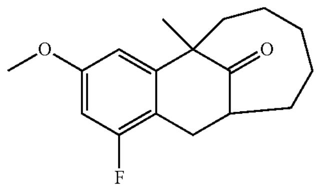 [SMILES: COc1cc(F)c2c(c1)C1(C)CCCCCC(C2)C1=O] | MS (m/z): 277.0 (M + 1). |
| 7-5 | 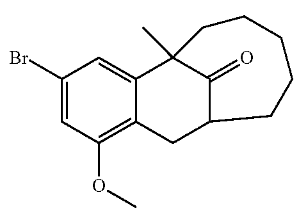 [SMILES: COc1cc(Br)cc2c1CC1CCCCCC2(C)C1=O] | $^1$H NMR (400 MHz, CDCl$_3$): δ ☐ 7.03 (d, J = 1.6 Hz, 1H), 6.90 (d, J = 1.6 Hz, 1H), 3.85 (s, 3H), 3.15 (dd, J$_1$ = 3.6 Hz, J$_2$ = 17.6 Hz, 1H), 2.87-2.75 (m, 2H), 2.40-2.30 (m, 1H), 1.94-1.72 (m, 3H), 1.70-1.48 (m, 4H), 1.42-1.30 (m, 5H). |
| 8-2 | 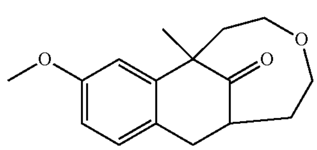 | $^1$H NMR (400 MHz, CDCl$_3$): δ 7.09 (d, J = 8.4 Hz, 1H), 6.82 (d, J = 2.4 Hz, 1H), 6.78-6.75 (m, 1H), 3.82 (s, 3H), 3.80-3.71 (m, 2H), 3.49-3.46 (m, 1H), 3.35-3.25 (m, 1H), 3.08-3.06 (m, 1H), 3.00-2.98 (m, 1H), 2.98-2.84 (m, 1H), 2.50-2.43 (m, 1H), 2.12-2.08 (m, 2H), 2.05-1.90 (m, 1H), 1.40 (s, 3H). |

Step 5: Preparation of Compound 1-6

Under nitrogen atmosphere, the mixed solution of compound 1-5 (400.00 mg, 1.19 mmol), MeB(OH)$_2$ (142.47 mg, 2.38 mmol), K$_2$CO$_3$ (493.41 mg, 3.57 mmol) and Pd(dppf)Cl$_2$ (87.07 mg, 119.00 umol) in dioxane (8 mL) was heated to 100° C. and the mixture was stirred for 2 hours. After being cooled down, the reaction solution was diluted with 50 mL water. The aqueous phase was extracted with ethyl acetate (50 mL×3). The combined organic phase was washed with saturated brine (30 mL), dried over anhydrous Na$_2$SO$_4$, filtered and concentrated in vacuo. The residue was purified by silica gel column chromatography (eluent: petroleum ether/ethyl acetate=20/1) to give product 1-6 as a yellow oil (250.00 mg, yield 77.13%). $^1$H NMR (400 MHz, CDCl$_3$): δ 6.66 (m, 2H), 3.80 (s, 3H), 2.94 (dq, J$_1$=5.2 Hz, J$_2$=16.4 Hz, 2H), 2.76 (dd, J$_1$=4.4 Hz, J$_2$=9.6 Hz, 1H), 2.40 (ddd, J$_1$=2.0 Hz, J$_2$=8.0 Hz, J$_3$=14.4 Hz, 1H), 2.28 (s, 3H), 1.98-1.85 (m, 1H), 1.81-1.67 (m, 2H), 1.65-1.46 (m, 3H), 1.41-1.29 (m, 5H).

The following compounds were synthesized according to a method similar to that of compound 1-6:

| Compound number | Structure | Spectrogram |
|---|---|---|
| 9-1 | 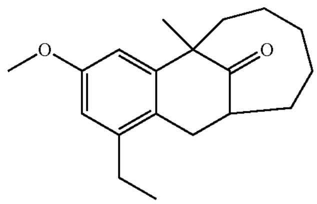 [SMILES: CCc1cc(OC)cc2c1CC1CCCCCC2(C)C1=O] | $^1$H NMR (400 MHz, CDCl$_3$): δ 6.71-6.63 (m, 2H), 3.08-2.98 (m, 1H), 2.94 (d, J = 5.6 Hz, 1H), 2.76 (d, J = 5.2 Hz, 1H), 2.63 (dd, J$_1$ = 4.0 Hz, J$_2$ = 7.6 Hz, 2H), 2.40 (br. s., 1H), 2.00-1.82 (m, 1H), 1.81-1.66 (m, 3H), 1.65-1.44 (m, 5H), 1.39-1.29 (m, 6H), 1.20 (t, J = 7.6 Hz, 3H). |
| 10-1 | 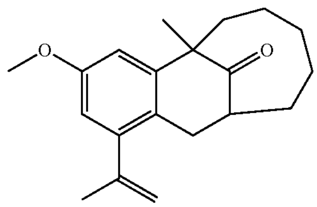 [SMILES: C=C(C)c1cc(OC)cc2c1CC1CCCCCC2(C)C1=O] | $^1$H NMR (400 MHz, CDCl$_3$): δ 6.76 (d, J = 2.4 Hz, 1H), 6.63 (d, J = 2.4 Hz, 1H), 5.22 (s, 1H), 4.86 (s, 1H), 3.83 (s, 3H), 3.08-2.95 (m, 2H), 2.75 (m, 1H), 2.48 (m, 1H), 2.03 (s, 3H), 1.87 (m, 2H), 1.84-1.59 (m, 6H), 1.39- 1.29 (m, 7H). |
| 11-1 | 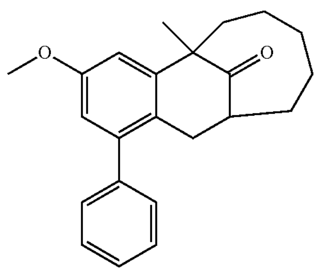 [SMILES: COc1cc(-c2ccccc2)c2c(c1)C1(C)CCCCCC(C2)C1=O] | $^1$H NMR (400 MHz, CDCl$_3$): δ 7.46-7.40 (m, 2H), 7.39-7.34 (m, 1H), 7.33-7.28 (m, 2H), 6.86 (d, J = 2.8 Hz, 1H), 6.73 (d, J = 2.8 Hz, 1H), 3.83 (s, 3H), 2.93-2.87 (m, 2H), 2.69-2.60 (m, 1H), 2.57-2.47 (m, 1H), 1.90-1.72 (m, 2H), 1.69-1.45 (m, 6H), 1.45- 1.41 (m, 3H), 1.41-1.22 (m, 2H). |

Step 6: Preparation of Compound 1-7

The mixed solution of compound 1-6 (250.00 mg, 0.92 mmol) and NH$_2$OH—HCl 63.78 mg, 0.92 mmol) in pyridine (8 mL) was heated at reflux for 24 hours. After being cooled to 25° C., the reaction solution was poured into ice water (100 mL). The aqueous phase was acidified with dilute hydrochloric acid (1M) and extracted with dichloromethane (100 mL×3). The combined organic phase was washed with saturated brine (100 mL), dried over anhydrous Na$_2$SO$_4$, filtered and concentrated in vacuo. The residue was recrystallized from ethyl acetate to give product 1-6 (118.00 mg, yield 44.73%). $^1$H NMR (400 MHz, CDCl$_3$): 6.75 (d, J=2.8 Hz, 1H), 6.64 (d, J=2.4 Hz, 1H), 3.81 (s, 3H), 3.76 (d, J=7.2 Hz, 1H), 2.92-2.77 (m, 2H), 2.36-2.30 (m, 1H), 2.28 (s, 3H), 2.15-2.03 (m, 1H), 1.69-1.55 (m, 8H), 1.54 (s, 3H).

The following compounds were synthesized according to a method similar to that of compound 1-7:

| Compound number | Structure | Spectrogram |
|---|---|---|
| 2-6 | 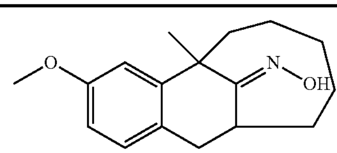 | $^1$H NMR (400 MHz, CDCl$_3$): δ 7.05-7.03 (d, J = 8.0 Hz, 1H), 6.85-6.83 (d, J = 2.4 Hz, 1H), 6.73-6.70 (dd, J$_1$ = 2.8 Hz, J$_2$ = 2.8 Hz, 1H), 3.80 (s, 3H), 3.80-3.73 (m, 1H), 3.01-2.96 (m, 1H), 2.89-2.83 (m, 1H), 2.32-2.31 (m, 1H), 2.09-2.05 (m, 1H), 1.80-1.70 (m, 1H), 1.62- 1.57 (m, 5H), 1.55 (s, 3H). |
| 3-6 | 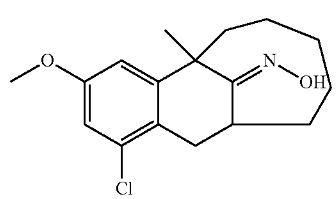 | MS (m/z): 307.9 (M + 1). |
| 4-6 | 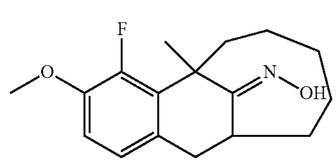 [SMILES: COc1ccc2c(c1F)C1(C)CCCCCC(C2)/C1=N\O] | MS (m/z): 292.1 (M + 1). |

-continued

| Compound number | Structure | Spectrogram |
|---|---|---|
| 5-6 | 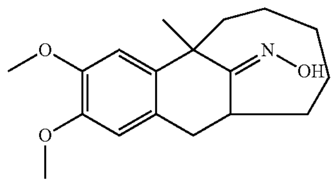 [SMILES: COc1cc2c(cc1OC)C1(C)CCCCCC(C2)/C1=N\O] | MS (m/z): 304.1 (M + 1). |
| 6-6 | 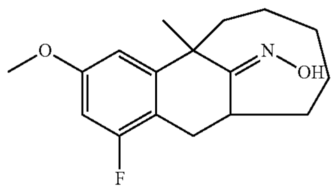 [SMILES: COc1cc(F)c2c(c1)C1(C)CCCCCC(C2)/C1=N\O] | ¹H NMR (400 MHz, CDCl₃): δ 6.68 (d, J = 1.6 Hz, 1H), 6.51 (dd, J₁ = 2.4 Hz, J₂ = 11.2 Hz, 1H), 3.80 (m, 4H), 3.01-2.79 (m, 2H), 2.35-2.21 (m, 1H), 2.16-2.02 (m, 1H), 1.68-1.55 (m, 12H), 1.53 (s, 3H). |
| 8-3 | 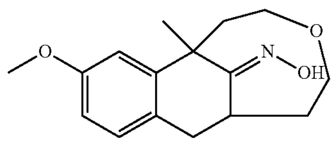 | MS (m/z): 276.0 (M + 1). |
| 9-2 | 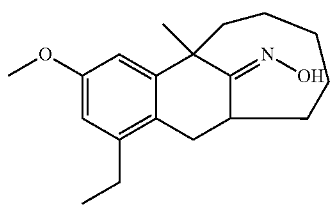 [SMILES: CCc1cc(OC)cc2c1CC1CCCCCC2(C)/C1=N/O] | ¹H NMR (400 MHz, CDCl₃): δ 6.74 (d, J = 2.4 Hz, 1H), 6.63 (d, J = 2.4 Hz, 1H), 3.80 (s, 3H), 3.77-3.67 (m, 1H), 3.11-2.92 (m, 1H), 2.88 (dd, J₁ = 4.4 Hz, J₂ = 7.2 Hz, 2H), 2.62 (q, J = 7.6 Hz, 2H), 2.38-2.22 (m, 1H), 1.58 (m, 11H), 1.19 (t, J = 7.6 Hz, 3H). |
| 10-2 | 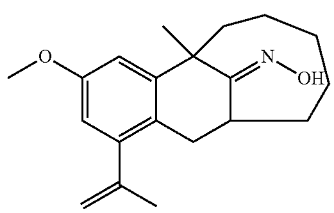 [SMILES: C=C(C)c1cc(OC)cc2c1CC1CCCCCC2(C)/C1=N/O] | MS (m/z): 314.0 (M + 1). |
| 11-2 | 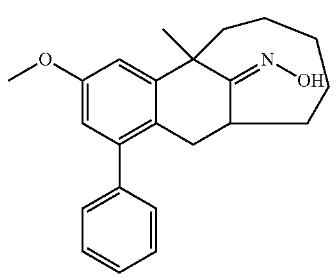 [SMILES: COc1cc(-c2ccccc2)c2c(c1)C1(C)CCCCCC(C2)/C1=N\O] | MS (m/z): 349.9 (M + 1). |

Step 7: Preparation of Compound 1-8

Under nitrogen atmosphere, Raney-Ni (0.5 g, 50% wt) was added to a solution of compound 1-7 (100.00 mg, 347.95 umol) in ethanol (15 mL). The reaction system was evacuated and purged with H₂ for three times. Then the reaction solution was heated to 70° C. under H₂ atmosphere (50 psi) and stirred for 48 hours. The reaction mixture was filtered under suction and the filtrate was concentrated in vacuo to give crude product 1-8 (80 mg) which was used directly in the next step without further purification. MS (m/z): 274.0 (M+1).

The following compounds were synthesized according to a method similar to that of compound 1-8:

| Compound number | Structure | Spectrogram |
|---|---|---|
| 2-7 | 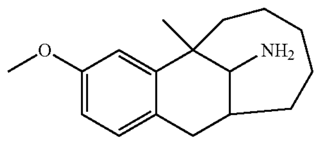 [SMILES: COc1ccc2c(c1)C1(C)CCCCCC(C2)C1N] | $^1$H NMR (400 MHz, CDCl$_3$): δ 7.01-6.99 (d, J = 8.8 Hz, 1H), 6.79-6.78 (d, J = 2.8 Hz, 1H), 6.73-6.70 (dd, J$_1$ = 2.4 Hz, J$_2$ = 2.8 Hz, 1H), 3.77 (s, 3H), 3.15-3.08 (m, 2H), 2.70-2.66 (d, J = 16.4 Hz, 1H), 2.29-2.21 (m, 1H), 2.03-1.95 (m, 1H), 1.78-1.75 (m, 3H), 1.53-1.37 (m, 4H), 1.37 (s, 3H), 1.11-1.08 (m, 1H), 0.90-0.83 (m, 2H). |
| 3-7 | 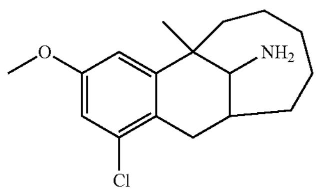 [SMILES: COc1cc(Cl)c2c(c1)C1(C)CCCCCC(C2)C1N] | MS (m/z): 294.0 (M + 1). |
| 4-7 | 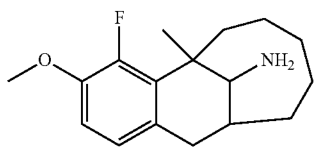 [SMILES: COc1ccc2c(c1F)C1(C)CCCCCC(C2)C1N] | $^1$H NMR (400 MHz, CDCl$_3$): δ 6.84-6.78 (m, 2H), 3.86 (s, 3H), 3.19-3.09 (m, 2H), 2.71-2.65 (m, 1H), 2.24-2.15 (m, 1H), 2.09-1.95 (m, 2H), 1.90-1.45 (m, 9H), 1.31-1.20 (m, 1H), 0.98-0.79 (m, 3H). |
| 5-7 | 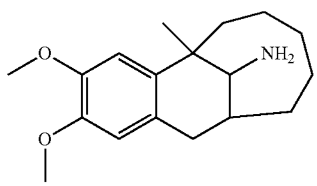 [SMILES: COc1cc2c(cc1OC)C1(C)CCCCCC(C2)C1N] | MS (m/z): 289.9 (M + 1). |
| 6-7 | 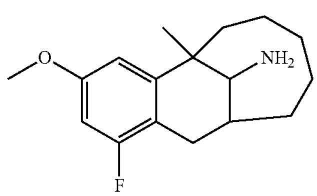 [SMILES: COc1cc(F)c2c(c1)C1(C)CCCCCC(C2)C1N] | MS (m/z): 278.2 (M + 1). |
| 8-4 | 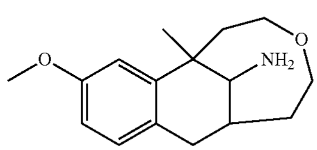 [SMILES: COc1ccc2c(c1)C1(C)CCOCCC(C2)C1N] | $^1$H NMR (400 MHz, CDCl$_3$): δ 6.99 (d, J = 8.4 Hz, 1H), 6.80 (d, J = 2.4 Hz, 1H). 6.72-6.69 (m, 1H), 3.81-3.78 (m, 4H), 3.68-3.65 (m, 1H), 3.31-3.25 (m, 1H), 3.12-3.06 (m, 3H), 2.60-2.56 (m, 1H), 2.26-2.23 (m, 2H), 2.05 (brs, 2H), 1.74-1.71 (m, 3H), 1.34 (s, 3H). |
| 9-3 | 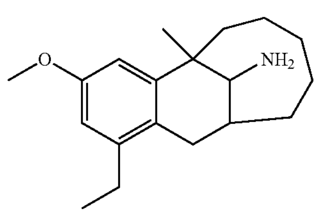 [SMILES: CCc1cc(OC)cc2c1CC1CCCCCC2(C)C1N] | MS (m/z): 289.1 (M + 1). |
| 10-3 | 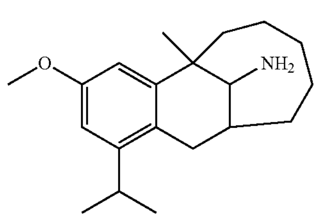 [SMILES: COc1cc(C(C)C)c2c(c1)C1(C)CCCCCC(C2)C1N] | MS (m/z): 302.0 (M + 1). |

| Compound number | Structure | Spectrogram |
|---|---|---|
| 11-3 | 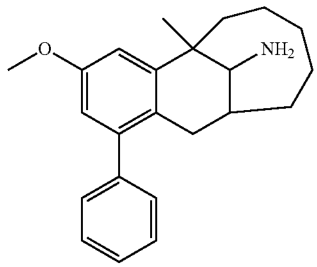 [SMILES: COc1cc(-c2ccccc2)c2c(c1)C1(C)CCCCCC(C2)C1N] | MS (m/z): 336.1 (M + 1). |

Step 8: Preparation of Compound 1

The mixture of crude compound 1-8 (80.00 mg) and aqueous hydrobromic acid (5 mL, 48% wt) was heated to 100° C. and stirred for 1 hour. After being cooled to room temperature, the reaction mixture was concentrated in vacuo. The residue was purified by HPLC preparative column to give product 1 (50 mg, two-step yield: 55.39%). $^1$H NMR (400 MHz, CD$_3$OD): δ 6.58 (s, 1H), 3.65 (d, J=5.2 Hz, 1H), 2.99-2.89 (m, 1H), 2.81-2.70 (m, 1H), 2.57 (d, J=5.2 Hz, 1H), 2.23 (s, 3H), 2.02-1.88 (m, 2H), 1.80-1.64 (m, 2H), 1.64-1.50 (m, 3H), 1.46 (s, 3H), 1.20 (d, J=12.0 Hz, 1H), 1.04-0.78 (m, 2H). MS (m/z): 260.0 (M+1).

Compounds 2~6 and Compounds 8~11 were prepared according to method of Compound 1:

| Compound number | Structure | Spectrogram |
|---|---|---|
| Compound 2 (Reference compound) | 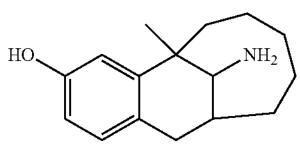 [SMILES: CC12CCCCCC(Cc3ccc(O)cc31)C2N] | $^1$H-NMR (CD$_3$OD, 400 MHz): δ 6.90-6.88 (d, J = 8.0 Hz, 1H), 6.68 (s, 1H), 6.58-6.55 (d, J = 8.4 Hz, 1H), 3.13-3.07 (m, 2H), 2.66-2.62 (d, J = 16.4 Hz, 1H), 2.28-2.24 (m, 1H), 1.96-1.93 (m, 1H), 1.77-1.73 (m, 3H), 1.54-1.50 (m, 1H), 1.49-1.46 (m, 2H), 1.34 (s, 3H), 1.09-1.07 (m, 1H), 0.93-0.90 (m, 2H). MS (m/z): 246.1 (M + 1). |
| Compound 3 | 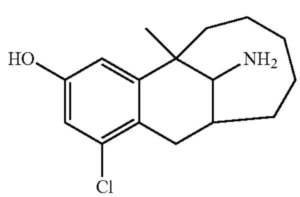 [SMILES: CC12CCCCCC(Cc3c(Cl)cc(O)cc31)C2N] | $^1$H NMR (CD$_3$OD, 400 MHz): δ 6.79 (d, J = 2.4 Hz, 1H), 6.68 (d, J = 2.0 Hz, 1H), 3.64-3.63 (m, 1H), 3.05-2.90 (m, 2H), 2.58-2.50 (m, 1H), 2.02-1.91 (m, 2H), 1.70-1.45 (m, 8H), 1.20-1.17 (m, 1H), 0.92-0.82 (m, 2H). MS (m/z): 280.1 (M + 1). |
| Compound 4 | 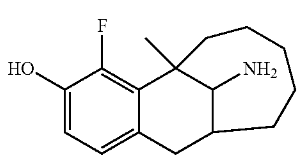 [SMILES: CC12CCCCCC(Cc3ccc(O)c(F)c31)C2N] | $^1$H NMR (400 MHz, CD$_3$OD): δ 6.85-6.79 (m, 2H), 3.65-3.63 (m, 1H), 3.26-3.20 (m, 2H), 2.80-2.76 (m, 1H), 2.45-2.35 (m, 1H), 2.26-2.19 (m, 1H), 2.04-1.96 (m, 1H), 1.71-1.45 (m, 7H), 1.25-1.14 (m, 1H), 0.91-0.80 (m, 2H). MS (m/z): 263.9 (M + 1). |
| Compound 5 | 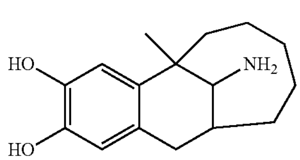 | $^1$H NMR (400 MHz, CD$_3$OD): δ 6.67 (s, 1H), 6.54 (s, 1H), 3.62 (d, J = 5.2 Hz, 1H), 3.17 (dd, J$_1$ = 7.2 Hz, J$_2$ = 16.8 Hz, 1H), 2.65 (d, J = 16.8 Hz, 1H), 2.46 (br. s., 1H), 2.05-1.82 (m, 2H), 1.77-1.64 (m, 2H), 1.63-1.48 (m, 3H), 1.44 (s, 3H), 1.19 (d, J = 11.6 Hz, 1H), 1.08-0.84 (m, 2H). MS (m/z): 262.0 (M + 1). |
| Compound 6 | 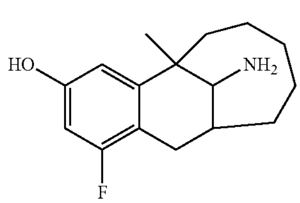 [SMILES: CC12CCCCCC(Cc3c(F)cc(O)cc31)C2N] | $^1$H NMR (400 MHz, CD$_3$OD): δ 6.56 (s, 1H), 6.36 (dd, J$_1$ = 2.4 Hz, J$_2$ = 11.2 Hz, 1H), 3.67 (d, J = 5.2 Hz, 1H), 2.95-2.80 (m, 2H), 2.60-2.51 (m, 1H), 2.05-1.91 (m, 2H), 1.84-1.55 (m, 5H), 1.48 (s, 3H), 1.28-1.15 (m, 1H), 1.02-0.80 (m, 2H). MS (m/z): 264.0 (M + 1). |

| Compound number | Structure | Spectrogram |
|---|---|---|
| Compound 8 | 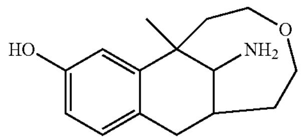 [SMILES: CC12CCOCCC(Cc3ccc(O)cc31)C2N] | $^1$H NMR (400 MHz, CD$_3$OD): δ 6.95 (d, J = 8.4 Hz, 1H), 6.77 (d, J = 2.8 Hz, 1H), 6.65-6.63 (m, 1H), 3.77-3.74 (m, 2H), 3.60-3.55 (m, 2H), 3.40-3.30 (m, 1H), 3.09-3.04 (m, 1H), 2.70-2.66 (m, 1H), 2.45-2.35 (m, 1H), 2.18-2.14 (m, 1H), 2.03-1.99 (m, 2H), 1.63-1.62 (m, 1H), 1.39 (s, 3H). MS (m/z): 248.0 (M + 1). |
| Compound 9 | 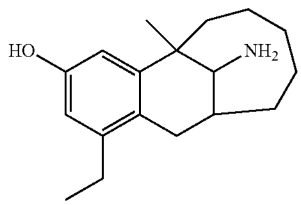 [SMILES: CCc1cc(O)cc2c1CC1CCCCCC2(C)C1N] | $^1$H NMR (400 MHz, CD$_3$OD): δ 6.59 (d, J = 1.6 Hz, 1H), 3.66 (d, J = 5.2 Hz, 1H), 3.06-2.94 (m, 1H), 2.91-2.80 (m, 1H), 2.70-2.48 (m, 3H), 2.04-1.90 (m, 2H), 1.79-1.65 (m, 2H), 1.64-1.50 (m, 3H), 1.47 (s, 3H), 1.22 (t, J = 7.6 Hz, 4H), 1.06-0.78 (m, 2H). MS (m/z): 274.0 (M + 1). |
| Compound 10 | 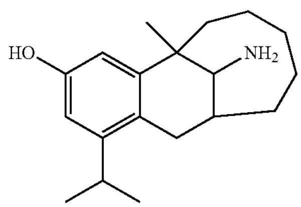 [SMILES: CC(C)c1cc(O)cc2c1CC1CCCCCC2(C)C1N] | $^1$H NMR (400 MHz, CD$_3$OD): δ 6.69 (d, J = 2.4 Hz, 1H), 6.57 (d, J = 2.4 Hz, 1H), 3.66 (d, J = 5.2 Hz, 1H), 3.17 (quin, J = 6.8 Hz, 1H), 3.08-2.86 (m, 2H), 2.55 (br. s., 1H), 2.06-1.87 (m, 2H), 1.80-1.65 (m, 2H), 1.64-1.49 (m, 3H), 1.47 (s, 3H), 1.23 (t, J = 6.4 Hz, 7H), 1.08-0.82 (m, 2H). MS (m/z): 288.0 (M + 1). |
| Compound 11 | 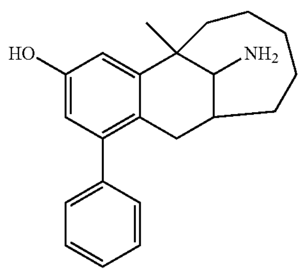 [SMILES: CC12CCCCCC(Cc3c(-c4ccccc4)cc(O)cc31)C2N] | $^1$H NMR (400 MHz, CD$_3$OD): δ 7.47-7.39 (m, 2H), 7.39-7.32 (m, 1H), 7.26 (d, J = 6.8 Hz, 2H), 6.77 (d, J = 2.4 Hz, 1H), 6.58 (d, J = 2.4 Hz, 1H), 3.70 (d, J = 5.2 Hz, 1H), 2.98 (dd, J$_1$ = 7.2 Hz, J$_2$ = 17.2 Hz, 1H), 2.53 (d, J = 17.2 Hz, 1H), 2.39 (br. s., 1H), 2.06-1.96 (m, 1H), 1.85-1.69 (m, 2H), 1.67-1.57 (m, 3H), 1.55 (s, 3H), 1.53-1.42 (m, 1H), 1.21 (d, J = 10.4 Hz, 1H), 1.10-0.84 (m, 2H). |

Example 7: Preparation of Compound 7

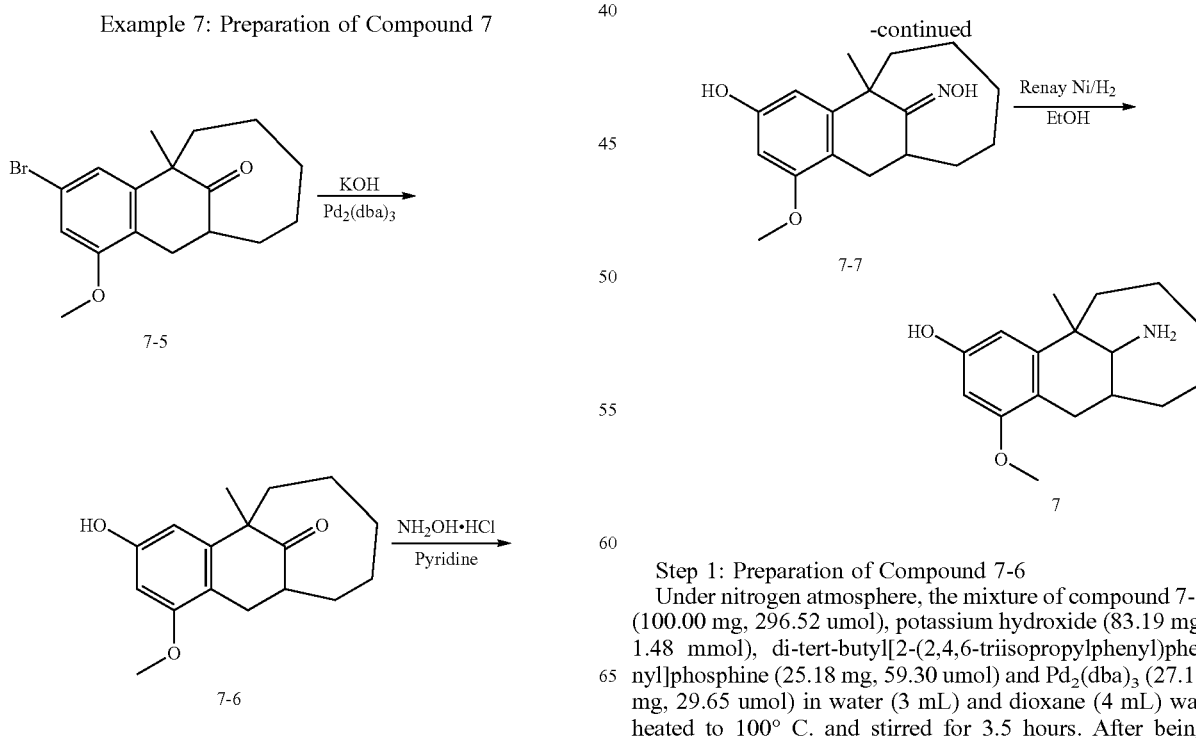

Step 1: Preparation of Compound 7-6

Under nitrogen atmosphere, the mixture of compound 7-5 (100.00 mg, 296.52 umol), potassium hydroxide (83.19 mg, 1.48 mmol), di-tert-butyl[2-(2,4,6-triisopropylphenyl)phenyl]phosphine (25.18 mg, 59.30 umol) and Pd$_2$(dba)$_3$ (27.15 mg, 29.65 umol) in water (3 mL) and dioxane (4 mL) was heated to 100° C. and stirred for 3.5 hours. After being cooled down, the reaction solution was diluted by 20 mL water. The aqueous phase was extracted with ethyl acetate (30 mL×3). The combined organic phase was washed with saturated brine (30 mL), dried over anhydrous Na$_2$SO$_4$, filtered and concentrated in vacuo. The residue was purified by silica gel column chromatography (eluent: petroleum ether/ethyl acetate=10/1 to 5/1) to give 7-6 (60.00 mg, yield 73.76%). $^1$H NMR (400 MHz, CDCl$_3$): δ 6.35 (dd, J=2.0 Hz, J$_2$=12.4 Hz, 1H), 3.83 (s, 3H), 3.52 (s, 1H), 3.10 (dd, J=4.0 Hz, J$_2$=16.8 Hz, 1H), 2.91-2.81 (m, 1H), 2.75 (dd, J=4.0 Hz, J$_2$=9.6 Hz, 1H), 2.44-2.32 (m, 1H), 1.99-1.85 (m, 1H), 1.82-1.69 (m, 2H), 1.68-1.48 (m, 5H), 1.44-1.24 (m, 5H).

Step 2: Preparation of Compound 7-7

The mixed solution of compound 7-6 (70.00 mg, 255.15 umol) and NH$_2$OH—HCl (88.65 mg, 1.28 mmol) in pyridine (5 mL) was heated at reflux for 24 hours. After being cooled to 25° C., the reaction mixture was poured into ice water (20 mL). The aqueous phase was acidified with dilute hydrochloric acid (1M) and extracted with dichloromethane (20 mL×3). The combined organic phase was washed with saturated brine (20 mL), dried over anhydrous Na$_2$SO$_4$, filtered and concentrated in vacuo to give crude product 7-7 (68 mg). MS (m/z): 290.0 (M+1).

Step 3: Preparation of Compound 7

Under nitrogen atmosphere, Raney-Ni (1.00 g) was added to a solution of compound 7-7 (78.00 mg, 269.55 umol) in ethanol (20 mL). The reaction system was evacuated and purged with H$_2$ for three times. Then the reaction solution was heated to 70° C. under H$_2$ atmosphere and stirred for 48 hours. The reaction mixture was filtered under suction and the filtrate was concentrated in vacuo. The residue was purified by silica gel column chromatography (eluent: petroleum ether/ethyl acetate=1/1) to give 7 (30.00 mg, yield 40.42%). $^1$H NMR (400 MHz, CD$_3$OD): δ 6.33 (s, 1H), 3.81 (s, 2H), 3.67-3.56 (m, 1H), 2.91 (s, 1H), 2.84-2.70 (m, 1H), 2.56-2.41 (m, 1H), 2.00-1.85 (m, 2H), 1.77-1.47 (m, 5H), 1.45 (s, 3H), 1.19 (d, J=12.4 Hz, 1H), 1.03-0.79 (m, 2H). MS (m/z): 276.1 (M+1).

Example 12: Preparation of Compound 12

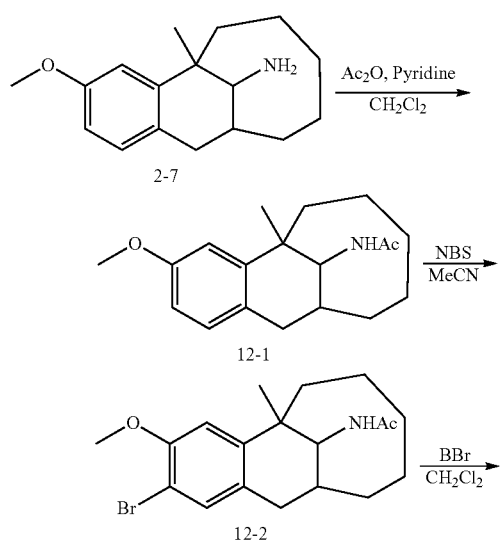

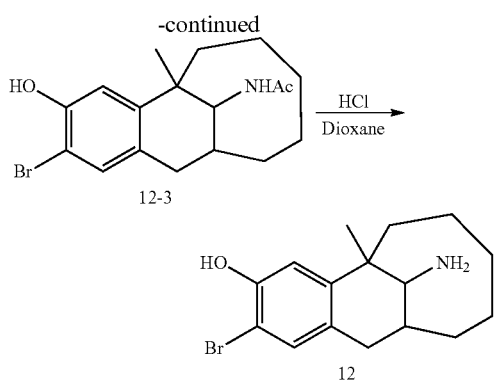

Step 1: Preparation of Compound 12-1

Ac$_2$O (1142 mg, 8.525 mmol) was added dropwise to a solution of compound 2-7 (552 mg, 2.131 mmol) in pyridine (15 mL) at room temperature. Then, the reaction solution was stirred at room temperature for 12 hours. After the reaction was complete, the reaction solution was poured into 100 mL water and extracted with ethyl acetate (100 mL×3). The combined organic phase was washed with saturated brine (50 mL), dried over anhydrous Na$_2$SO$_4$, filtered and concentrated in vacuo to give crude product 12-1 (737 mg) as a yellow oil. MS (m/z): 302.2 (M+1).

Step 2: Preparation of Compound 12-2

NBS (142 mg, 0.803 mmol) was added to a solution of compound 12-1 (220 mg, 0.730 mmol) in acetonitrile (7 mL) at room temperature. After being stirred at room temperature for 2 hours, the reaction was quenched with addition of 30 mL water. The aqueous phase was extracted with ethyl acetate (20 mL×3). The combined organic was washed with saturated brine (50 mL), dried over anhydrous Na$_2$SO$_4$, filtered, and concentrated in vacuo to give crude product 12-2 (275 mg) as a yellow oil. MS (m/z): 379.9 (M+1).

Step 3: Preparation of Compound 12-3

Under nitrogen atmosphere, BBr$_3$ (0.2 mL) was added to a solution of compound 12-2 (145 mg, 0.382 mmol) in dichloromethane (2 mL) at 0° C. The reaction solution was stirred at 0° C. for 1 hour, then 20 mL saturated aqueous solution of K$_2$CO$_3$ was added to quench the reaction. The aqueous phase was extracted with dichloromethane (10 mL×3). The combined organic was washed with saturated brine (50 mL), dried over anhydrous Na$_2$SO$_4$, filtered and concentrated in vacuo to give crude product 12-2 (127 mg) as a yellow oil. MS (m/z): 365.9 (M+1).

Step 4: Preparation of Compound 12

BBr$_3$ (0.2 mL) was added to a solution of compound 12-3 (50 mg, 0.143 mmol) in dichloromethane (1 mL) at room temperature. The reaction solution was stirred at 0° C. for 1 hour, then 20 mL water was added to quench the reaction and the pH was adjusted to 9 with saturated aqueous solution of K$_2$CO$_3$. The aqueous phase was extracted with dichloromethane (10 mL×3). The combined organic phase was washed with saturated brine (20 mL), dried over anhydrous Na$_2$SO$_4$, filtered and concentrated in vacuo. The residue was purified by HPLC preparative column to give 12 (5 mg, yield: 10.80%). $^1$H NMR (400 MHz, CDCl$_3$): δ 8.84 (br. s., 3H), 7.23 (s, 1H), 6.89 (s, 1H), 3.70 (br. s., 1H), 3.18 (d, J=11.2 Hz, 1H), 2.83 (br. s., 1H), 2.69 (d, J=17.2 Hz, 1H), 2.23-1.98 (m, 3H), 1.89 (br. s., 2H), 1.63 (br. s., 6H), 0.88 (br. s., 2H). MS (m/z): 323.9 (M+1).

Example 13: Preparation of Compound 13

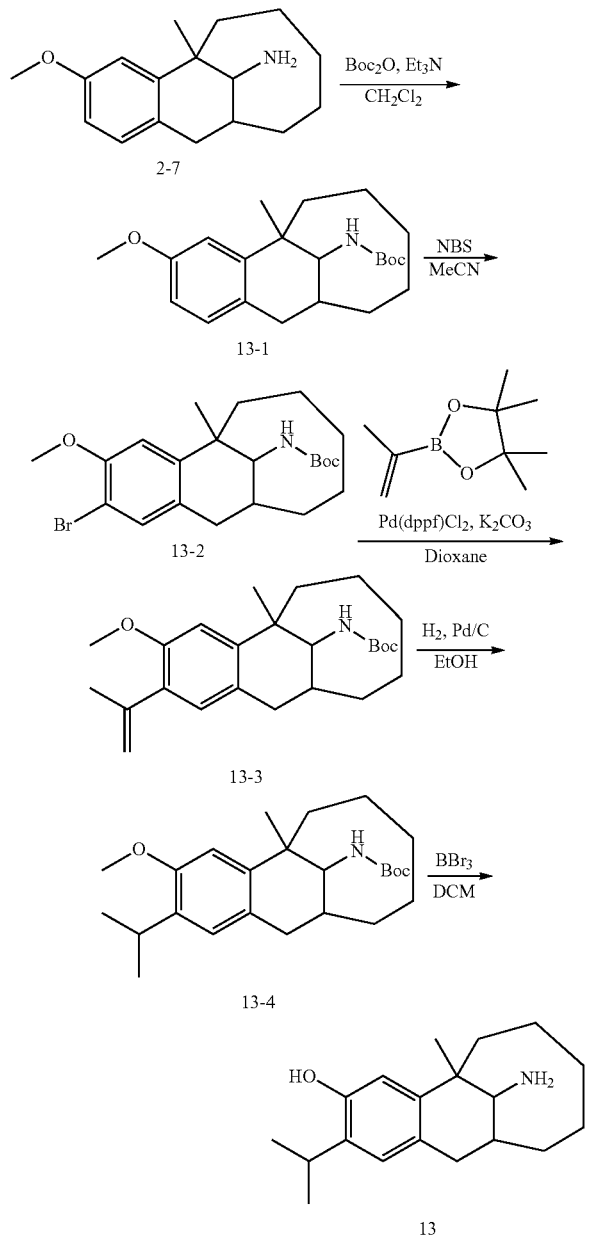

Step 1: Preparation of Compound 13-1

DMAP (50 mg) was added to a mixed solution of compound 2-7 (500 mg, 1.93 mmol), Boc$_2$O (780 mg, 3.86 mmol) and triethylamine (585 mg, 5.79 mmol) in dichloromethane (20 mL) at room temperature. After the reaction mixture was stirred at room temperature for 2 hours, 20 mL water was added to quench the reaction. The aqueous phase was extracted with dichloromethane (20 mL×3). The combined organic phase was washed with saturated brine (20 mL), dried over anhydrous Na$_2$SO$_4$, filtered and concentrated in vacuo. The residue was purified by silica gel column chromatography (eluent: petroleum ether/ethyl acetate=5/1) to give product 13-1 as a colorless oil (203 mg, yield: 29.29%). $^1$H NMR (400 MHz, CDCl$_3$): δ 7.04-6.96 (m, 1H), 6.75 (d, J=2.4 Hz, 1H), 6.70 (dd, J$_1$=2.4 Hz, J$_2$=8.4 Hz, 1H), 4.95 (d, J=10.4 Hz, 1H), 4.10 (dd, J$_1$=5.2 Hz, J$_2$=10.4 Hz, 1H), 3.82-3.76 (m, 3H), 3.17 (dd, J$_1$=6.8 Hz, J$_2$=16.4 Hz, 1H), 2.62 (d, J=16.4 Hz, 1H), 1.91-1.51 (m, 8H), 1.48 (s, 9H), 1.36-1.30 (m, 3H), 0.98 (d, J=6.4 Hz, 2H).

Step 2: Preparation of Compound 13-2

NBS (163 mg, 0.919 mmol) was added to a solution of compound 13-1 (300 mg, 0.836 mmol) in acetonitrile (5 mL) at 25° C. After the reaction mixture was stirred at 25° C. for 2 hours, 20 mL water was added to quench the reaction. The aqueous phase was extracted with ethyl acetate (20 mL×3). The combined organic phases were washed with saturated brine (20 mL), dried over anhydrous Na$_2$SO$_4$, filtered and concentrated in vacuo to give crude product 13-2 (439 mg) as a yellow solid. $^1$H NMR (400 MHz, CDCl$_3$): δ 7.28 (s, 1H), 6.73 (s, 1H), 4.94 (d, J=10.4 Hz, 1H), 4.16-4.07 (m, 1H), 3.88 (s, 3H), 3.19 (dd, J$_1$=6.8 Hz, J$_2$=16.8 Hz, 1H), 2.61 (d, J=16.8 Hz, 1H), 1.84-1.68 (m, 4H), 1.67-1.56 (m, 4H), 1.51 (s, 9H), 1.35 (s, 3H), 1.01 (d, J=6.8 Hz, 2H).

Step 3: Preparation of Compound 13-3

Under nitrogen atmosphere, the mixed solution of compound 13-2 (60 mg, 0.14 mmol), isopropenylboronic acid pinacol ester (69 mg, 0.41 mmol), K$_2$CO$_3$ (56 mg, 0.41 mmol) and Pd(dppf)Cl$_2$ (11 mg, 0.013 mmol) in dioxane (2 mL) was heated at reflux overnight. After being cooled down, the reaction solution was filtered to remove precipitate. The filtrate was concentrated in vacuo. The residue was purified by thin-layer chromatography (eluent: petroleum ether/ethyl acetate=15/1) to give 13-3 as a brown oil (39 mg, yield: 71.0%). $^1$H NMR (400 MHz, CDCl$_3$): δ 6.90 (s, 1H), 6.70 (s, 1H), 5.12-5.13 (m, 2H), 4.93-4.96 (m, 1H), 4.08-4.12 (m, 1H), 3.83 (s, 3H), 3.16-3.20 (m, 1H), 2.89-2.96 (m, 1H), 2.58-2.62 (m, 1H), 2.32 (s, 1H), 2.13 (s, 3H), 1.52-1.84 (m, 13H), 1.26-1.33 (m, 3H), 1.20-1.30 (m, 1H), 0.98-1.00 (m, 4H).

The following compounds were synthesized according to a method similar to that of compound 13-3:

| Compound number | Structure | Spectrogram |
|---|---|---|
| 14-1 | 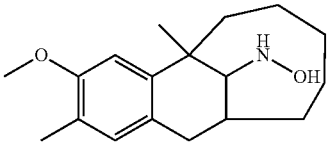 | MS (m/z): 317.9 (M + 1 − 56). |

| Compound number | Structure | Spectrogram |
|---|---|---|
| 15-1 | 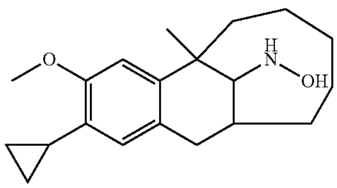 [SMILES: COc1cc2c(cc1C1CC1)CC1CCCCCC2(C)C1NO] | $^1$H NMR (400 MHz, CDCl$_3$): δ 6.65 (s, 1H), 6.51 (s, 1H), 3.84 (s, 3H), 3.22-3.11 (m, 1H), 2.35-2.25 (m, 1H), 2.14-2.13 (m, 1H), 2.00-1.55 (m, 2H), 1.74-1.49 (m, 15H), 1.35-1.15 (m, 5H), 1.00-0.80 (m, 5H), 0.75-0.50 (m, 2H). |

Step 4: Preparation of Compound 13-4

Under hydrogen atmosphere (50 psi), a mixed solution of compound 13-3 and Pd/C (3.9 mg) in ethanol (2 mL) was heated at reflux for 2 hours. After being cooled down, the reaction solution was filtered. The filtrate was concentrated in vacuo to give crude product 13-4 (40 mg). $^1$H NMR (400 MHz, CDCl$_3$): δ 6.90 (s, 1H), 6.64 (s, 1H), 4.96-4.93 (m, 1H), 4.12-4.08 (m, 1H), 3.80 (s, 3H), 3.27-3.15 (m, 2H), 2.65-2.58 (m, 1H), 2.32 (brs, 1H), 1.83-1.62 (m, 6H), 1.50-1.25 (m, 19H), 1.00-0.98 (m, 3H).

Step 5: Preparation of Compound 13

BBr$_3$ (75 mg, 0.30 mmol) was added to a solution of compound 13-4 (40 mg, 0.10 mmol) in dichloromethane (2 mL) at 0° C. After being warmed to room temperature, the reaction solution was stirred for 2 hours. After the reaction was complete, 10 mL saturated sodium bicarbonate solution was added to quench the reaction. The aqueous phase was extracted with dichloromethane (10 mL×5). The combined organic phase was washed with saturated brine (50 mL), dried over anhydrous Na$_2$SO$_4$, filtered and concentrated in vacuo. The residue was purified by HPLC preparative column to give the hydrochloride salt of product 13 (14 mg, yield: 50.0%). $^1$H NMR (400 MHz, CD$_3$OD): δ 6.89 (s, 1H), 6.63 (s, 1H), 3.61 (d, J=5.2 Hz, 1H), 3.25-3.15 (m, 2H), 2.75-2.71 (m, 1H), 2.44 (brs, 1H), 1.93-1.91 (m, 2H), 1.70-1.45 (m, 8H), 1.23-1.15 (m, 7H), 0.97-0.92 (m, 2H). MS (m/z): 288.0 (M+1).

Compounds 14 and 15 were prepared according to a method similar to that of compound 4

Example 5: Preparation of Compound 16

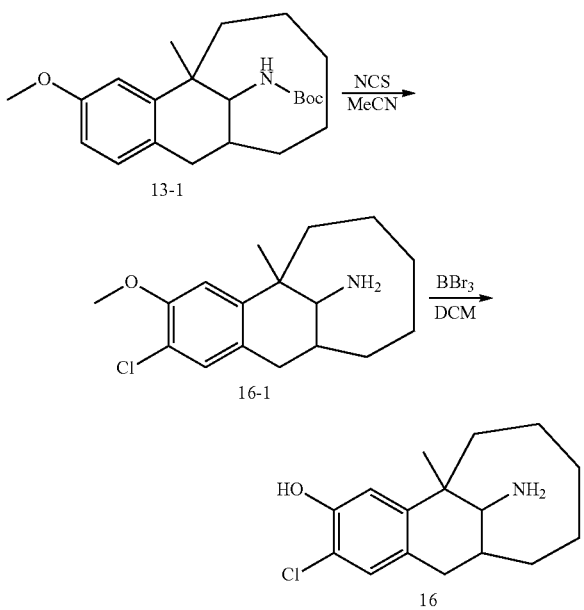

| Compound number | Structure | Spectrogram |
|---|---|---|
| Compound 14 | 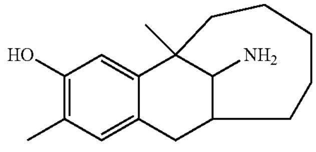 [SMILES: Cc1cc2c(cc1O)C1(C)CCCCCC(C2)C1N] | $^1$H NMR (400 MHz, CDCl$_3$): δ 7.96 (br. s., 3H), 6.86 (s, 1H), 6.63 (s, 1H), 3.66 (br. s., 1H), 3.14 (dd, J$_1$ = 6.4 Hz, J$_2$ = 16.4 Hz, 1H), 2.70 (br. s., 1H), 2.58 (br. s., 1H), 2.22 (s, 3H), 1.97-1.63 (m, 6H), 1.59-1.54 (m, 1H), 1.49 (s, 3H), 1.14 (d, J = 11.6 Hz, 1H), 0.93 (br. s., 2H). MS (m/z): 260.0 (M + 1). |
| Compound 15 | 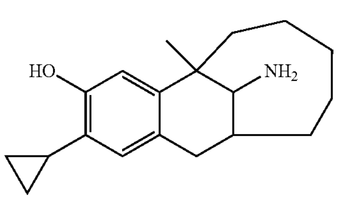 [SMILES: CC12CCCCCC(Cc3cc(C4CC4)c(O)cc31)C2N] | $^1$H NMR (400 MHz, CD$_3$OD): δ 6.78 (s, 1H), 6.62 (s, 1H), 5.98-5.92 (m, 1H), 5.00-4.89 (m, 3H), 3.60-3.58 (m, 1H), 3.16-3.10 (m, 1H), 2.70-2.66 (m, 1H), 2.40-2.39 (m, 1H), 1.91-1.84 (m, 2H), 1.70-1.45 (m, 8H), 1.25-1.05 (m, 2H), 1.00-0.75 (m, 2H). MS (m/z): 286.1 (M + 1). |

Step 1: Preparation of Compound 16-1

Concentrated hydrochloric acid (0.2 mL) was added dropwise to a solution of compound 13-1 (100 mg, 0.28 mmol) and NCS (37 mg, 0.28 mmol) in acetonitrile (2 mL) at 25° C. After being stirred at 25° C. for 2 hours, the reaction was quenched by the addition of 10 mL water. The aqueous phase was extracted with ethyl acetate (10 mL×4). The combined organic phase was washed with saturated brine (10 mL), dried over anhydrous Na$_2$SO$_4$, filtered and concentrated in vacuo to give the crude product 16-1 (88 mg) as a yellow oil. MS (m/z): 293.9 (M+1).

Step 2: Preparation of Compound 16

BBr$_3$ (0.2 mL) was added to a solution of compound 16-1 (88 mg, 0.3 mmol) in dichloromethane (1 mL) at 0° C. After being stirred at 0° C. for 2 hours, the reaction was quenched by the addition of 10 mL saturated potassium carbonate solution. The aqueous phase was extracted with dichloromethane/methanol mixed solution (8:1, 10 mL×3). The combined organic phase was washed with saturated brine (50 mL), dried over anhydrous Na$_2$SO$_4$, filtered and concentrated in vacuo. The residue was purified by HPLC preparative column to give the hydrochloride salt of product 16 (20 mg, yield: 23.81%). $^1$H NMR (400 MHz, CDCl$_3$): δ 8.11 (br. s., 3H), 7.11 (s, 1H), 6.90 (s, 1H), 3.64 (br. s., 1H), 3.17 (dd, J$_1$=6.4 Hz, J$_2$=16.4 Hz, 1H), 2.72 (d, J=17.2 Hz, 1H), 2.62 (br. s., 1H), 1.98-1.81 (m, 5H), 1.62 (br. s., 2H), 1.53 (s, 3H), 1.27-1.17 (m, 1H), 0.92 (br. s., 2H). MS (m/z): 279.9 (M+1).

Example 6: Preparation of Compound 17

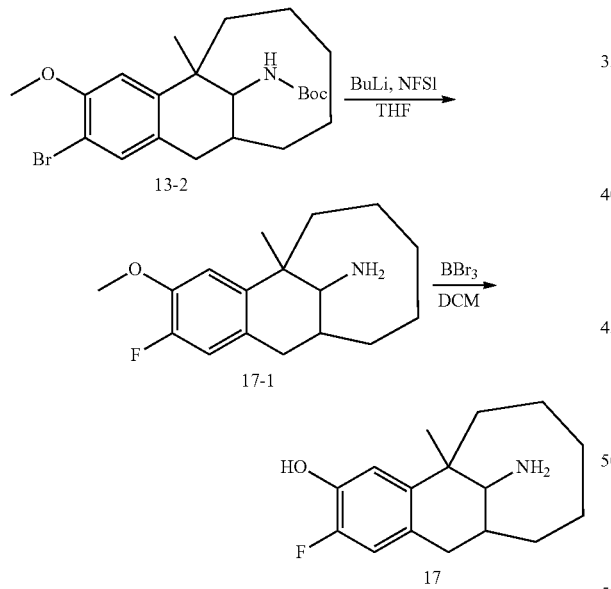

Step 1: Preparation of Compound 17-1

A solution of n-butyllithium in tetrahydrofuran (1 mL, 2.5 mmol) was added to a solution of compound 13-2 (190.00 mg, 433.39 umol) in tetrahydrofuran (3 mL) at −78° C. After being stirred at −78° C. for 1 hour, the reaction mixture was added with a solution of NFSI (273.33 mg, 866.78 umol) in THF (3 mL), and stirred at −78° C. for another 4 hours. Then 20 mL saturated aqueous ammonium chloride solution was added to quench the reaction. The aqueous phase was extracted with ethyl acetate (10 mL×4). The combined organic phase was washed with saturated brine (10 mL), dried over anhydrous Na$_2$SO$_4$, filtered and concentrated in vacuo. The residue was purified by HPLC preparative column to give product 17-1 as a colorless oil (20.00 mg, yield: 12.22%). MS (m/z): 322.1 (M+1-56).

Step 2: Preparation of Compound 17

BBr$_3$ (39.38 mg, 158.94 umol) was added to a solution of compound 17-1 (20.00 mg, 52.98 umol) in dichloromethane (1 mL) at room temperature. After being stirred at room temperature for 2 hours, the reaction was quenched by addition of 10 mL water. The aqueous phase was adjusted to pH=9 with saturated potassium carbonate solution and extracted with dichloromethane (10 mL×5). The combined organic phases were washed with saturated brine (50 mL), dried over anhydrous Na$_2$SO$_4$, filtered and concentrated in vacuo. The residue was purified by HPLC preparative column to give the hydrochloride salt of product 17 (11 mg, yield: 77.84%). $^1$H NMR (400 MHz, CD$_3$OD): δ 6.88-6.80 (m, 2H), 3.66 (d, J=5.2 Hz, 1H), 3.21 (dd, J$_1$=7.2 Hz, J$_2$=16.8 Hz, 1H), 2.74 (d, J=17.2 Hz, 1H), 2.47 (d, J=5.6 Hz, 1H), 2.02-1.88 (m, 2H), 1.78-1.66 (m, 2H), 1.65-1.51 (m, 3H), 1.47 (s, 3H), 1.25-1.15 (m, 1H), 1.01-0.83 (m, 2H). MS (m/z): 264.0 (M+1).

Example 7: Preparation of Compound 18

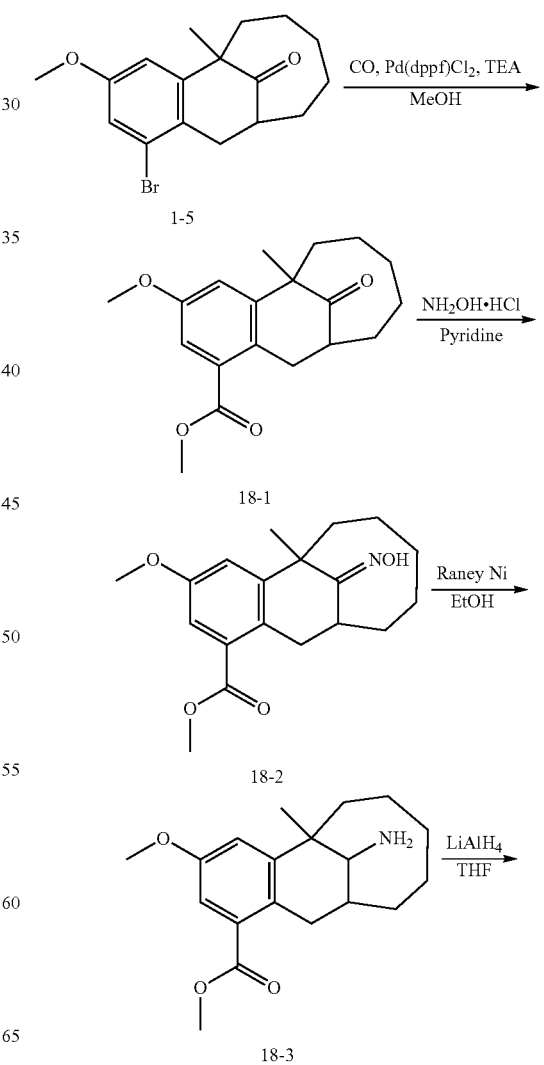

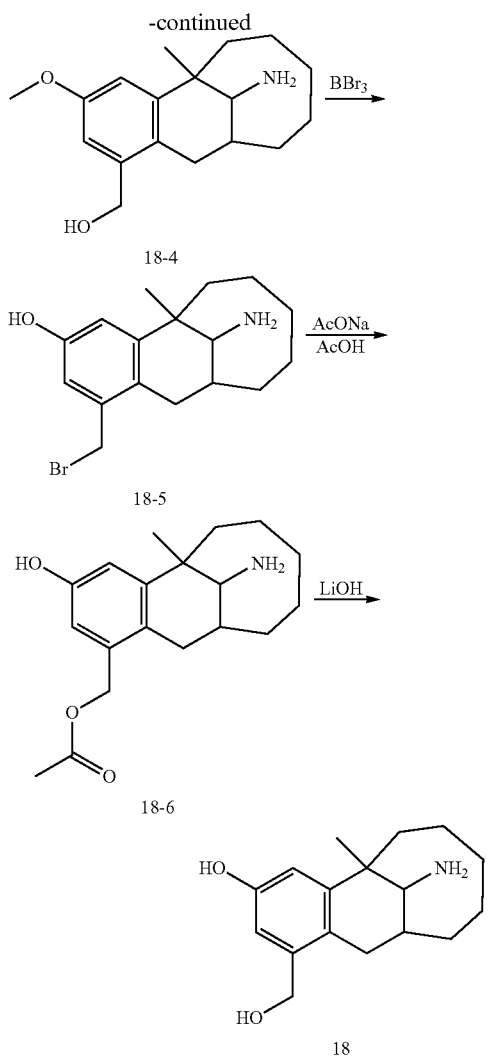

Step 1: Preparation of Compound 18-1

Under nitrogen atmosphere, triethylamine (90.01 mg, 889.56 umol) and Pd(dppf)Cl$_2$ (21.70 mg, 29.65 umol) were added to a solution of compound 1-5 (100.00 mg, 296.52 umol) in methanol (30 mL). The reaction system was evacuated and purged with CO for three times. Then the reaction solution was heated to 70° C. under CO atmosphere (50 psi) and stirred for 24 hours. The reaction mixture was filtered under suction and the filtrate was concentrated in vacuo. The residue was purified by silica gel column chromatography (eluent: petroleum ether/ethyl acetate=10/1) to give product 18-1 (70.00 mg, yield: 74.61%). $^1$H NMR (400 MHz, CDCl$_3$): δ 7.27 (d, J=2.8 Hz, 1H), 6.99 (d, J=2.8 Hz, 1H), 3.91 (s, 3H), 3.85 (s, 3H), 3.44 (dd, J$_1$=4.4 Hz, J$_2$=17.2 Hz, 1H), 3.22 (dd, J$_1$=5.6 Hz, J$_2$=17.2 Hz, 1H), 2.75 (td, J=5.2 Hz, J$_2$=9.6 Hz, 1H), 2.51-2.31 (m, 1H), 1.94-1.64 (m, 4H), 1.35 (s, 3H), 1.33-1.23 (m, 3H).

Step 2: Preparation of Compound 18-2

The mixed solution of compound 18-1 (70.00 mg, 221.25 umol) and NH$_2$OH—HCl (76.87 mg, 1.11 mmol) in pyridine (4 mL) was heated at reflux for 24 hours. After being cooled to room temperature, the reaction solution was poured into ice water (100 mL). The aqueous phase was acidified with dilute hydrochloric acid (1M) and extracted with dichloromethane (100 mL×3). The combined organic phase was washed with saturated brine (100 mL), dried over anhydrous Na$_2$SO$_4$, filtered and concentrated in vacuo. The residue was purified by thin layer chromatography (eluent: petroleum ether/ethyl acetate=10/1) to give product 18-2 (45.00 mg, yield: 61.37%) as a white solid. MS (m/z): 332.5 (M+1).

Step 3: Preparation of Compound 18-3

Under nitrogen atmosphere, Raney-Ni (1.0 g, 50% wt) was added to a solution of compound 18-2 (45.00 mg, 135.78 umol) in ethanol (20 mL). The reaction system was evacuated and purged with H$_2$ for three times. Then the reaction solution was heated to 70° C. under H$_2$ atmosphere (50 psi) and stirred for 48 hours. The reaction mixture was filtered under suction and the filtrate was concentrated in vacuo to give crude product 18-3 (50 mg) which was used directly in the next step without further purification. MS (m/z): 318.1 (M+1).

Step 4: Preparation of Compound 18-4

Under nitrogen atmosphere, lithium tetrahydroaluminate (15.42 mg, 406.41 umol) was slowly added to a solution of compound 18-3 (43.00 mg, 135.47 umol) in tetrahydrofuran (20 mL) at 0° C. After being stirred at 0° C. for 2 hours, the reaction was quenched by the successive addition of water (45 mg) and 15% aqueous sodium hydroxide solution (15 mg). After filtration, the filtrate was concentrated in vacuo to give crude product 18-4 (35 mg) which was used directly in the next step without further purification. MS (m/z): 209.0 (M+1).

Step 5: Preparation of Compound 18-5

Under nitrogen atmosphere, BBr$_3$ (90.89 mg, 362.82 umol) was slowly added to a solution of compound 18-4 (35.00 mg, 120.94 umol) in dichloromethane (5 mL) at −78° C. After being warmed to 0° C., the reaction solution was stirred for 1 hour. Then, water (30 mL) was added to quench the reaction. The aqueous phase was extracted with dichloromethane (30 mL×3). The combined organic phase was washed with saturated brine (30 mL), dried over anhydrous Na$_2$SO$_4$, filtered and concentrated in vacuo to give crude product 18-5 (35.00 mg) which was used directly in the next step without further purification. MS (m/z): 399.9 (M+1)

Step 6: Preparation of Compound 18-6

The mixed solution of compound 18-5 (63.00 mg, 178.82 umol) and sodium acetate (73.34 mg, 894.10 umol) in acetic acid (3 mL) was heated to reflux and stirred for 1 h. After being cooled down, the reaction solution was poured into 20 mL ice water to be diluted. The aqueous phase was extracted with dichloromethane (20 mL×3). The combined organic phase was washed with saturated brine (20 mL), dried over anhydrous Na$_2$SO$_4$, filtered and concentrated in vacuo to give the crude product. The crude product was purified by HPLC preparative column to give product 18-6 as a white solid (20.00 mg, yield: 33.18%). MS (m/z): 318.1 (M+1).

Step 7: Preparation of Compound 18

The solution of compound 18-6 (10.00 mg, 31.50 umol) and lithium hydroxide (73.77 mg, 157.50 umol) in ethanol (2 mL) was stirred at 25° C. for 16 hours. After the reaction solution was concentrated in vacuo, 20 mL water was added and the mixture was acidified to pH=2 with dilute hydrochloric acid. The aqueous phase was extracted with dichloromethane (20 mL×3). The combined organic phase was washed with saturated brine (20 mL), dried over anhydrous Na$_2$SO$_4$, filtered and concentrated in vacuo to give the crude product. The crude product was purified by HPLC preparative column to give product 18 (6.00 mg, yield: 60.55%). $^1$H NMR (400 MHz, CD$_3$OD): δ 6.84 (d, J=2.4 Hz, 1H), 6.67 (d, J=2.4 Hz, 1H), 4.69-4.50 (m, 3H), 3.65 (d, J=5.6 Hz, 1H), 3.08-2.82 (m, 2H), 2.54 (d, J=6.0 Hz, 1H), 1.95 (dd, J$_1$=7.2

Hz, J$_2$=15.6 Hz, 2H), 1.81-1.64 (m, 2H), 1.64-1.50 (m, 3H), 1.47 (s, 3H), 1.20 (d, J=11.6 Hz, 1H), 1.04-0.82 (m, 2H). MS (m/z): 276.0 (M+1).

Example 19: Preparation of Compound 19

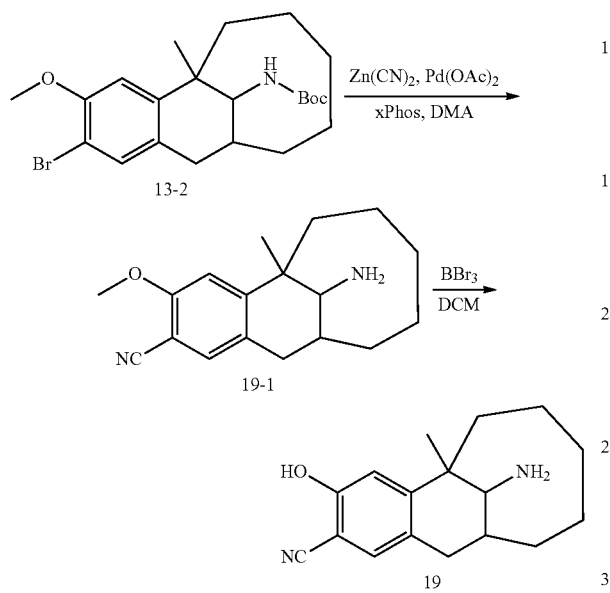

Example 20: Preparation of Compound 20

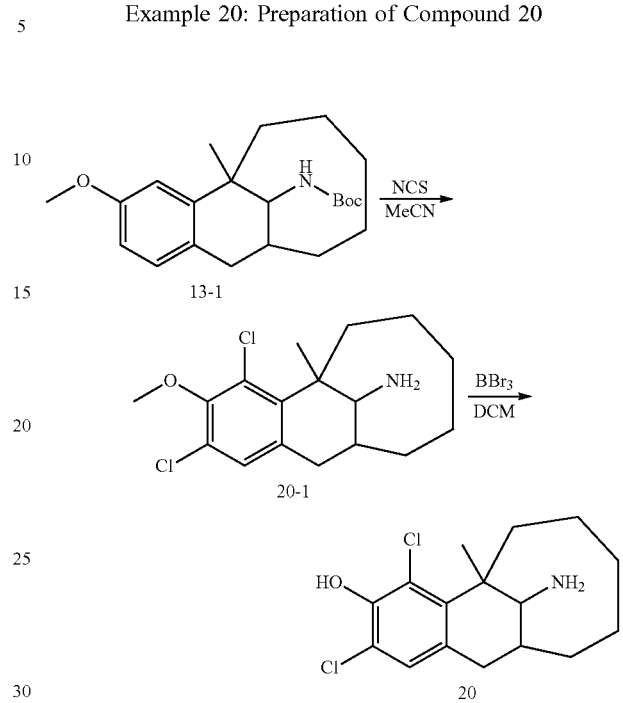

Step 1: Preparation of Compound 19-1

Under nitrogen atmosphere, Pd(OAc)$_2$ (0.15 g) and xPhos (0.62 g) were added to a mixed solution of concentrated sulfuric acid (24 μL) and dimethylacetamide (10 mL), then the mixture was heated to 80° C. and stirred for 30 minutes to obtain a dark solution A.

In another flask, the prepared solution A (1 mL) was added to a solution of compound 13-2 (50 mg, 0.139 mmol), Zn(CN)$_2$ (16 mg, 0.139 mmol) and Zn (0.5 mg, 0.008 mmol) in dimethylacetamide. Then, the reaction solution was heated to 90° C. and stirred overnight. After being cooled to room temperature, the reaction solution was filtered. The filtrate was poured into 10 mL water. The aqueous phase was extracted with ethyl acetate (10 mL×4). The combined organic phase was washed with saturated brine (30 mL), dried over anhydrous Na$_2$SO$_4$, filtered and concentrated in vacuo. The residue was purified by thin layer chromatography (eluent: petroleum ether/ethyl acetate=5/1) to give product 19-1 (18.0 mg, yield: 40.91%). MS (m/z): 328.9 (M+1-56).

Step 2: Preparation of Compound 19

BBr$_3$ (27 mg, 0.109 mmol) was slowly added to a solution of compound 19-1 (14 mg, 0.036 mmol) in dichloromethane (2 mL) at room temperature. After being stirred at room temperature for 5 hours, the reaction was quenched by addition of water (10 mL). The aqueous phase was basified with potassium carbonate to pH=9 and extracted with dichloromethane (10 mL×4). The combined organic phase was washed with saturated brine (10 mL), dried over anhydrous Na$_2$SO$_4$, filtered, and concentrated in vacuo to give the crude product. The crude product was purified by HPLC preparative column to give product 19 (8 mg, yield: 80.0%). $^1$H NMR (400 MHz, CD$_3$OD): δ 7.01 (s, 1H), 6.67 (s, 1H), 3.08-2.98 (m, 2H), 2.61 (d, J=16.0 Hz, 1H), 2.27-2.19 (m, 1H), 2.00-1.92 (m, 1H), 1.80-1.72 (m, 3H), 1.71-1.58 (m, 2H), 1.51 (dd, J$_1$=6.4 Hz, J$_2$=13.6 Hz, 2H), 1.36-1.31 (m, 3H), 1.12-0.94 (m, 3H). MS (m/z): 271.1 (M+1).

Step 1: Preparation of Compound 20-1

Concentrated hydrochloric acid (0.4 mL) was added dropwise to a solution of compound 13-1 (80 mg, 0.223 mmol) and NCS (74 mg, 0.557 mmol) in acetonitrile (2 mL) at 25° C. After being stirred at 25° C. for 5 hours, the reaction was quenched by addition of 10 mL water. The aqueous phase was extracted with ethyl acetate (10 mL×4). The combined organic phase was washed with saturated brine (10 mL), dried over anhydrous Na$_2$SO$_4$, filtered and concentrated in vacuo. The residue was purified by thin layer chromatography (eluent: petroleum ether/ethyl acetate=5/1) to give product 20-1 as a colorless oil (40.0 mg, yield: 54.79%). MS (m/z): 328.1 (M+1).

Step 2: Preparation of Compound 20

BBr$_3$ (91 mg, 0.367 mmol) was slowly added to the a solution of compound 20-1 (14 mg, 0.036 mmol) in dichloromethane (2 mL) at 0° C. After being stirred at 0° C. for 5 hours, the reaction was quenched by addition of water (10 mL). The aqueous phase was basified with potassium carbonate to pH=9 and extracted with dichloromethane (10 mL×4). The combined organic phase was washed with saturated brine (10 mL), dried over anhydrous Na$_2$SO$_4$, filtered, and concentrated in vacuo to give the crude product. The crude product was separated and purified by HPLC preparative column to give product 20 (3.0 mg, yield: 7.89%). $^1$H NMR (400 MHz, CD$_3$OD): δ 7.19 (s, 1H), 4.64 (br. s., 1H), 3.63 (d, J=4.8 Hz, 1H), 2.83 (d, J=17.2 Hz, 1H), 2.60 (dd, J$_1$=7.6 Hz, J$_2$=16.4 Hz, 1H), 2.40 (d, J=6.4 Hz, 1H), 2.06-1.96 (m, 1H), 1.74 (s, 3H), 1.69 (br. s., 2H), 1.63-1.52 (m, 2H), 1.35-1.16 (m, 2H), 0.95 (d, J=12.8 Hz, 1H), 0.87-0.76 (m, 1H). MS (m/z): 314.1 (M+1).

Example 21: Preparation of Compound 21 and Compound 22

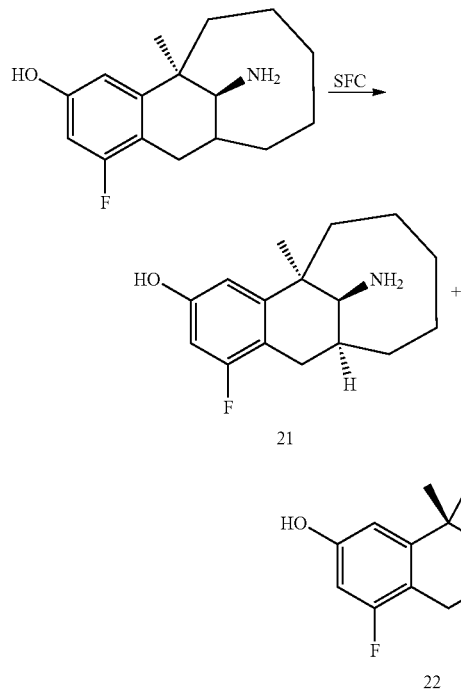

Compound 6 (700.00 mg, 2.66 mmol) was separated by SFC to give compound 21 (150 mg) and 22 (160 mg).

SFC separation condition: Instrument: Thar 80; Column: Chiralpak AD 250×30 mm I.D., 5 um; Mobile phase: Supercritical $CO_2$/IPA (0.1% $NH_3H_2O$)=65/35 at 50 mL/min; Column Temp: 38° C.; Nozzle Pressure: 100Bar; Nozzle Temp: 60° C.; Evaporator Temp: 20° C.; Trimmer Temp: 25° C.; Wavelength: 220 nm.

Compound 21 $^1$H NMR (400 MHz, $CD_3OD$): δ 6.54 (s, 1H), 6.36 (dd, $J_1$=2.4 Hz, $J_2$=11.2 Hz, 1H), 3.09 (d, J=5.2 Hz, 1H), 2.80 (d, J=4.4 Hz, 2H), 2.39-2.27 (m, 1H), 2.05-1.91 (m, 1H), 1.84-1.48 (m, 6H), 1.35 (s, 3H), 1.30-1.21 (m, 1H), 1.02-0.80 (m, 2H). MS (m/z): 264.0 (M+1). $[α]20D$=−43.8 (C=3.1, $CH_3OH$).

Compound 22 1H NMR (400 MHz, $CD_3OD$): δ 6.56 (s, 1H), 6.36 (dd, $J_1$=2.4 Hz, $J_2$=11.2 Hz, 1H), 3.67 (d, J=5.2 Hz, 1H), 2.95-2.80 (m, 2H), 2.60-2.51 (m, 1H), 2.05-1.91 (m, 2H), 1.84-1.55 (m, 5H), 1.48 (s, 3H), 1.28-1.15 (m, 1H), 1.02-0.80 (m, 2H). MS (m/z): 264.0 (M+1). $[α]20D$=+39.8 (C=2.0, $CH_3OH$).

Compounds 23-26 were isolated referring to the SFC separation method described above:

| Compound number | Structure | Spectrogram |
|---|---|---|
| Compound 23 | 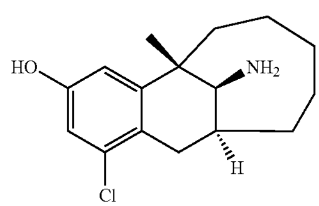 [SMILES: C[C@]12CCCCC[C@@H](Cc3c(Cl)cc(O)cc31)[C@@H]2N] | $^1$H NMR (400 MHz, $CD_3OD$): δ 6.72 (d, J = 2.4 Hz, 1H), 6.67 (d, J = 2.0 Hz, 1H), 2.96-2.84 (m, 2H), 2.45 (brs, 1H), 1.94-1.75 (m, 4H), 1.42-1.25 (m, 4H), 1.58-1.54 (m, 3H), 1.19-1.10 (m, 1H), 0.95-0.75 (m, 2H). |
| Compound 24 | 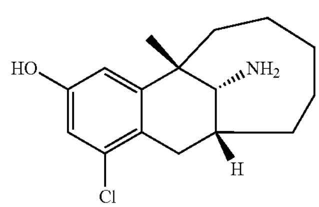 [SMILES: C[C@]12CCCCC[C@H](Cc3c(Cl)cc(O)cc31)[C@H]2N] | $^1$H NMR (400 MHz, $CD_3OD$): δ 6.72 (d, J = 2.4 Hz, 1H), 6.67 (d, J = 2.0 Hz, 1H), 3.18-3.16 (m, 1H), 2.96-2.82 (m, 2H), 2.38 (brs, 1H), 1.94-1.90 (m, 1H), 1.77-1.70 (m, 2H), 1.62-1.45 (m, 3H), 1.35 (s, 1H), 1.16-1.10 (m, 1H), 0.95-0.75 (m, 2H). |
| Compound 25 | 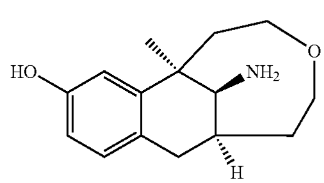 [SMILES: C[C@@]12CCOCC[C@@H](Cc3ccc(O)cc31)[C@@H]2N] | $^1$H NMR (400 MHz, $CD_3OD$): δ 6.92 (d, J = 8.4 Hz, 1H), 6.75 (d, J = 2.0 Hz, 1H), 6.61 (dd, $J_1$ = 2.0 Hz, $J_2$ = 2.0 Hz, 1H), 3.76-3.69 (m, 2H), 3.52-3.45 (m, 1H), 3.44-3.40 (m, 1H), 3.30-3.25 (m, 1H), 3.07-3.04 (m, 1H), 2.63 (d, J = 16.0 Hz, 1H), 2.33 (brs, 1H), 2.05-2.02 (m, 2H), 1.99-1.85 (m, 1H), 1.63-1.52 (m, 1H), 1.36 (s, 3H). |

| Compound number | Structure | Spectrogram |
|---|---|---|
| Compound 26 | 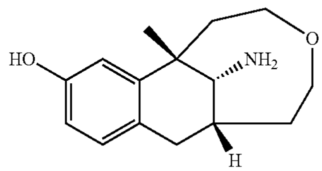 [SMILES: C[C@]12CCOCC[C@H](Cc3ccc(O)cc31)[C@H]2N] | $^1$H NMR (400 MHz, CD$_3$OD): δ 6.93 (d, J = 8.8 Hz, 1H), 6.75 (d, J = 2.4 Hz, 1H), 6.61 (dd, J$_1$ = 2.0 Hz, J$_2$ = 2.0 Hz, 1H), 3.77-3.70 (m, 2H), 3.52-3.45 (m, 1H), 3.45-3.43 (m, 1H), 3.27-3.26 (m, 1H), 3.07-3.05 (in, 1H), 2.64 (d, J = 15.6 Hz, 1H), 2.35 (brs, 1H), 2.06-2.03 (m, 2H), 2.03-1.92 (m, 1H), 1.64-1.52 (m, 1H), 1.36 (s, 3H) |

Example 27: Preparation of Compound 27

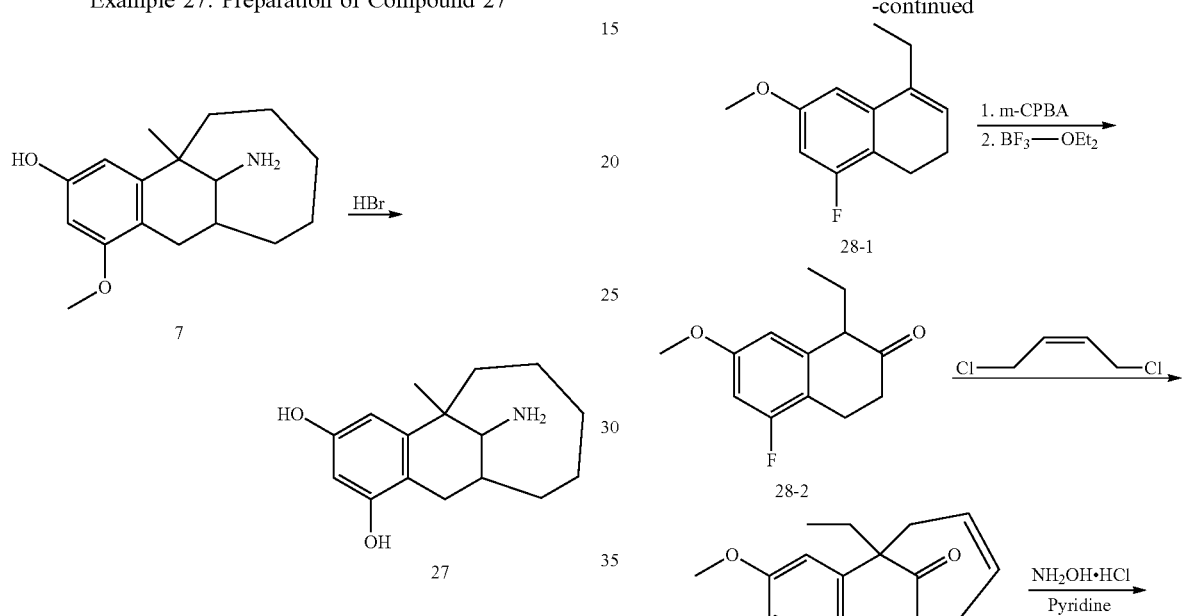

Step 1: Preparation of Compound 27

Under nitrogen atmosphere, the mixture of compound 7 (16.00 mg, 58.10 umol) and aqueous hydrobromic acid (48% wt, 3 mL) was heated to 100° C. and stirred for 1 hour. After being cooled to room temperature, the reaction solution was concentrated in vacuo. The residue was purified by HPLC preparative column to give product 27 (8.00 mg, yield: 46.23%). $^1$H NMR (400 MHz, CD$_3$OD): δ 6.27-6.20 (m, 1H), 3.61 (d, J=5.2 Hz, 1H), 2.90 (s, 1H), 2.80 (d, J=7.2 Hz, 1H), 2.59-2.45 (m, 1H), 2.04-1.83 (m, 2H), 1.76-1.48 (m, 5H), 1.44 (s, 3H), 1.31-1.12 (m, 1H), 1.05-0.88 (m, 2H). MS (m/z): 262.1 (M+1).

Example 28: Preparation of Compound 28 and Compound 29

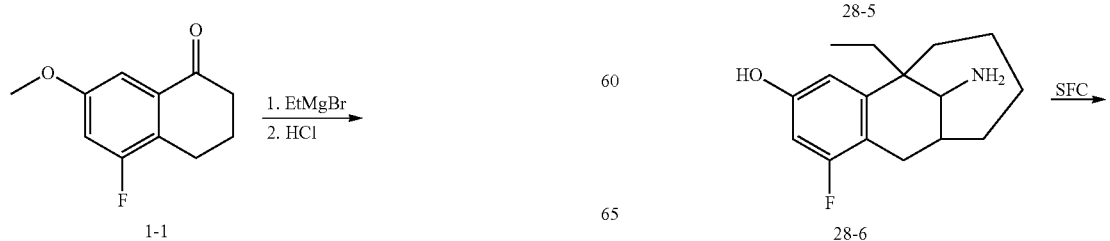

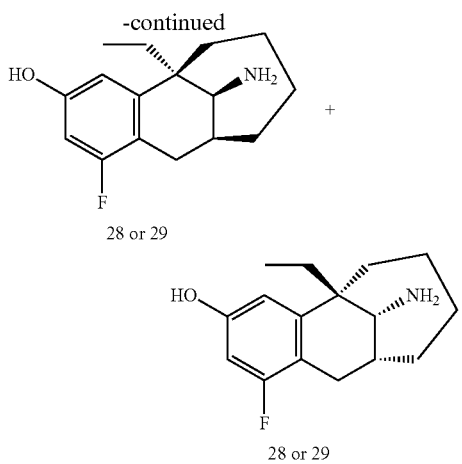

28 or 29

28 or 29

Step 1: Preparation of Compound 28-1

Compound 1-1 (2.00 g, 10.30 mmol) was dissolved in toluene (5.00 mL) and a solution of EtMgBr in tetrahydrofuran (13.73 mL, 3M, 41.19 mmol) was added dropwise at −78° C. After the dropwise addition was complete, the temperature was slowly raised to 25° C. and the reaction was continued for 2 hours. After the reaction was complete, water (10 mL) was added to quench the reaction, then HCl (10 mL, 4M) was added. The temperature was raised to 60° C., and the reaction was continued under stirring for 3 hours. After being cooled down, the reaction solution was extracted with dichloromethane (10 mL×2). The combined organic phase was washed with saturated brine (10 mL), dried over anhydrous $Na_2SO_4$, filtered and concentrated in vacuo. The residue was purified by silica gel column chromatography (eluent: petroleum ether/ethyl acetate=10/1) to give product 28-1 as a pale yellow oil (1.50 g, yield: 70.6%). $^1$H NMR (400 MHz, $CDCl_3$) δ 6.64 (dd, $J_1$=10.2 Hz, $J_2$=2.4 Hz, 1H), 6.52 (dd, $J_1$=10.8 Hz, $J_2$=2.4 Hz, 1H), 5.92 (t, J=4.4 Hz, 1H), 3.82 (s, 3H), 2.68 (t, J=8.4 Hz, 2H), 2.40 (dd, $J_1$=7.2 Hz, $J_2$=1.2 Hz, 2H), 2.01-2.27 (m, 2H), 1.14 (t, J=7.2 Hz, 3H)

Step 2: Preparation of Compound 28-2

Compound 28-1 (1.50 g, 7.27 mmol) was dissolved in dichloromethane (4.00 mL), m-CPBA (1.51 g, 8.73 mmol) was added in portions under an ice bath, the internal temperature was maintained within 0-5° C., and the mixture was stirred for another 2 hours. The reaction was quenched by successive addition of saturated $Na_2SO_3$ (10 mL) and $NaHCO_3$ (5 mL). The reaction solution was extracted with dichloromethane (10 mL×2) and the combined organic phase was dried over anhydrous $Na_2SO_4$ and filtered. $BF_3.Et_2O$ (103.22 mg, 727.24 umol) was added to the filtered solution under an ice bath, and the mixture was stirred at the same temperature for 0.5 hours. The reaction was quenched by addition of saturated $NaHCO_3$ (10 mL) and the aqueous phase was extracted with dichloromethane (10 mL×2). The combined organic phase was washed with saturated brine (10 mL×2), dried over sodium sulfate, filtered and concentrated in vacuo. The residue was purified by silica gel column chromatography (eluent: petroleum ether/ethyl acetate=20/1 to 10/1) to give the product 28-2 as a pale yellow oil (1.00 g, yield: 61.9%). MS (m/z): 222.9 (M+1). $^1$H NMR (400 MHz, $CDCl_3$) δ 6.54 (dd, $J_1$=11.04 Hz, $J_2$=2.40 Hz, 1H), 6.49 (d, J=2.24 Hz, 1H), 3.79 (s, 3H), 3.30 (t, J=6.64 Hz, 1H), 3.08 (s, 1H), 2.86-3.01 (m, 1H), 2.57-2.71 (m, 1H), 2.33-2.53 (m, 1H), 1.84-1.94 (m, 2H), 0.89 (t, J=7.20 Hz, 3H).

Step 3: Preparation of Compound 28-3

Under an ice bath, compound 28-2 (900.0 mg, 4.05 mmol) was dissolved in THF (5.00 mL), then the reaction system was purged with nitrogen for 3 times, then potassium tert-butoxide (545.27 mg, 4.86 mmol) was added. After being stirred at the same temperature for 1 hour, the reaction solution was slowly added to a solution of cis-1,4-dichloro-2-butene (1.01 g, 8.10 mmol) in THF (5.00 mL). After reacting at 25° C. for 12 hours, t-BuOK (545.27 mg, 4.86 mmol) was added, then the temperature was raised to 60° C., and the reaction was continued for 6 hours, the reaction solution was slowly poured into water (10 mL) to be quenched. The aqueous phase was extracted with dichloromethane (10 mL×2). The combined organic phase was washed with saturated brine (10 mL×2), dried over anhydrous sodium sulfate, filtered and concentrated in vacuo. The residue was purified by silica gel column chromatography (eluent: petroleum ether/ethyl acetate=10/1) to give product 28-3 as a pale yellow oil (800.00 mg, yield: 72.1%). MS (m/z): 275.1 (M+1). $^1$H NMR (400 MHz, $CDCl_3$) δ 6.46-6.55 (m, 2H), 5.64-5.76 (m, 1H), 5.32-5.45 (m, 1H), 3.79 (s, 3H), 3.02-3.12 (m, 1H), 2.95-3.00 (m, 2H), 2.52 (dd, $J_1$=13.6 Hz, $J_2$=7.2 Hz, 1H), 2.42 (dd, $J_1$=15.6 Hz, $J_2$=7.6 Hz, 1H), 2.12 (dd, $J_1$=15.6 Hz, $J_2$=2.4 Hz, 1H), 1.70 (dd, $J_1$=13.6 Hz, $J_2$=7.2 Hz, 1H), 1.13-1.31 (m, 2H), 0.61 (t, J=7.2 Hz, 3H).

Step 4: Preparation of Compound 28-4

Compound 28-3 (700.00 mg, 2.55 mmol) was dissolved in pyridine (5.00 mL) and hydroxylamine hydrochloride (1.06 g, 15.30 mmol) was added. After being warmed to 100° C. and reacted for 12 hours, the reaction was quenched by addition of water (5 mL) and the aqueous phase was extracted with dichloromethane (10 mL×2). The combined organic phase was washed with water (5 mL×2). The organic phase was adjusted to pH 5-6 with dilute hydrochloric acid, then washed with water (5 mL×2). The organic phase was dried over anhydrous sodium sulfate, filtered and concentrated in vacuo. Ethyl acetate (1 mL) was added to the residue, then the mixture was allowed to stand overnight, white precipitate was precipitated. The mixture was filtered to give compound 28-4 as a white solid (600.00 mg, yield: 81.3%). MS (m/z): 289.9 (M+1). $^1$H NMR (400 MHz, $CD_3OD$) δ 6.65 (s, 1H), 6.50 (dd, J=11.6 Hz, $J_2$=2.4 Hz, 1H), 5.58 (ddd, $J_1$=11.2, $J_2$=7.6, $J_3$=3.6 Hz, 1H), 5.17-5.35 (m, 1H), 3.77 (s, 3H), 2.76-2.85 (m, 1H), 2.71 (d, J=7.2 Hz, 1H), 2.53-2.62 (m, 1H), 2.44-2.53 (m, 1H), 2.26-2.41 (m, 2H), 2.17-2.26 (m, 1H), 1.88-2.01 (m, 1H), 0.66 (t, J=7.2 Hz, 3H).

Step 5: Preparation of Compound 28-5

Compound 28-4 (400.00 mg, 1.38 mmol) was dissolved in ethanol (5.00 mL) then Raney nickel (236.45 mg) and $NH_3.H_2O$ (4.84 mg, 138.00 umol) were added. After the reaction system was purged with nitrogen for 3 times, hydrogen gas was introduced. The reaction was carried out under 50 Psi at 70° C. for 12 hours. The reaction solution was filtered through celite and concentrated in vacuo to give crude product 28-5 (500.00 mg) as a pale yellow oil. MS (m/z): 277.9 (M+1). $^1$H NMR (400 MHz, $CD_3OD$) δ 6.66 (br, 1H), 6.53 (d, J=10.8 Hz, 1H), 3.77 (br, 3H), 2.66-2.81 (m, 2H), 1.82-2.13 (m, 4H), 1.32-1.72 (m, 6H), 1.05-1.22 (m, 2H), 0.58 (t, J=6.8 Hz, 3H).

Step 6: Preparation of Compound 28

Compound 28-5 (450.00 mg, 1.62 mmol) was dissolved in hydrobromic acid (2.00 mL) and the reaction solution was stirred at 100° C. for 3 hours. After being cooled down, the reaction solution was concentrated in vacuo to give the crude product. The crude product was purified by HPLC preparative column to give trifluoroacetate salt of 28-6. Compound 28-6 was separated by SFC to give compound 28 (30 mg) at the first peak and compound 29 (35 mg) at the second peak.

SFC separation condition: Instrument: Thar 80; Column: Chiralpak AD 250×30 mm I.D., 5 um; Mobile phase: Supercritical $CO_2$/IPA (0.1% $NH_3H_2O$)=65/35 at 50 mL/min; Column Temp: 38° C.; Nozzle Pressure: 100Bar; Nozzle Temp: 60° C.; Evaporator Temp: 20° C.; Trimmer Temp: 25° C.; Wavelength: 220 nm.

Compound 28: MS (m/z): 263.9 (M+1). $^1$H NMR (400 MHz, $CD_3OD$) δ 6.55 (d, J=1.6 Hz, 1H), 6.35 (dd, $J_1$=11.2 Hz, $J_2$=2.4 Hz, 1H), 3.27 (d, J=3.2 Hz, 1H), 2.61-2.79 (m, 2H), 2.31-2.44 (m, 1H), 1.78-2.13 (m, 3H), 1.26-1.74 (m, 6H), 1.05-1.22 (m, 1H), 0.52-0.65 (m, 3H).

Compound 29: MS (m/z): 263.9 (M+1). $^1$H NMR (400 MHz, $CD_3OD$) δ 6.58 (s, 1H), 6.44 (dd, $J_1$=11.2 Hz, $J_2$=2.4 Hz, 1H), 3.79 (d, J=3.2 Hz, 1H), 2.75-2.93 (m, 2H), 2.60 (br. s., 1H), 1.68-2.07 (m, 5H), 1.27-1.67 (m, 2H), 1.09-1.26 (m, 2H), 0.67 (t, J=7.28 Hz, 3H).

Example 30: Preparation of Compound 30

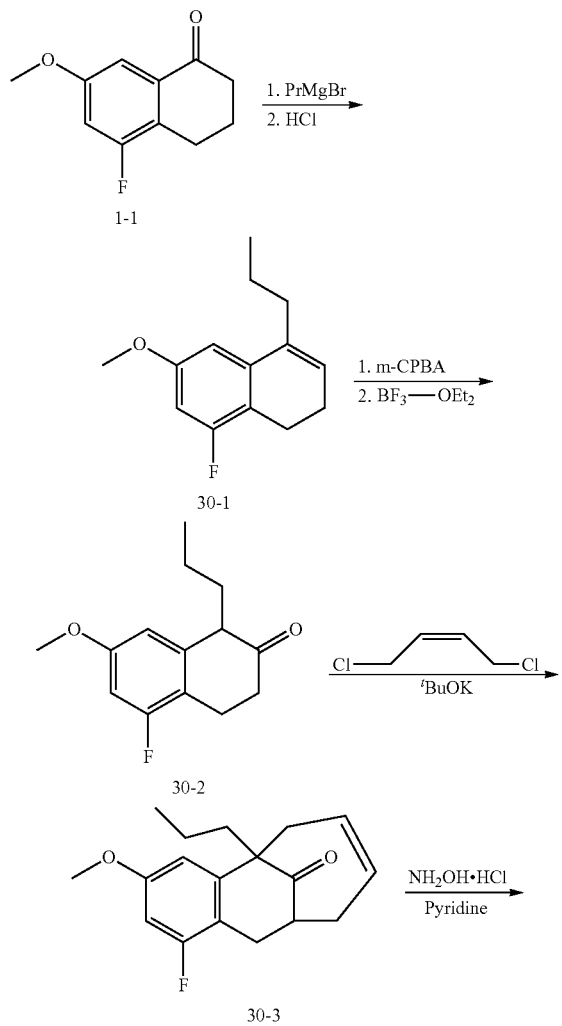

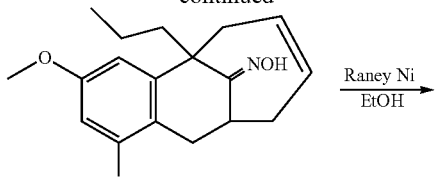

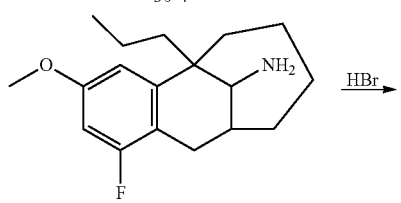

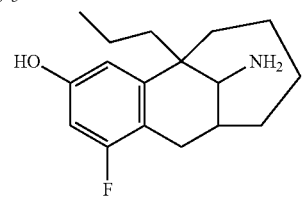

Step 1: Preparation of Compound 30-1

Compound 1-1 (2.00 g, 10.30 mmol) was dissolved in toluene (10.00 mL) and a solution of PrMgBr in tetrahydrofuran (7.73 mL, 2M, 15.46 mmol) was added dropwise at −78° C. After the dropwise addition was complete, the temperature was slowly raised to 25° C. and the reaction was continued for 2 hours. After the reaction was complete, the reaction was quenched by the addition of water (10 mL), then HCl (25.75 mL, 4 M) was added. The temperature was raised to 60° C. and the reaction was continued for 3 hours under stirring. After being cooled down, the reaction solution was extracted with dichloromethane (10 mL×2). The combined organic phase was dried over anhydrous sodium sulfate, filtered, and the combined organic phase was washed with saturated brine (20 mL), dried over anhydrous $Na_2SO_4$, filtered, and concentrated in vacuo. The residue was purified by silica gel column chromatography (eluent: petroleum ether/ethyl acetate=10/1) to give product 30-1 (1.50 g, yield: 66.2%) as a colorless oil. $^1$H NMR (400 MHz, $CDCl_3$) δ=6.72 (s, 1H), 6.65 (d, J=2.0 Hz, 1H), 6.56 (dd, $J_1$=2.4 Hz, $J_2$=11.2 Hz, 1H), 6.48 (dd, $J_1$=2.4 Hz, $J_2$=11.2 Hz, 1H), 5.91 (t, J=4.4 Hz, 1H), 5.23 (t, J=3.2 Hz, 1H), 3.81-3.78 (m, 6H), 2.84 (br. s., 1H), 2.68 (t, J=7.2 Hz, 3H), 2.61-2.43 (m, 1H), 2.37 (t, J=7.2 Hz, 2H), 2.32-2.03 (m, 5H), 1.96-1.74 (m, 1H), 1.58-1.51 (m, 4H), 1.07 (t, J=7.6 Hz, 1H), 0.95 (t, J=7.2 Hz, 3H)

Step 2: Preparation of Compound 30-2

Compound 30-1 (1.50 g, 6.81 mmol) was dissolved in dichloromethane (5.00 mL), then $Na_2CO_3$ (1.08 g, 10.21 mmol) and m-CPBA (1.41 g, 8.17 mmol) were added successively under an ice bath, the internal temperature was maintained within 0-5° C., and the reaction was stirred for 1 hour. The reaction was quenched by addition of saturated $Na_2SO_3$ (5 mL) solution. The aqueous phase was extracted with dichloromethane (10 mL×3), then the combined organic phase was dried over anhydrous $Na_2SO_4$ and filtered. The residue obtained after concentration in vacuo was dissolved in dichloromethane (10.00 mL). $BF_3 \cdot Et_2O$ (150.17 mg, 1.06 mmol) was added to the dichloromethane solution under an ice bath, and the mixture was stirred at the same temperature for 0.5 hours. The reaction was quenched by addition of saturated NaHCO$_3$ (10 mL) solution. The aqueous phase was extracted with dichloromethane (10 mL×3). The combined organic phase was washed with saturated brine (10 mL×2), dried over sodium sulfate, filtered and concentrated in vacuo. The residue was purified by silica gel column chromatography (eluent: petroleum ether/ethyl acetate=10/1) to give product 30-2 as a pale yellow oil (0.4 g, yield: 16%). MS (m/z): 236.8 (M+1). $^1$H NMR (400 MHz, CDCl$_3$) δ 6.53 (dd, J=2.4, 11.2 Hz, 1H), 6.48 (d, J=2.0 Hz, 1H), 3.79 (s, 3H), 3.37 (t, J=6.8 Hz, 1H), 3.20-2.87 (m, 2H), 2.72-2.37 (m, 2H), 1.87-1.73 (m, 2H), 1.37-1.19 (m, 2H), 0.91 (t, J=7.2 Hz, 3H).

Step 3: Preparation of Compound 30-3

Compound 30-2 (300.0 mg, 1.27 mmol) was dissolved in THF (5.00 mL) under an ice bath and the reaction system was purged with nitrogen for three times, then potassium tert-butoxide (170.96 mg, 1.52 mmol) was added. After being stirred at the same temperature for 1 hour, the reaction solution was slowly added to a solution of cis-1,4-dichloro-2-butene (238.07 mg, 1.90 mmol) in THF (5.00 mL). After the mixture reacted at 25° C. for 12 hours, t-BuOK (170.96 mg. 1.52 mmol) was added, then the temperature was raised to 60° C. and the reaction was continued for 6 hours, the reaction solution was slowly poured into water (5 mL) to be quenched. The aqueous phase was extracted with dichloromethane (10 mL×2). The combined organic phase was dried over anhydrous sodium sulfate, filtered and concentrated in vacuo. The residue was purified by thin layer chromatography (eluent: petroleum ether/ethyl acetate=10/1) to give product 30-3 as a pale yellow oil (200.00 mg, yield: 54.61%). $^1$H NMR (400 MHz, CDCl$_3$) δ 6.53 (d, J=2.4 Hz, 1H), 6.49 (dd, J$_1$=2.0 Hz, J$_2$=11.2 Hz, 1H), 5.77-5.63 (m, 1H), 5.50-5.25 (m, 1H), 3.79-3.77 (m, 3H), 3.64 (s, 1H), 3.57 (s, 1H), 3.06 (d, J=5.6 Hz, 1H), 2.99-2.91 (m, 2H), 2.54-2.36 (m, 2H), 2.33-2.22 (m, 2H), 2.13 (d, J=2.0 Hz, 1H), 1.12-0.93 (m, 1H), 0.85-0.82 (m, 3H).

Step 4: Preparation of Compound 30-4

Compound 30-3 (200.00 mg, 0.69 mmol) was dissolved in ethanol (5.00 mL), then hydroxylamine hydrochloride (481.9 mg, 6.94 mmol) and pyridine (548.62 mg, 6.94 mmol) were successively added. The reaction solution was heated to 80° C. and reacted for 12 hours. After the reaction was complete, the reaction was quenched by addition of water (10 mL) and the aqueous phase was extracted with dichloromethane (5 mL×2). The combined organic phase was washed successively with dilute hydrochloric acid (1M, 5 mL×2) and saturated brine (10 mL×2). The organic phase was dried over anhydrous sodium sulfate, filtered and concentrated in vacuo. The residue was purified by thin layer chromatography (eluent: petroleum ether/ethyl acetate=10/1) to give product 30-4 as a white solid (150.00 mg, yield: 71.29%). MS (m/z): 304.1 (M+1). $^1$H NMR (400 MHz, CD$_3$OD) δ 8.29 (s, 1H), 6.60 (s, 1H), 6.46 (dd, J=2.4, 11.2 Hz, 1H), 5.70-5.52 (m, 1H), 5.30 (d, J=3.2 Hz, 1H), 4.24 (d, J=4.8 Hz, 1H), 3.78 (s, 3H), 2.88-2.62 (m, 2H), 2.51-2.20 (m, 5H), 1.90-1.75 (m, 1H), 1.38-1.24 (m, 2H), 0.95-0.86 (m, 1H), 0.85 (d, J=4.8 Hz, 3H).

Step 5: Preparation of Compound 30-5

Compound 30-4 (150.00 mg, 494.45 umol) was dissolved in ethanol (2.00 mL), then Raney Nickel (84.72 mg) and NH$_3$.H$_2$O (100.00 uL) were added. After the reaction system was purged with nitrogen for three times, hydrogen gas was introduced. The reaction was carried out under 50 Psi at 80° C. for 12 hours. The reaction solution was filtered through celite and concentrated in vacuo to give crude product 30-5 (180 mg) as a pale yellow oil. $^1$H NMR (400 MHz, CD$_3$OD) δ 6.67 (br. s., 1H), 6.54-6.47 (m, 1H), 3.77 (s, 3H), 3.28-3.22 (m, 1H), 2.81-2.67 (m, 2H), 2.41-2.27 (m, 1H), 2.08-1.84 (m, 5H), 1.59-1.27 (m, 7H), 1.20 (t, J=7.2 Hz, 3H).

Step 6: Preparation of Compound 30

Compound 30-5 (150 mg, 514.76 umol) was dissolved in hydrobromic acid (5.00 mL) and the reaction solution was stirred at 100° C. for 5 hours. After being cooled down, the reaction solution was concentrated in vacuo to give the crude product. The crude product was purified by HPLC preparative column to give product 30 as a yellow oil (31.71 mg, yield: 22.21%). MS (m/z): 278.0 (M+1). 1H NMR (400 MHz, CD$_3$OD) δ 6.60 (s, 1H), 6.43 (dd, J=2.4, 11.2 Hz, 1H), 3.79 (d, J=2.8 Hz, 1H), 2.88-2.73 (m, 2H), 2.59 (dd, J$_1$=2.8 Hz, J$_2$=5.0 Hz, 1H), 2.05-1.94 (m, 1H), 1.93-1.67 (m, 4H), 1.65-1.29 (m, 4H), 1.18 (td, J$_1$=5.2 Hz, J$_2$=10.0 Hz, 2H), 0.92-0.76 (m, 4H).

Example 31: Preparation of Compound 31

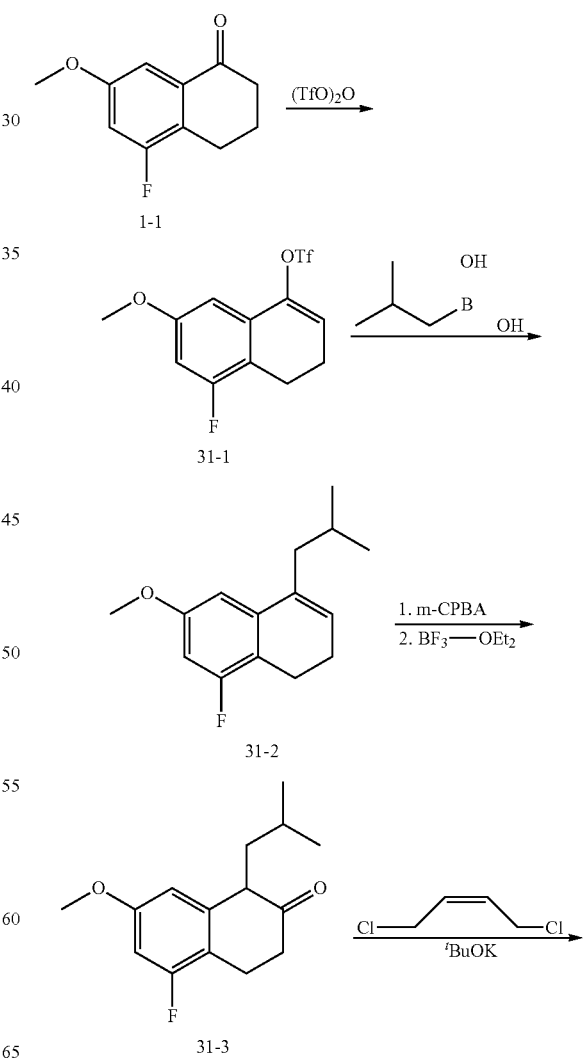

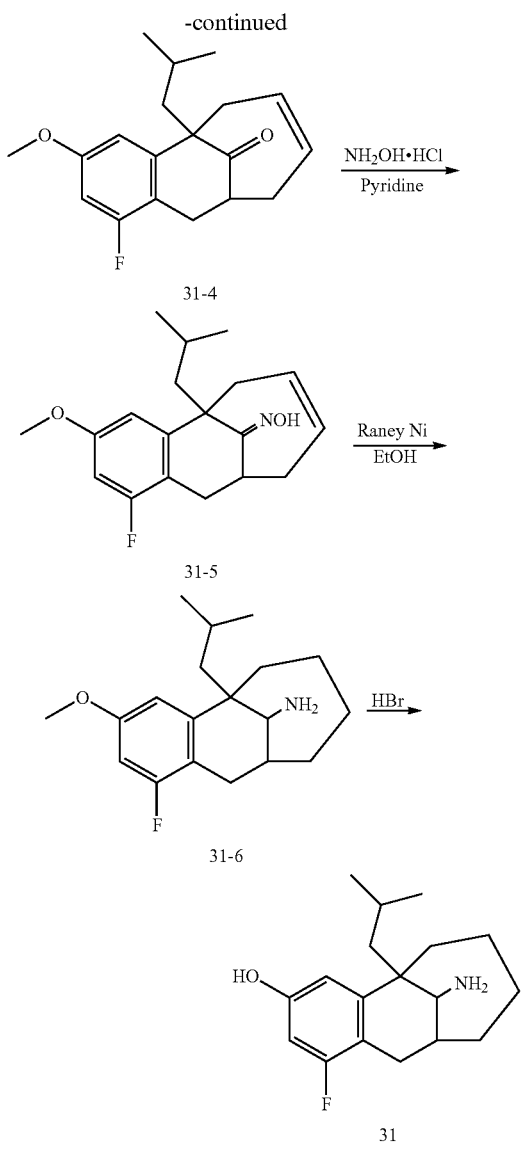

Step 1: Preparation of Compound 31-1

Compound 1-1 (5.00 g, 25.75 mmol) was dissolved in dichloromethane (20.00 mL), then trifluoromethanesulfonic anhydride (8.72 g, 30.90 mmol) and sodium carbonate (5.46 g, 51.50 mmol) were successively added, the reaction solution was stirred at 25° C. for 12 hours. After the reaction was complete, water (30 mL) was added to quench the reaction. The aqueous phase was extracted with dichloromethane (30 mL×2). The combined organic phase was washed with saturated brine (30 mL×2), dried over anhydrous sodium sulfate and concentrated in vacuo. The residue was purified by thin layer chromatography (eluent: petroleum ether/ethyl acetate=10/1) to give product 31-1 (7.50 g, yield: 89.28%) as a pale yellow oil. $^1$H NMR (400 MHz, CDCl$_3$) δ 6.74 (d, J=2.0 Hz, 1H), 6.60 (dd, $J_1$=2.4 Hz, $J_2$=10.8 Hz, 1H), 6.08 (t, J=4.8 Hz, 1H), 3.80 (s, 3H), 2.88-2.73 (m, 2H), 2.52 (dt, $J_1$=4.8 Hz, $J_2$=8.4 Hz, 2H).

Step 2: Preparation of Compound 31-2

Compound 31-1 (3.00 g, 9.20 mmol) was dissolved in toluene (20.00 mL), then isobutylboronic acid (4.69 g, 46.00 mmol), Pd(PPh$_3$)$_4$ (531.56 mg, 460.00 umol), KF (1.28 g, 22.08 mmol) and Cs$_2$CO$_3$ (2.40 g, 7.36 mmol) were successively added. The reaction system was purged with nitrogen for three times, then the reaction solution was stirred at 80° C. for 12 hours. After being cooled down, the reaction solution was filtered through celite and the filtrate was diluted with 20 mL water. The aqueous phase was extracted with dichloromethane (20 mL×2). The combined organic phase was washed with 20 mL saturated brine, dried over anhydrous sodium sulfate, filtered, and concentrated in vacuo. The residue was purified by thin layer chromatography (eluent: petroleum ether/ethyl acetate=10/1) to give compound 31-2 (600.00 mg, yield: 27.83%) as a colorless oil. $^1$H NMR (400 MHz, CDCl$_3$) δ 6.62 (d, J=2.0 Hz, 1H), 6.48 (dd, $J_1$=11.2 Hz, $J_2$=2.4 Hz, 1H), 5.88 (t, J=4.4 Hz, 1H), 3.82-3.78 (m, 3H), 2.69 (t, J=8.0 Hz, 2H), 2.28-2.25 (m, 2H), 2.24-2.20 (m, 2H), 1.93-1.73 (m, 2H), 0.91 (d, J=6.4 Hz, 6H).

Step 3: Preparation of Compound 31-3

Compound 31-2 (600.00 mg, 2.56 mmol) was dissolved in dichloromethane (2.00 mL), then Na$_2$CO$_3$ (407.11 mg, 3.84 mol) and m-CPBA (530.28 mg, 3.07 mmol) were successively added under an ice bath, the internal temperature was maintained within 0-5° C. and the mixture was stirred for 1 hour. The reaction was quenched by addition of saturated Na$_2$SO$_3$ (5 mL) solution. The aqueous phase was extracted with dichloromethane (10 mL×3) and the combined organic phase was dried over anhydrous Na$_2$SO$_4$ and filtered. The residue obtained after concentration in vacuo was dissolved in dichloromethane (5.00 mL). BF$_3$.Et$_2$O (68.04 mg, 479.00 umol) was added to the dichloromethane solution under an ice bath, and the mixture was stirred at the same temperature for 0.5 hours. The reaction was quenched by addition of saturated NaHCO$_3$ (3 mL) and the aqueous phase was extracted with dichloromethane (5 mL×3). The combined organic phase was washed with saturated brine (10 mL×2), dried over sodium sulfate, filtered and concentrated in vacuo. The residue was purified by silica gel column chromatography (eluent: petroleum ether/ethyl acetate=10/1) to give product 31-3 as a pale yellow oil (0.4 g, yield: 33.36%). MS (m/z): 251.0 (M+1). $^1$H NMR (400 MHz, CDCl$_3$) δ 6.53 (dd, $J_1$=2.4 Hz, $J_2$=11.2 Hz, 1H), 6.46 (s, 1H), 3.79 (s, 3H), 3.44 (t, J=7.2 Hz, 1H), 3.21-2.93 (m, 2H), 2.69 (td, J=5.6 Hz, $J_2$=17.2 Hz, 1H), 2.51-2.29 (m, 1H), 1.74-1.67 (m, 1H), 1.65-1.53 (m, 3H), 0.95 (t, J=6.8 Hz, 6H).

Step 4: Preparation of Compound 31-4

Compound 31-3 (300.00 mg, 1.20 mmol) was dissolved in THF (2.00 mL) under an ice bath. After the reaction system was purged with nitrogen for three times, potassium tert-butoxide (161.38 mg, 1.44 mmol) was added. After the reaction solution was stirred at the same temperature for 1 hour, the reaction solution was slowly added to a solution of cis-1,4-dichloro-2-butene (225.00 mg, 1.80 mmol) in THF (2.00 mL). After reacting at 25° C. for 12 hours, t-BuOK (161.38 mg, 1.44 mmol) was added, then the temperature was raised to 60° C. and the reaction was continued for 6 hours, the reaction solution was slowly poured into water (10 mL) to be quenched. The aqueous phase was extracted with dichloromethane (10 mL×2). The combined organic phase was dried over anhydrous sodium sulfate, filtered and concentrated in vacuo. The residue was seperated and purified by thin layer chromatography (eluent: petroleum ether/ethyl acetate=10/1) to give product 31-4 as a pale yellow oil (200.00 mg, yield: 55.12%). $^1$H NMR (400 MHz, CDCl$_3$) δ 6.49 (s, 2H), 5.71-5.61 (m, 1H), 5.37-5.26 (m, 1H), 3.77 (s, 3H), 3.14-3.04 (m, 1H), 3.03-2.97 (m, 2H), 2.56 (dd, J=8.4 Hz, $J_2$=13.6 Hz, 1H), 2.40 (dd, J=7.6 Hz, $J_2$=15.6 Hz, 1H), 2.32-2.24 (m, 2H), 2.13-2.03 (m, 1H), 1.70 (dd, $J_1$=5.6 Hz, $J_2$=13.6 Hz, 1H), 1.46-1.30 (m, 1H), 0.74-0.59 (m, 6H).

Step 5: Preparation of Compound 31-5

Compound 31-4 (200.00 mg, 661.42 umol) was dissolved in ethanol (1.00 mL), then hydroxylamine hydrochloride (459.62 mg, 6.61 mmol) and pyridine (523.18 mg, 6.61 mmol) were successively added. The reaction was heated to 80° C. and reacted for 12 hours, then quenched by addition of water (10 mL). The aqueous phase was extracted with dichloromethane (5 mL×2). The combined organic phase was washed successively with dilute hydrochloric acid (1M, 5 mL×2) and saturated brine (10 mL×2). The organic phase was dried over anhydrous sodium sulfate, filtered and concentrated in vacuo. The residue was purified by thin layer chromatography (eluent: petroleum ether/ethyl acetate=10/1) to give product 31-5 as a white solid (150.00 mg, yield: 71.45%). MS (m/z): 318.1 (M+1). $^1$H NMR (400 MHz, CD$_3$OD) δ 6.58 (s, 1H), 6.46 (dd, $J_1$=2.4 Hz, $J_2$=11.2 Hz, 1H), 5.61-5.51 (m, 1H), 5.23 (br. s., 1H), 4.31-4.05 (m, 1H), 3.78 (s, 3H), 2.95-2.70 (m, 2H), 2.59-2.38 (m, 3H), 2.31-2.15 (m, 2H), 1.78 (dd, $J_1$=6.4 Hz, $J_2$=13.6 Hz, 1H), 1.63-1.58 (m, 1H), 0.78 (d, J=6.4 Hz, 3H), 0.58 (d, J=6.8 Hz, 3H).

Step 6: Preparation of Compound 31-6

Compound 31-5 (150.00 mg, 472.59 umol) was dissolved in ethanol (2.00 mL), then Raney nickel (80.97 mg) and NH$_3$.H$_2$O (100.00 uL) were added. After the reaction system was purged with nitrogen for three times, hydrogen gas was introduced. The reaction was carried out under 50 Psi at 80° C. for 12 hours. The reaction solution was filtered through celite and concentrated in vacuo to give the crude product 31-6 (130 mg) as a pale yellow oil. MS (m/z): 306.1 (M+1). $^1$H NMR (400 MHz, CD$_3$OD) δ 6.71 (s, 1H), 6.52 (dd, J=2.4, 11.2 Hz, 1H), 3.78 (s, 3H), 2.79-2.72 (m, 2H), 2.47-2.29 (m, 1H), 2.13-1.92 (m, 3H), 1.88-1.37 (m, 8H), 1.17 (d, J=6.4 Hz, 1H), 0.92 (d, J=6.8 Hz, 3H), 0.51 (d, J=6.8 Hz, 3H).

Step 7: Preparation of Compound 31

Compound 31-6 (100.00 mg, 327.41 umol) was dissolved in hydrobromic acid (2.00 mL) and the solution was stirred at 100° C. for 5 hours. After being cooled down, the reaction solution was concentrated in vacuo to give the crude product. The crude product was purified by HPLC preparative column to give product 31 as yellow oil (9.12 mg, yield: 9.56%). MS (m/z): 292.0 (M+1). $^1$H NMR (400 MHz, CD$_3$OD) δ 6.66 (d, J=1.6 Hz, 1H), 6.47 (dd, $J_1$=2.4 Hz, $J_2$=11.2 Hz, 1H), 3.72 (d, J=2.4 Hz, 1H), 2.8 (d, J=7.2 Hz, 1H), 2.64 (br. s., 1H), 2.57-2.43 (m, 1H), 2.15-1.88 (m, 4H), 1.84-1.70 (m, 1H), 1.68-1.41 (m, 5H), 1.19 (d, J=6.4 Hz, 3H), 1.13 (dt, $J_1$=4.4 Hz, $J_2$=7.5 Hz, 1H), 1.06 (d, J=6.4 Hz, 3H).

Example 32: Preparation of Compound 32 and Compound 33

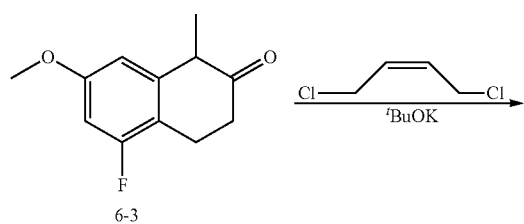

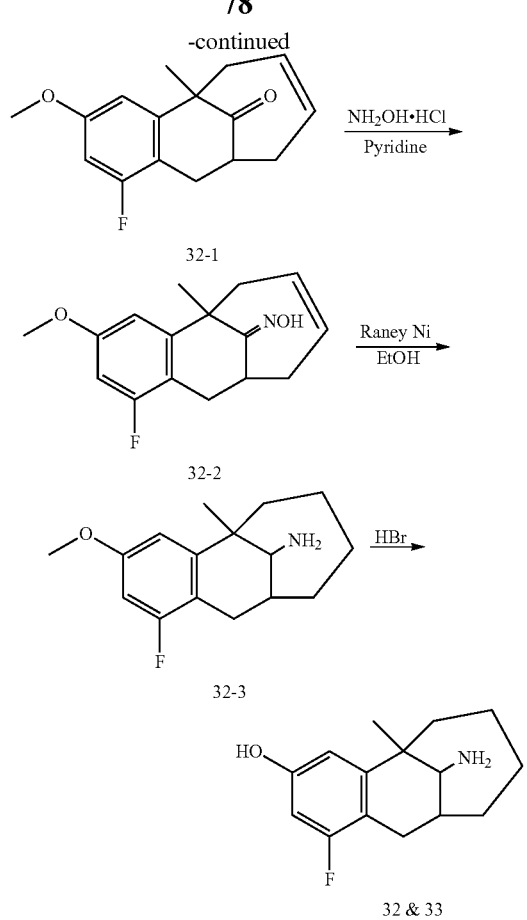

Step 1: Preparation of Compound 32-1

Compound 6-3 (1.50 g, 7.20 mmol) was dissolved in THF (10.00 mL) under an ice bath, and the reaction system was purged with nitrogen for three times, then potassium tert-butoxide (969.98 mg, 8.64 mmol) was added. After being stirred at the same temperature for 1 hour, the reaction solution was slowly added to a solution of cis-1,4-dichloro-2-butene (1.80 g, 14.41 mmol) in THF (5.00 mL). After reacting at 25° C. for 12 hours, t-BuOK (1.21 g, 10.81 mmol) was added, then the temperature was raised to 60° C. and the reaction was continued for 6 hours. The reaction solution was slowly poured into water (5 mL) to be quenched. The aqueous phase was extracted with dichloromethane (5 mL×2). The combined organic phase was washed with saturated brine, dried over sodium sulfate, filtered and concentrated in vacuo. The residue was purified by silica gel column chromatography (eluent: petroleum ether/ethyl acetate=10/1) to give product 32-1 as a pale yellow oil (1.2 g, yield: 64.0%). MS (m/z): 260.9 (M+1). $^1$H NMR (400 MHz, CDCl$_3$) δ 6.57 (s, 1H), 6.45-6.51 (m, 1H), 5.80 (ddd, $J_1$=14.8 Hz, $J_2$=7.6 Hz, $J_3$=3.2 Hz, 1H), 5.38-5.59 (m, 1H), 3.78 (s, 3H), 3.02-3.07 (m, 1H), 2.93-3.01 (m, 1H), 2.34-2.47 (m, 2H), 2.26 (br. s., 1H), 2.09-2.18 (m, 1H), 1.56 (s, 3H).

Step 2: Preparation of Compound 32-2

Compound 32-1 (900.00 mg, 3.46 mmol) was dissolved in pyridine (5.00 mL), and hydroxylamine hydrochloride (2.40 g, 34.60 mmol) was added, then the temperature was raised to 100° C. and the reaction was continued for 12 hours. After the reaction was complete, the reaction was quenched by addition of water (10 mL) and the aqueous phase was extracted with dichloromethane (10 mL×2). The combined organic phase was adjusted to pH 5-6 with hydrochloric acid and washed twice with water. The organic phase was dried over anhydrous sodium sulfate, filtered and concentrated in vacuo. Ethyl acetate (2 mL) was added and then the mixture was allowed to stand overnight, precipitate was precipitated. The mixture was filtered to give compound 32-2 as a white solid (400.00 mg, yield: 81.3%). MS (m/z): 275.9 (M+1). $^1$H NMR (400 MHz, CD$_3$OD) δ 6.70 (br. s., 2H), 6.55 (dd, J=11.2, 2.4 Hz, 1H), 6.44-6.50 (m, 1H), 5.67 (td, J$_1$=7.6 Hz, J$_2$=3.64 Hz, 1H), 5.32 (td, J$_1$=7.6 Hz, J$_2$=4.4 Hz, 1H), 4.05-4.37 (m, 2H), 3.75 (s, 3H), 3.78 (s, 3H), 2.74-2.80 (m, 3H), 2.41-2.57 (m, 2H), 2.18-2.32 (m, 2H), 2.03-2.16 (m, 2H), 1.60 (s, 3H), 1.44 (s, 3H), 0.77-1.24 (m, 3H).

Step 3: Preparation of Compound 32-3

Compound 32-2 (350.00 mg, 1.27 mmol) was dissolved in ethanol (2.00 mL), then Raney nickel (217.60 mg), NH$_3$·H$_2$O (4.45 mg, 127.00 umol) was added. After the reaction system was purged with nitrogen for three times, hydrogen gas was introduced. The reaction was carried out under 50 Psi at 70° C. for 12 hours. The reaction solution was filtered through celite and concentrated in vacuo to give the crude product 32-3 (500.00 mg) as a pale yellow oil. MS (m/z): 263.9 (M+1). $^1$H NMR (400 MHz, CD$_3$OD) δ 6.71 (d, J=19.2 Hz, 1H), 6.47-6.57 (m, 1H), 3.77 (d, J=2.8 Hz, 3H), 2.98-3.07 (m, 1H), 2.71-2.95 (m, 1H), 2.32-2.54 (m, 1H), 1.79-2.14 (m, 2H), 1.38-1.73 (m, 4H), 1.35 (d, J=9.2 Hz, 3H), 0.84-1.18 (m, 1H).

Step 4: Preparation of Compound 32 and Compound 33

Compound 32-3 (450.00 mg, 1.71 mmol) was dissolved in hydrobromic acid (2.00 mL) and the reaction solution was stirred at 100° C. for 2 hours. After being cooled down, the reaction solution was concentrated in vacuo to give the crude product. The crude product was purified by HPLC preparative column to give two epimers as 32 (40 mg, yield: 9.38%) and 33 (45 mg, yield: 10.56%).

Compound 32: MS (m/z): 249.9 (M+1). $^1$H NMR (400 MHz, CD$_3$OD) δ 6.66 (d, J=1.24 Hz, 1H), 6.43 (dd, J$_1$=11.2 Hz, J$_2$=2.4 Hz, 1H), 3.60 (d, J=3.2 Hz, 1H), 2.72-3.02 (m, 2H), 2.57 (br. s., 1H), 1.77-2.08 (m, 3H), 1.44-1.68 (m, 3H), 1.42 (s, 3H), 1.35-1.41 (m, 1H), 1.02-1.22 (m, 1H), Compound 33: MS (m/z): 249.9 (M+1). $^1$H NMR (400 MHz, CD$_3$OD) δ 6.63 (d, J=1.20 Hz, 1H), 6.45 (dd, J$_1$=11.2 Hz, J$_2$=2.24 Hz, 1H), 3.59 (d, J=3.2 Hz, 1H), 2.68-2.76 (m, 2H), 2.48-2.61 (m, 1H), 2.17 (s, 1H), 1.89-2.05 (m, 1H), 1.61-1.82 (m, 2H), 1.44-1.59 (m, 2H), 1.36-1.43 (m, 3H), 1.14-1.28 (m, 1H), 0.89-1.07 (m, 1H).

Example 34: Preparation of Compound 34

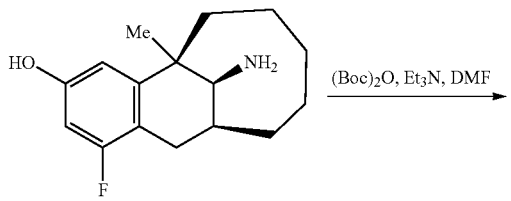

21

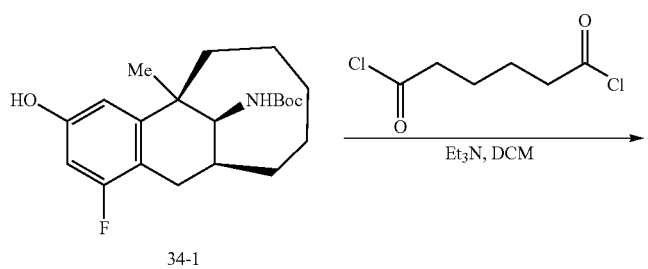

34-1

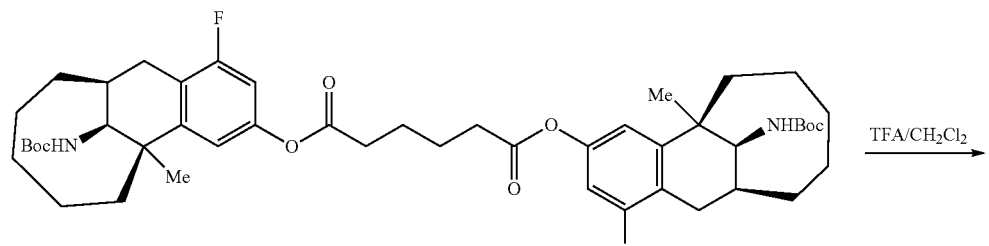

34-2

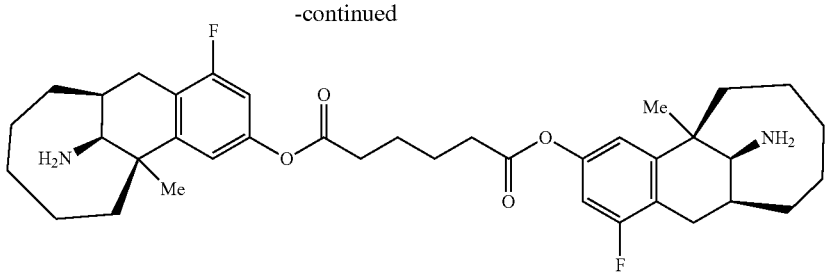

34

Step 1: Preparation of Compound 34-1

Compound 21 (3 g, 11.39 mmol) and triethylamine (1.38 g, 13.67 mmol) were dissolved in DMF (10 mL), then (Boc)$_2$O (2.98 g, 13.67 mmol) was added. The reaction solution was stirred at 15° C. for 1 hour, then poured into water to be quenched, and the aqueous phase was extracted with ethyl acetate (20 mL×2). The combined organic phase was washed with water (20 mL) and saturated brine (20 mL), dried over anhydrous sodium sulfate, filtered and concentrated in vacuo to give the crude product as a brown oil. The crude product was purified by silica gel column chromatography (eluent: dichloromethane/methanol=100/1 to 20/1) to give product 34-1 (2.9 g) as a brown oil. MS (m/z): 308.1 (M-56+1). $^1$H NMR (400 MHz, CDCl$_3$) δ 6.50 (s, 1H), 6.43 (dd, J$_1$=2.0 Hz, J$_2$=10.4 Hz, 1H), 5.44 (br. s., 1H), 4.95 (d, J=10.4 Hz, 1H), 4.05 (dd, J$_1$=5.2 Hz, J$_2$=10.4 Hz, 1H), 2.89-2.73 (m, 2H), 2.36 (br. s., 1H), 1.87-1.49 (m, 15H), 1.29 (s, 3H), 1.01-0.81 (m., 3H).

Step 2: Preparation of Compound 34-2

Compound 34-1 (363 mg, 998.71 umol) was dissolved in dichloromethane (2 mL), then adipoyl chloride (73 mg, 399.48 umol) and triethylamine (60 mg, 599.22 umol) were added. The reaction solution was stirred at 15° C. for 2 hours, then poured into water to be quenched, and the aqueous phase was extracted with ethyl acetate (20 mL×2). The combined organic phase was washed with saturated brine, dried over anhydrous sodium sulfate, filtered and concentrated in vacuo to give the crude product as a dark yellow oil. The crude product was purified by silica gel column chromatography (eluent: petroleum ether/ethyl acetate=10/1 to 6/1) to give product 34-2 (250 mg) as a pale yellow oil. MS (m/z): 859.8 (M+1).

The following compound was prepared according to a method similar to that of compound 34-2:

| Compound number | Structure | Spectrogram |
|---|---|---|
| 35-2 | ![structure] | MS (m/z): 887.5 (M + 23). |

Step 3: Preparation of Compound 34

Compound 34-2 (250 mg, 298.67 umol) was dissolved in dichloromethane (10 mL) and trifluoroacetic acid (1.5 mL) was added dropwise. After the addition was complete, the mixture was stirred at 15° C. for 1 hour. Saturated aqueous NaHCO$_3$ solution was added to quench the reaction, the pH was adjusted to approximately 7, and the aqueous phase was extracted with ethyl acetate (20 mL×2). The combined organic phase was washed with water (20 mL) and saturated brine (20 mL), dried over anhydrous sodium sulfate, filtered and concentrated in vacuo to give the crude product as a dark yellow oil. The crude product was purified by high performance liquid phase preparative column (formic acid system) to give the formate salt of compound 34 (32 mg, yield: 16.8%). MS m/z: 659.6 [M+23]$^+$. $^1$H NMR (400 MHz, CDCl$_3$) δ 8.40-8.26 (m, 2H), 6.73 (s, 2H), 6.69 (d, J=9.6 Hz, 2H), 3.35 (br. s., 2H), 2.88 (br. s., 4H), 2.60-2.46 (br. s., 6H), 1.84-1.78 (m, 10H), 1.72-1.48 (m, 10H), 1.38 (s, 6H), 1.13-0.98 (m, 2H), 0.79 (br. s., 2H).

The following compound was prepared according to a method similar to that of compound 34:

| Compound number | Structure | Spectogram |
|---|---|---|
| Compound 35 | (structure shown) | $^1$H NMR (400 MHz, CDCl$_3$): δ 8.42 (br. s., 1H), 6.76-6.60 (m, 4H), 3.42-3.31 (m, 2H), 2.95-2.77 (m, 4H), 2.60-2.40 (m, 6H), 1.88-1.44 (br. s., 22H), 1.38 (s, 6H), 1.05 (q, J = 11.6 Hz, 2H), 0.79 (br. s., 4H), MS m/z: 333.4 [M/2 + 1]$^+$, 665.4 [M + 1]$^+$ |

Example 36: Preparation of Compound 36

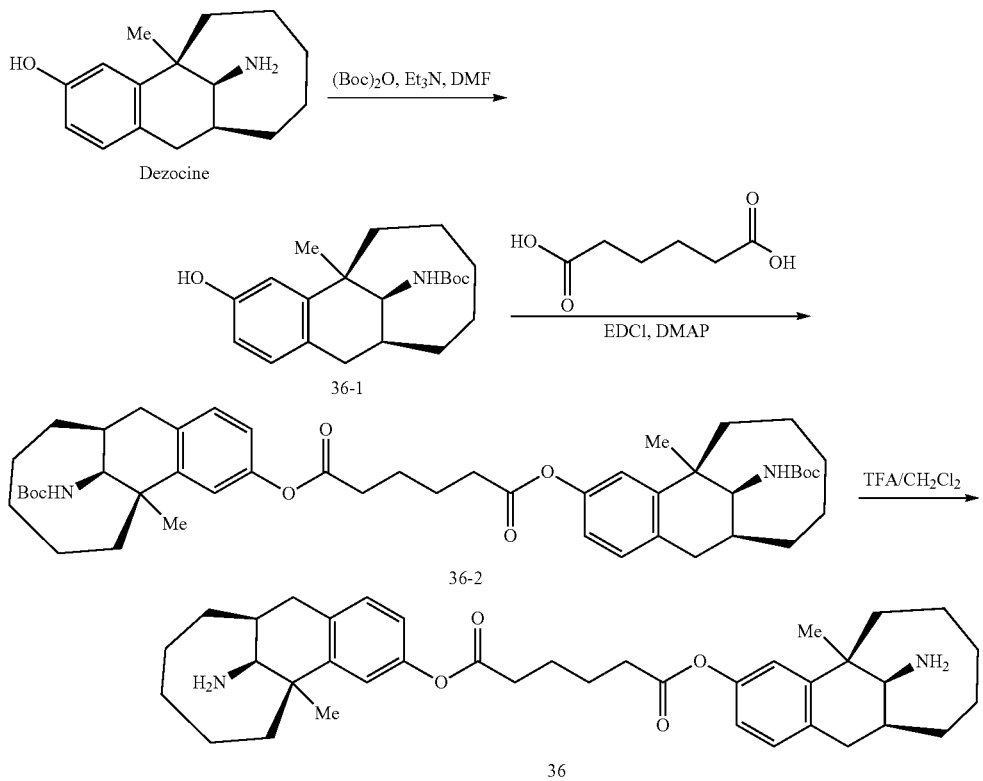

Step 1: Preparation of Compound 36-1

Dezocine (1.00 g, 4.08 mmol) and triethylamine (824.84 mg, 8.15 mmol) were dissolved in DMF (8 mL), then (Boc)$_2$O (1.07 g, 4.89 mmol) was added. After being stirred at 25° C. for 1.5 hours, the reaction solution was poured into water to be quenched and the aqueous phase was extracted with dichloromethane (15 mL×4). The combined organic phases were washed with saturated brine, dried over anhydrous sodium sulfate, filtered and concentrated in vacuo to give the crude product. The crude product was purified by silica gel column chromatography (eluent: petroleum ether/ethyl acetate=8/1) to give product 36-1 (2.9 g). $^1$H NMR (400 MHz, CD$_3$OD): δ 6.92 (d, J=8.4 Hz, 1H), 6.68 (d, J=2.4 Hz, 1H), 6.60 (dd, J$_1$=2.4, Hz, J$_2$=8.4 Hz, 1H), 6.14 (d, J=9.6 Hz, 1H), 4.04 (dd, J$_1$=5.2 Hz, J$_2$=10.4 Hz, 1H), 3.15 (dd, J$_1$=7.2 Hz, J$_2$=16.4 Hz, 1H), 2.65 (d, J=16.4 Hz, 1H), 2.24 (br. s., 1H), 1.82-1.68 (m, 4H), 1.51 (s, 12H), 1.29 (s, 3H), 1.23-1.11 (m, 1H), 1.08-0.97 (m, 1H), 0.95-0.85 (m, 2H).

Step 2: Preparation of Compound 36-2

Compound 36-1 (100.00 mg, 289.46 umol) and adipic acid (19.21 mg, 131.45 umol) were dissolved in dichloromethane (2 mL) and the solution was cooled to 25° C., 4-dimethylaminopyridine (73 mg, 399.48 umol) and 1-(3-dimethylaminopropyl)-3-ethylcarbodiimide hydrochloride (63.00 mg, 328.63 umol) were successively added. The reaction solution was stirred at 0° C. for 5 hours, then poured into water to be quenched and the aqueous phase was extracted with dichloromethane (10 mL×3). The combined organic phases were washed with saturated brine, dried over anhydrous sodium sulfate, filtered and concentrated in vacuo to give the crude product 36-2 (108 mg). The crude product was used in the next step without further purification. MS (m/z): 823.5 (M+1).

The following compounds were prepared by similar method with Compound 36-2:

| Compound number | Structure | Spectrogram |
|---|---|---|
| 37-1 | 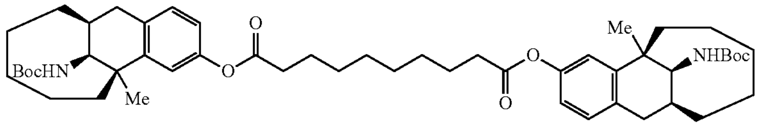 [SMILES: CC(C)(C)OC(=O)N[C@H]1[C@H]2CCCCC[C@]1(C)c1cc(OC(=O)CCCCCCCCC(=O)Oc3ccc4c(c3)[C@@]3(C)CCCCC[C@@H](C4)[C@@H]3NC(=O)OC(C)(C)C)ccc1C2] | MS (m/z): 879.6 (M + 23). |
| 38-1 | 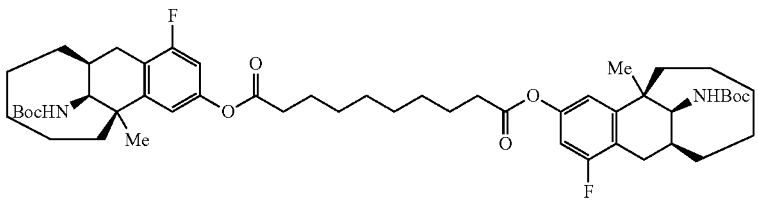 [SMILES: CC(C)(C)OC(=O)N[C@H]1[C@H]2CCCCC[C@]1(C)c1cc(OC(=O)CCCCCCCCC(=O)Oc3cc(F)c4c(c3)[C@@]3(C)CCCCC[C@@H](C4)[C@@H]3NC(=O)OC(C)(C)C)cc(F)c1C2] | MS (m/z): 915.5 (M + 23). |
| 39-1 | 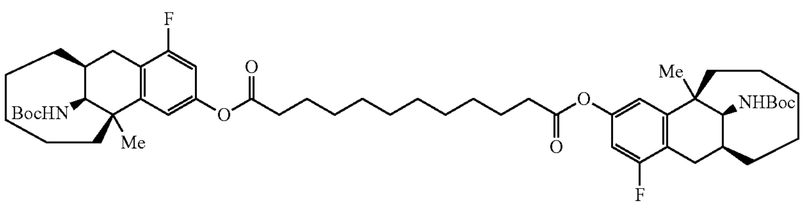 [SMILES: CC(C)(C)OC(=O)N[C@H]1[C@H]2CCCCC[C@]1(C)c1cc(OC(=O)CCCCCCCCCCC(=O)Oc3cc(F)c4c(c3)[C@@]3(C)CCCCC[C@@H](C4)[C@@H]3NC(=O)OC(C)(C)C)cc(F)c1C2] | MS (m/z): 943.5 (M + 23). |
| 40-1 | 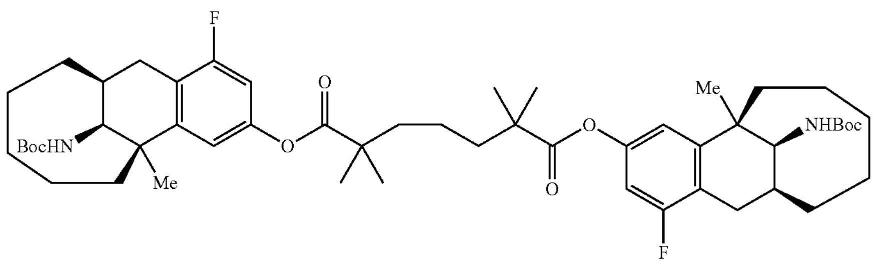 [SMILES: CC(C)(C)OC(=O)N[C@H]1[C@H]2CCCCC[C@]1(C)c1cc(OC(=O)C(C)(C)CCCC(C)(C)C(=O)Oc3cc(F)c4c(c3)[C@@]3(C)CCCCC[C@@H](C4)[C@@H]3NC(=O)OC(C)(C)C)cc(F)c1C2] | MS (m/z): 929.5 (M + 23). |
| 41-1 | 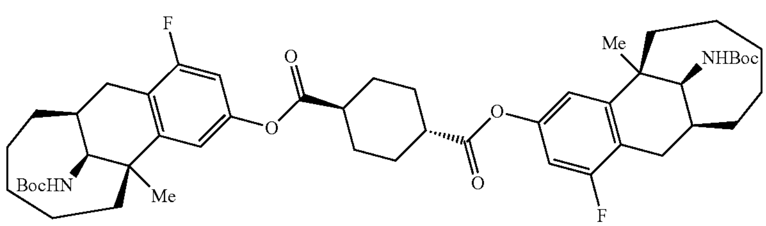 [SMILES: CC(C)(C)OC(=O)N[C@H]1[C@H]2CCCCC[C@]1(C)c1cc(OC(=O)[C@H]3CC[C@H](C(=O)Oc4cc(F)c5c(c4)[C@@]4(C)CCCCC[C@@H](C5)[C@@H]4NC(=O)OC(C)(C)C)CC3)cc(F)c1C2] | MS (m/z): 885.5 (M + 23). |

Step 3: Preparation of Compound 36

Compound 36-2 (108.0 mg, 134.82 umol) was dissolved in dichloromethane (2 mL), then trifluoroacetic acid (15.4 mg, 134.82 umol) was added at 10° C. The reaction solution was stirred at 10° C. for 4 hours, then quenched by addition of 5% NaHCO$_3$ aqueous solution. The pH was adjusted to approximately 7, and the aqueous phase was extracted with dichloromethane (10 mL×4). The combined organic phases were washed with saturated brine, dried over anhydrous sodium sulfate, filtered and concentrated in vacuo to give the crude product. The crude product was purified by high performance liquid preparative column (neutral system) to give compound 36 as a colorless oil (27 mg, yield: 31.8%). MS (m/z): 601.4 (M+1). $^1$H NMR (400 MHz, CDCl$_3$): δ 7.07 (d, J=8.4 Hz, 2H), 6.92 (d, J=2.4 Hz, 2H), 6.83 (dd, J$_1$=2.4 Hz, J$_2$=8.4 Hz, 2H), 3.21-3.11 (m, 4H), 2.70 (d, J=17.2 Hz, 2H), 2.63 (br. s., 4H), 2.24 (br. s., 2H), 2.06-1.96 (m, 2H), 2.01-1.88 (m, 4H), 1.79-1.53 (m, 12H), 1.35 (s, 6H), 1.06-0.94 (m, 2H), 0.91-0.72 (m, 4H).

The following compounds were prepared by similar method with Compound 36:

| Compound number | Structure | Spectrogram |
|---|---|---|
| Compound 37 | 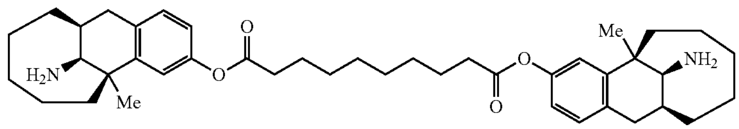 [SMILES: C[C@@]12CCCCC[C@@H](Cc3ccc(OC(=O)CCCCCCCCC(=O)Oc4ccc5c(c4)[C@@]4(C)CCCCC[C@@H](C5)[C@@H]4N)cc31)[C@@H]2N] | MS (m/z): 657.5 (M + 1). $^1$H NMR (400 MHz, CDCl$_3$): δ 7.07 (d, J = 8.3 Hz, 2H), 6.91 (d, J = 2.4 Hz, 2H), 6.82 (dd, J$_1$ = 2.4 Hz, J$_2$ = 8.4 Hz, 2H), 3.19-3.10 (m, 4H), 2.70 (d, J = 16.8 Hz, 2H), 2.54 (t, J = 7.6 Hz, 4H), 2.24 (br. s., 2H), 2.05-1.96 (m, 2H), 1.82-1.61 (m, 12H), 1.56-1.42 (m, 12H), 1.35 (s, 6H), 1.07-0.95 (m, 2H), 0.92-0.75 (m, 4H). |
| Compound 38 | 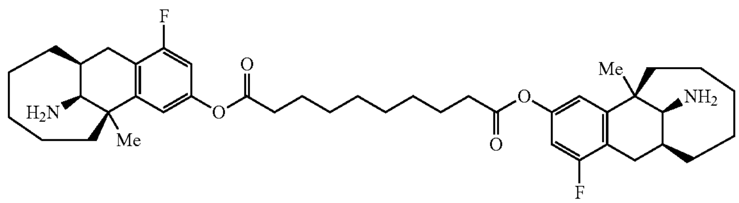 [SMILES: C[C@@]12CCCCC[C@@H](Cc3c(F)cc(OC(=O)CCCCCCCCC(=O)Oc4cc(F)c5c(c4)[C@@]4(C)CCCCC[C@@H](C5)[C@@H]4N)cc31)[C@@H]2N] | MS (m/z): 715.4 (M + 1). $^1$H NMR (400 MHz, CDCl$_3$): δ 6.75-6.61 (m, 4H), 3.35 (d, J = 4.4 Hz, 3H), 2.93-2.80 (m, 4H), 2.58-2.40 (m, 6H), 1.79-1.45 (m, 18H), 1.45-1.27 (m, 14H), 1.07-1.04 (m, 2H), 0.81-0.78 (m, 4H). |
| Compound 39 | 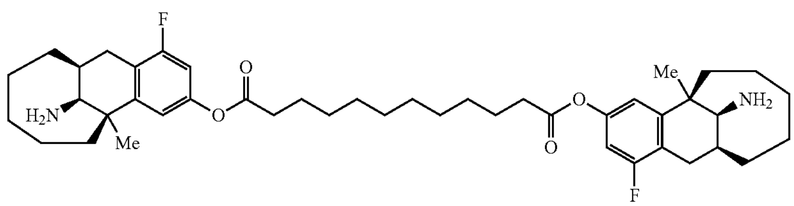 [SMILES: C[C@@]12CCCCC[C@@H](Cc3c(F)cc(OC(=O)CCCCCCCCCCC(=O)Oc4cc(F)c5c(c4)[C@@]4(C)CCCCC[C@@H](C5)[C@@H]4N)cc31)[C@@H]2N] | MS (m/z): 721.4 (M + 1). $^1$H NMR (400 MHz, CDCl$_3$): δ 6.79 (s, 2H), 6.75-6.68 (m, 2H), 3.61 (br. s., 2H), 2.31-2.95 (m, 4H), 2.60-2.57 (m, 6H), 2.23-2.05 (m, 4H), 1.95-1.90 (m, 6H), 1.81-1.73 (m, 4H), 1.68-1.56 (m, 10H), 1.49-1.19 (m, 14H), 0.86 (br. s., 4H) |
| Compound 40 | 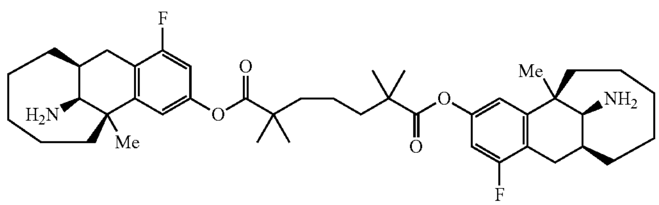 [SMILES: CC(C)(CCCC(C)(C)C(=O)Oc1cc(F)c2c(c1)[C@@]1(C)CCCCC[C@@H](C2)[C@@H]1N)C(=O)Oc1cc(F)c2c(c1)[C@@]1(C)CCCCC[C@@H](C2)[C@@H]1N] | MS (m/z): 729.4 (M + 1). $^1$H NMR (400 MHz, CDCl$_3$): δ 6.84 (s, 2H), 6.72 (dd, J$_1$ = 2.0 Hz, J$_2$ = 10.0 Hz, 2H), 3.60 (br. s., 2H), 3.04-2.91 (m, 4H), 2.55 (br. s., 2H), 1.98-1.90 (m, 4H), 1.85-1.44 (s, 22H), 1.36 (s, 12H), 1.24-1.12 (m, 2H), 0.86-0.82 (m, 4H). |
| Compound 41 | 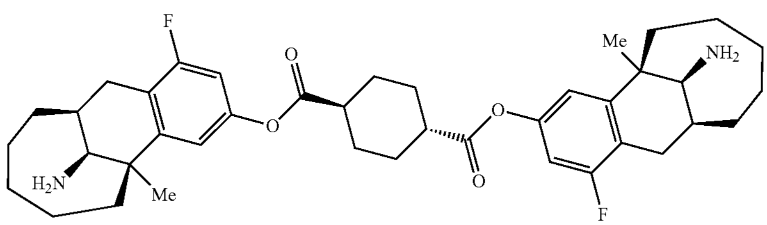 [SMILES: C[C@@]12CCCCC[C@@H](Cc3c(F)cc(OC(=O)[C@H]4CC[C@H](C(=O)Oc5cc(F)c6c(c5)[C@@]5(C)CCCCC[C@@H](C6)[C@@H]5N)CC4)cc31)[C@@H]2N] | MS (m/z): 663.4 (M + 1). $^1$H NMR (400 MHz, CDCl$_3$): δ 6.73 (s, 2H), 6.69-6.64 (m, 2H), 3.22 (d, J = 5.2 Hz, 2H), 2.94-2.82 (m, 4H), 2.40 (br. s., 2H), 2.28 (d, J = 7.6 Hz, 4H), 2.02-1.48 (m, 22H), 1.37 (s, 6H), 1.11-0.96 (m, 2H), 0.84-0.81 (m, 2H). |

Example 42: Preparation of Compound 42

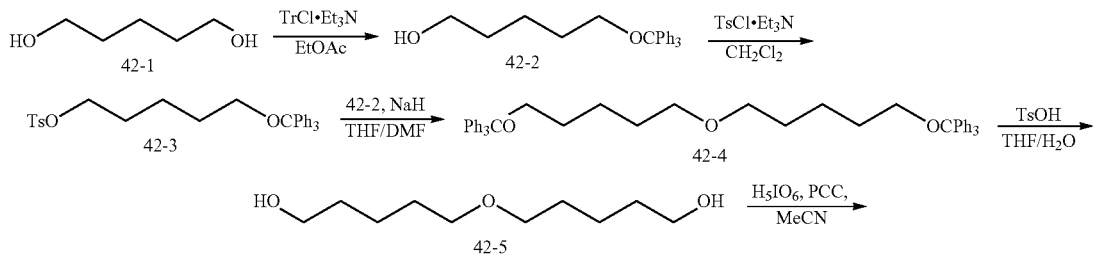

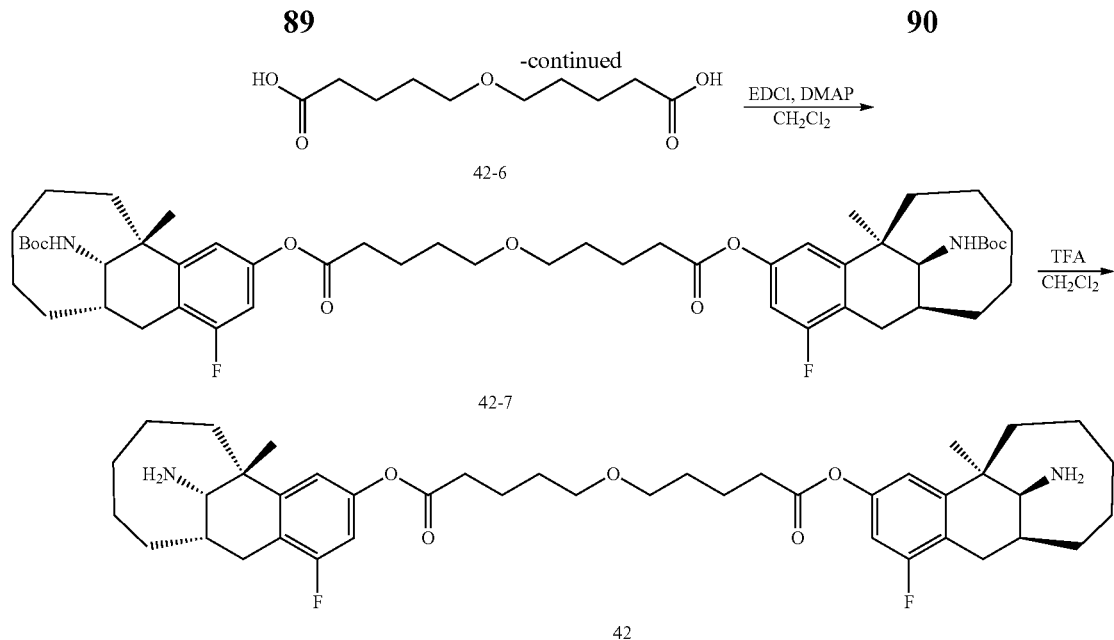

Step 1: Preparation of Compound 42-2

Compound 42-1 (20.00 g, 192.03 mmol) was dissolved in ethyl acetate (200 mL). Triethylamine (8.16 g, 80.65 mmol) and triphenylchloromethane (11.24 g, 40.33 mmol) were successively added under stirring. The solution was slowly heated to reflux, then stirred for 5 hours. After being cooled down, the reaction solution was quenched by being poured into 100 mL water and the aqueous phase was extracted with ethyl acetate (50 mL×3). The combined organic phases were washed with 30 mL water and 30 mL saturated brine, dried over anhydrous sodium sulfate, filtered, and concentrated in vacuo to give the crude product. The crude product was purified by silica gel column chromatography (eluent: petroleum ether/ethyl acetate=20/1 to 3/1) to give 42-2 (20 g) as a colorless liquid. $^1$H NMR (400 MHz, CDCl$_3$) δ 7.46-7.20 (m, 15H), 3.63 (t, J=6.4 Hz, 2H), 3.07 (t, J=6.4 Hz, 2H), 1.76-1.38 (m, 6H).

Step 2: Preparation of Compound 42-3

Compound 42-2 (12.00 g, 34.64 mmol) was dissolved in dichloromethane (200 mL), then 4-dimethylaminopyridine (846 mg, 6.93 mmol), triethylamine (4.56 g, 45.03 mmol) and p-toluenesulfonyl chloride (7.92 g, 41.56 mmol) were successively added. After being stirred at 15° C. for 16 hours, the reaction solution was quenched by being poured into 100 mL water and the aqueous phase was extracted with dichloromethane (50 mL×2). The combined organic phases were washed with 50 mL water and 50 mL saturated brine, dried over anhydrous sodium sulfate, filtered and concentrated in vacuo to give the crude product. The crude product was purified by silica gel column chromatography (eluent: petroleum ether/ethyl acetate=20/1 to 3/1) to give compound 42-3 as a pale yellow viscous liquid (12 g, yield: 69.2%). $^1$H NMR (400 MHz, CDCl$_3$) δ 7.78 (d, J=8.4 Hz, 2H), 7.45-7.17 (m, 17H), 4.00 (t, J=6.4 Hz, 2H), 3.01 (t, J=6.4 Hz, 2H), 2.43 (s, 3H), 1.67-1.49 (m, 4H), 1.45-1.34 (m, 2H).

Step 3: Preparation of Compound 42-4

Compound 42-2 (7.00 g, 20.20 mmol) was dissolved in THF (50 mL). Sodium hydride (1.62 g, 40.40 mmol, 60% purity) was added at 0° C. The solution was heated to 15° C., and stirred for 15 minutes. A solution of 42-3 (12.03 g, 24.04 mmol) in DMF (100 mL) was added. After being stirred at 15° C. for 16 hours, the reaction solution was quenched by being poured into 100 mL water, then the aqueous phase was extracted with ethyl acetate (50 mL×3). The combined organic phases were washed with 20 mL water and 30 mL saturated brine, dried over anhydrous sodium sulfate, filtered, and concentrated in vacuo to give the crude product. The crude product was purified by silica gel column chromatography (eluent: petroleum ether/ethyl acetate=20/1 to 5/1) to give compound 42-4 as a colorless liquid (12.0 g). MS m/z: 697.5 (M+23). $^1$H NMR (400 MHz, CDCl$_3$) δ 7.48-7.20 (m, 30H), 3.38 (t, J=6.8 Hz, 4H), 3.08 (t, J=6.4 Hz, 4H), 1.71-1.60 (m, 4H), 1.59-1.49 (m, 4H), 1.48-1.37 (m, 4H).

Step 4: Preparation of Compound 42-5

Compound 42-4 (12.0 g, 17.78 mmol) was dissolved in the mixed solution of THF (50 mL) and methanol (50 mL), then p-toluenesulfonic acid (612 mg, 3.56 mmol) was added. After being stirred at 15° C. for 16 hours, the reaction solution was concentrated directly under vacuum to give the crude product. The crude product was purified by silica gel column chromatograph (eluent: dichloromethane/methanol=20/1 to 10/1) to give compound 42-5 as a pale yellow liquid (2.50 g, yield: 73.9%). $^1$H NMR (400 MHz, CDCl$_3$) δ 3.64 (t, J=6.4 Hz, 4H), 3.42 (t, J=6.4 Hz, 4H), 1.84-1.55 (m, 8H), 1.49-1.36 (m, 4H).

Step 5: Preparation of Compound 42-6

Periodic acid (3.29 g, 14.45 mmol) was added to acetonitrile (45 mL) and the solution was vigorously stirred at 15° C. for 15 minutes. Then the solution was cooled to 0° C. and added with 42-5 (1.10 g, 5.78 mmol) and PCC (25 mg, 115.60 umol, 0.02 eq). The mixture was heated to 15° C., and stirred for 16 hours. After the precipitate was filtered off, the filtrate was poured into 50 mL half-saturated brine, and the aqueous phase was extracted with ethyl acetate (30 mL×3). The combined organic phases were washed with 40 mL saturated aqueous NaHSO$_3$ solution and 30 mL saturated brine respectively, dried over anhydrous sodium sulfate, filtered, and concentrated in vacuo to give the crude product 42-6 (800.0 mg) as a pale yellow solid. The crude product was directly used in the next step without further purification. ¹H NMR (400 MHz, CDCl₃) δ 3.47-3.41 (m, 4H), 2.47-2.37 (m, 4H), 1.83-1.57 (m, 8H).

Step 6: Preparation of Compound 42-7

Compound 42-6 (300 mg, 1.37 mmol) was dissolved in dichloromethane (20 mL). 4-dimethylaminopyridine (167 mg, 1.37 mmol), 34-1 (1.07 g, 2.95 mmol) and 1-(3-dimethylaminopropyl)-3-ethylcarbodiimide hydrochloride (735 mg, 3.84 mmol) were successively added. The reaction solution was stirred at 15° C. for 16 hours, then quenched by being poured into 30 mL water, and the aqueous phase was extracted with dichloromethane (20 mL×3). The combined organic phases were washed with 10 mL water and 10 mL saturated brine, dried over anhydrous sodium sulfate, filtered and concentrated in vacuo to give the crude product. The crude product was purified by silica gel column chromatography (eluent: petroleum ether/ethyl acetate=10/1 to 3/1) to give compound 42-7 as a colorless viscous solid (323 mg, yield: 26.0%). MS m/z: 931.7 (M+23).

Step 7: Preparation of Compound 42

Compound 42-7 (430 mg, 472.97 umol) was dissolved in dichloromethane (10 mL), then trifluoroacetic acid (1.8 mL) was added. After reacting at 15° C. for 16 hours, the reaction solution was poured to 50 mL ethyl acetate to be diluted poured into, then a saturated aqueous solution of sodium bicarbonate was slowly added to adjust the pH to approximately 7, and the aqueous phase was extracted with ethyl acetate (30 mL×3). The combined organic phases were washed with 20 mL water and 20 mL saturated brine, dried over anhydrous sodium sulfate, filtered, and concentrated in vacuo to give the crude product. The crude product was purified by high performance liquid phase preparative column (HCl system) to give the hydrochloride salt of compound 42 (200 mg, yield: 54.1%). MS m/z: 709.3 (M+1). ¹H NMR (400 MHz, CDCl₃) δ 6.94 (s, 2H), 6.82 (d, J=9.8 Hz, 2H), 3.73 (d, J=4.4 Hz, 2H), 3.53 (t, J=6.0 Hz, 4H), 3.11-2.91 (m, 4H), 2.72-2.55 (m, 6H), 2.04-1.92 (m, 4H), 1.85-1.68 (m, 12H), 1.61 (d, J=9.2 Hz, 6H), 1.51 (s, 6H), 1.30-1.20 (m, 2H), 0.90-0.75 (m, 4H).

Example 43: Preparation of Compound 43

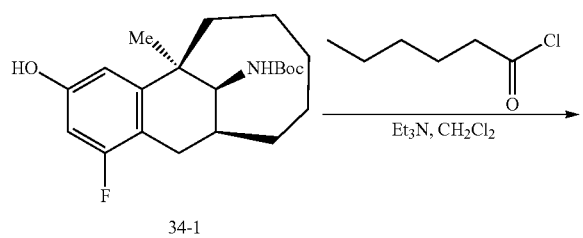

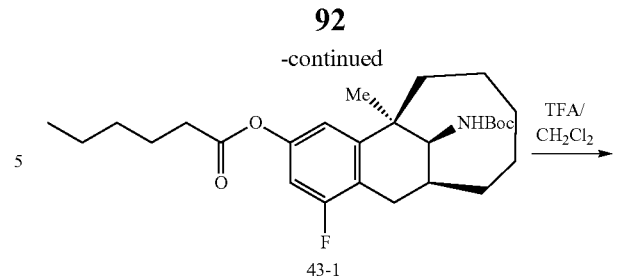

Step 1: Preparation of Compound 43-1

Compound 34-1 (200 mg, 550 umol) was dissolved in dichloromethane (10 mL), then hexanoyl chloride (74 mg, 550 umol) and triethylamine (83 mg, 825 umol) were added. The reaction solution was stirred at 15° C. for 2 hours, then poured into water to be quenched, and the aqueous phase was extracted with ethyl acetate (20 mL×2). The combined organic phases were washed with water (20 mL) and saturated brine (20 mL), dried over anhydrous sodium sulfate, filtered and concentrated in vacuo to give the crude product as a dark yellow oil. The crude product was purified by silica gel column chromatography (eluent: petroleum ether/ethyl acetate=20/1 to 10/1) to give product 43-1 as a white solid (180 mg, yield: 70.9%). MS (m/z): 484.3 (M+23).

The following compounds were prepared by similar method with Compound 43-1:

| Compound number | Structure | Spectrogram |
| --- | --- | --- |
| 44-1 | 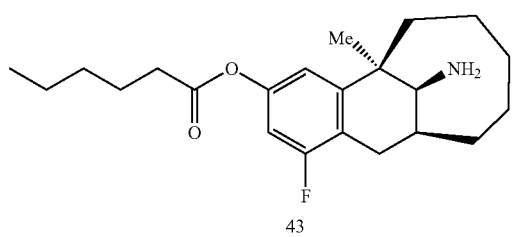 | MS (m/z): 512.1 (M + 23). |

| Compound number | Structure | Spectrogram |
|---|---|---|
| 45-1 | 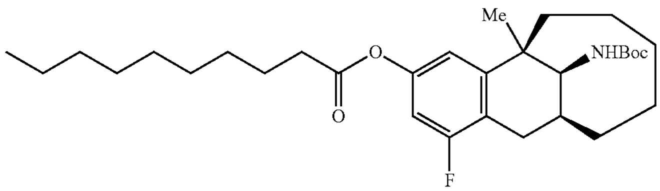 [SMILES: CCCCCCCCCC(=O)Oc1cc(F)c2c(c1)[C@@]1(C)CCCCC[C@@H](C2)[C@@H]1NC(=O)OC(C)(C)C] | MS (m/z): 540.5 (M + 23). |
| 46-1 | 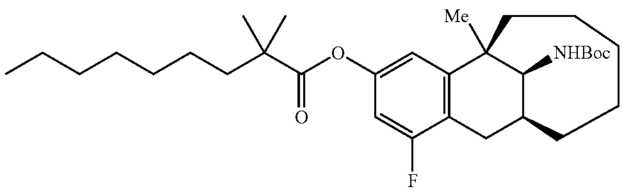 [SMILES: CCCCCCCC(C)(C)C(=O)Oc1cc(F)c2c(c1)[C@@]1(C)CCCCC[C@@H](C2)[C@@H]1NC(=O)OC(C)(C)C] | MS (m/z): 554.5 (M + 23). |
| 47-1 | 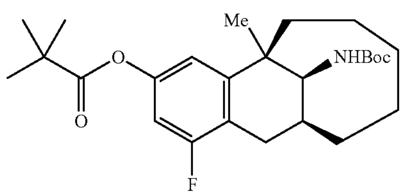 [SMILES: CC(C)(C)OC(=O)N[C@H]1[C@H]2CCCCC[C@]1(C)c1cc(OC(=O)C(C)(C)C)cc(F)c1C2] | MS (m/z): 470.4 (M + 23). |
| 48-1 | 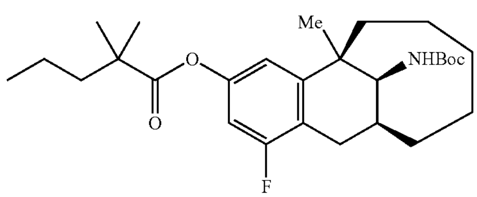 [SMILES: CCCC(C)(C)C(=O)Oc1cc(F)c2c(c1)[C@@]1(C)CCCCC[C@@H](C2)[C@@H]1NC(=O)OC(C)(C)C] | MS (m/z): 498.4 (M + 23). |
| 49-1 | 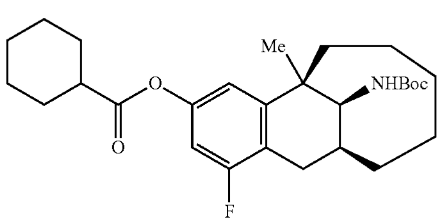 [SMILES: CC(C)(C)OC(=O)N[C@H]1[C@H]2CCCCC[C@]1(C)c1cc(OC(=O)C3CCCCC3)cc(F)c1C2] | MS (m/z): 496.2 (M + 23). |

Step 2: Preparation of Compound 43

Compound 43-1 (150 mg, 324 umol) was dissolved in dichloromethane (5 mL), then trifluoroacetic acid (500 uL) was added dropwise. After the addition was completed, stirring was continued at 15° C. for 2 hours. The reaction solution was diluted with 20 mL dichloromethane, then saturated aqueous $NaHCO_3$ was added to adjust the pH to approximately 7. The mixture was let stand to portion, and the organic phase was washed with water (10 mL) and saturated brine (10 mL), dried over anhydrous sodium sulfate, filtered and concentrated in vacuo to give the crude product as a pale yellow oil. The crude product was purified by high performance liquid phase preparative column (formic acid system) to obtain the formate salt of product 43 (58 mg, yield: 49.4%). MS (m/z): 362.1 (M+1). $^1$H NMR (400 MHz, $CD_3OD$) δ 8.54 (s, 1H), 6.92 (s, 1H), 6.81 (dd, $J_1$=2.0 Hz, $J_2$=10.0 Hz, 1H), 3.63 (d, J=5.2 Hz, 1H), 3.05-2.95 (m, 2H), 2.65-2.51 (m, 3H), 2.01-1.90 (m, 2H), 1.86-1.55 (m, 7H), 1.48 (s, 3H), 1.45-1.37 (m, 4H), 1.28-1.13 (m, 1H), 0.97 (t, J=7.2 Hz, 3H), 0.92-0.79 (m, 2H).

The following compounds were prepared by similar method with Compound 43:

| Compound number | Structure | Spectrogram |
|---|---|---|
| Compound 44 | 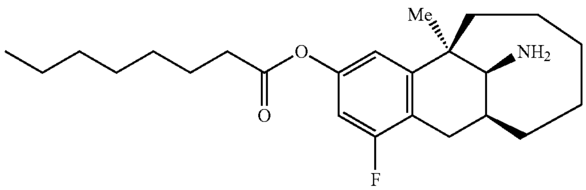 [SMILES: CCCCCCCC(=O)Oc1cc(F)c2c(c1)[C@@]1(C)CCCCC[C@@H](C2)[C@@H]1N] | MS (m/z): 390.2 (M + 1), $^1$H NMR (400 MHz, CD$_3$OD) δ 8.37 (br.s., 1H), 6.93 (s, 1H), 6.82 (dd, J$_1$ = 2.0 Hz, J$_2$ = 10.0 Hz, 1H), 3.68 (d, J = 5.2 Hz, 1H), 3.05-2.98 (m, 2H), 2.65-2.54 (m, 3H), 2.00-1.92 (m, 2H), 1.83-1.70 (m, 4H), 1.68-1.55 (m, 3H), 1.50 (s, 3H), 1.46-1.30 (m, 8H), 1.26-1.20 (m, 1H), 0.98-0.90 (m, 5H) |
| Compound 45 | 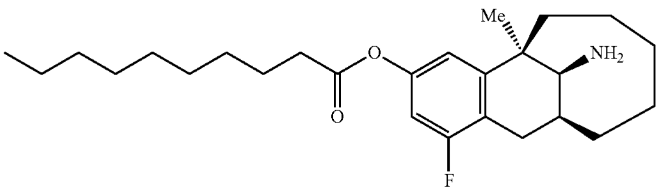 | MS (m/z): 459.2 (M + 42), $^1$H NMR (400 MHz, CDCl$_3$) δ 8.45 (s, 1H), 6.75-6.62 (m, 2H), 3.45 (d, J = 4.8 Hz, 1H), 2.95-2.81 (m, 2H), 2.62-2.41 (m, 3H), 1.90-1.76 (m, 3H), 1.73-1.62 (m, 3H), 1.60-1.46 (m, 3H), 1.40 (s, 3H), 1.38-1.15 (m, 12H), 1.14-0.97 (m, 1H), 0.89-0.66 (m, 5H) |
| Compound 46 | 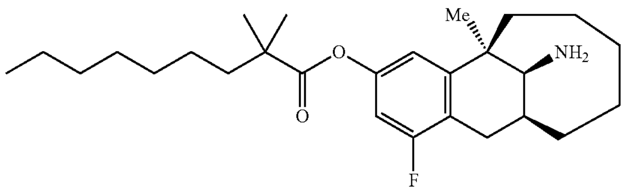 [SMILES: CCCCCCCC(C)(C)C(=O)Oc1cc(F)c2c(c1)[C@@]1(C)CCCCC[C@@H](C2)[C@@H]1N] | MS (m/z): 432.4 (M + 1), $^1$H NMR (400 MHz, CD$_3$OD) δ 8.51 (br. s., 1H), 6.85 (s, 1H), 6.77 (dd, J$_1$ = 2.0 Hz, J$_2$ = 10.0 Hz, 1H), 3.70 (d, J = 4.8 Hz, 1H), 3.11-2.93 (m, 2H), 2.58 (br. s., 1H), 2.07-1.91 (m, 2H), 1.85-1.58 (m, 7H), 1.50 (s, 3H), 1.43-1.29 (m, 18H), 1.28-1.13 (m, 1H), 0.99-0.78 (m, 5H). |
| Compound 47 | 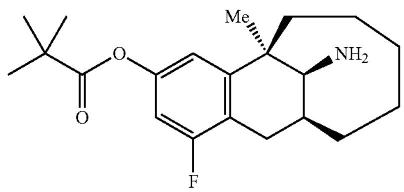 [SMILES: CC(C)(C)C(=O)Oc1cc(F)c2c(c1)[C@@]1(C)CCCCC[C@@H](C2)[C@@H]1N] | MS (m/z): 348.6 (M + 1), $^1$H NMR (400 MHz, CDCl$_3$) δ 8.45 (br. s., 1H), 6.74-6.61 (m, 2H), 3.51 (d, J = 4.8 Hz, 1H), 2.99-2.81 (m, 2H), 2.58 (br. s., 1H), 1.94-1.66 (m,4H), 1.65-1.50 (m,3H), 1.48 (s, 3H), 1.32 (s, 9H), 1.22-1.04 (m, 1H), 0.93-0.70 (m, 2H) |
| Compound 48 | 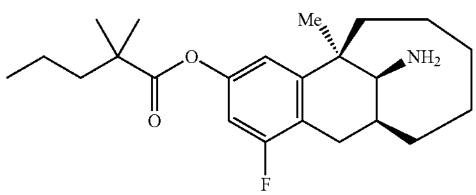 [SMILES: CCCC(C)(C)C(=O)Oc1cc(F)c2c(c1)[C@@]1(C)CCCCC[C@@H](C2)[C@@H]1N] | MS (m/z): 376.3 (M + 1), $^1$H NMR (400 MHz, CD$_3$OD) δ 6.85 (s, 1H), 6.79-6.72 (m, 1H), 3.63 (d, J = 4.8 Hz, 1H), 3.08-2.92 (m, 2H), 2.56 (br. s., 1H), 1.96-1.90 (m, 2H), 1.87-1.54 (m, 8H), 1.49 (s, 3H), 1.45-1.36 (m, 2H), 1.33 (s, 6H), 1.26-1.14 (m, 1H), 1.00 (t, J = 7.2 Hz, 3H), 0.95-0.77 (m, 2H). |
| Compound 49 | 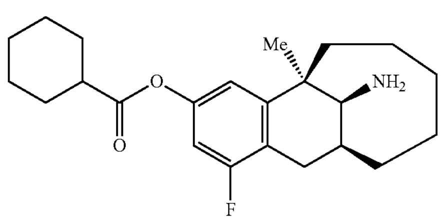 [SMILES: C[C@@]12CCCCC[C@@H](Cc3c(F)cc(OC(=O)C4CCCCC4)cc31)[C@@H]2N] | MS (m/z): 374.3 (M + 1), $^1$H NMR (400 MHz, CD$_3$OD) δ 8.55 (s, 1H), 6.91 (s, 1H), 6.80 (dd, J$_1$ = 1.6 Hz, J$_2$ = 10.0 Hz, 1H), 3.68 (d, J = 4.8 Hz, 1H), 3.10-2.92 (m, 2H), 2.69-2.51 (m, 2H), 2.07 (d, J = 12.4 Hz, 2H), 1.95-1.82 (m, 2H), 1.88-1.78 (m, 3H), 1.77-1.67 (m, 2H), 1.66-1.52 (m, 5H), 1.49 (s, 3H), 1.46-1.14 (m, 4H), 0.99-0.75 (m, 2H). |

Example 50: Preparation of Compound 50

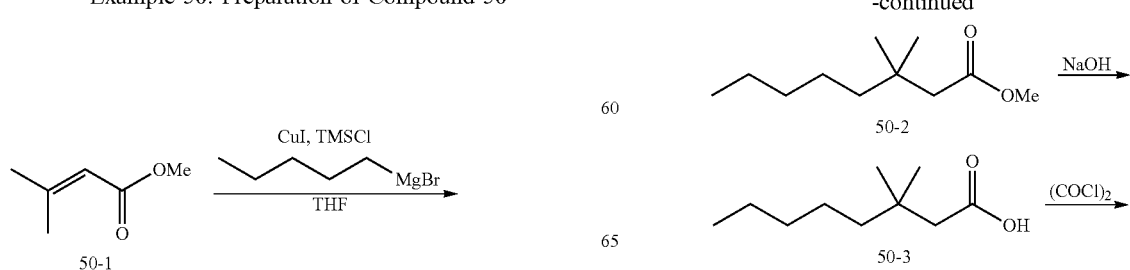

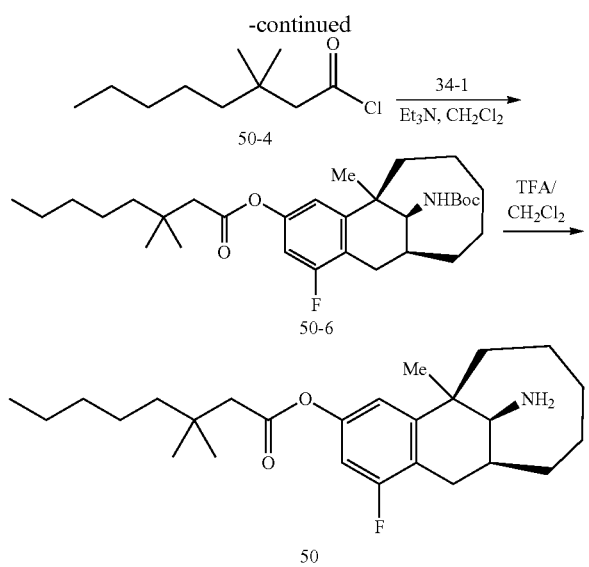

Step 1: Preparation of Compound 50-2

Compound 50-1 (2 g, 17 mmol) was dissolved in THF (25 mL), then TMSCl (2.28 g, 21 mmol) and CuI (333 mg, 1.75 mmol) were added under N$_2$. The solution was cooled to −15° C., added with n-pentylmagnesium bromide solution (20.4 mmol, 38.8 mL), then heated to 20° C. and stirred for 16 hours. The reaction was quenched by addition of saturated aqueous ammonium chloride (50 mL) and the aqueous phase was extracted with ethyl acetate (20 mL×3). The combined organic phases were washed with water (20 mL) and saturated brine (20 mL), dried over anhydrous sodium sulfate, filtered and concentrated in vacuo to give crude product 50-2 (3.30 g) as a yellow oil. The crude product was used directly in the next step without further purification. $^1$H NMR (400 MHz, CDCl$_3$) δ 3.64 (s, 3H), 2.17 (s, 2H) 1.35-1.24 (m, 8H), 0.98 (s, 6H), 0.88 (t, J=7.2 Hz, 3H).

Step 2: Preparation of Compound 50-3

Compound 50-2 (3.3 g, 17.71 mmol) was dissolved in methanol (10 mL), then a solution of potassium hydroxide (1 g, 17.82 mmol) in water (2 mL) was added. After stirring at 20° C. for 16 hours, dilute hydrochloric acid solution (2M, 10 mL) was added to adjust the pH to approximately 4, followed by addition of ethyl acetate (50 mL), then the mixture was let stand to portion. The organic phase was washed twice with saturated brine (20 mL), dried over anhydrous sodium sulfate, filtered and concentrated in vacuo to give the crude product 50-3 (2.5 g) as a pale yellow oil. The crude product was used directly in the next step without further purification. $^1$H NMR (400 MHz, CDCl$_3$) δ 2.23 (s, 2H), 1.34-1.24 (m, 8H), 1.02 (s, 6H), 0.89 (t, J=7.2 Hz, 3H).

Step 3: Preparation of Compound 50-4

Compound 50-3 (150 mg, 870.78 umol) was dissolved in dichloromethane (10 mL), then oxalyl chloride (221 mg, 1.74 mmol) and DMF (6 mg, 87 umol) were successively added. After being stirred at 20° C. for 0.5 h, the reaction solution was concentrated in vacuo to give crude product 50-4 (170.00 mg) as a white solid. The crude product was used directly in the next step without further purification.

Step 4: Preparation of Compound 50-5

Compound 34-1 (220 mg, 605.28 umol) was dissolved in dichloromethane (5 mL), followed by successive addition of 50-4 (115 mg, 605.28 umol) and triethylamine (122 mg, 1.21 mmol). After being stirred at 20° C. for 1 hour, the reaction solution was directly concentrated under vacuum to give the crude product as a dark yellow oil. The crude product was purified by silica gel preparative plate (developing solvent: petroleum ether/ethyl acetate=20/1) to give product 50-5 as a white solid (210 mg, yield: 67.0%). MS (m/z): 540.4 (M+1).

Step 5: Preparation of Compound 50

Compound 50-5 (210 mg, 405 umol) was dissolved in dichloromethane (5 mL), then trifluoroacetic acid (500 uL) was added. After being stirred at 20° C. for 16 hours, the reaction solution was diluted with 20 mL methylene chloride, then saturated aqueous NaHCO$_3$ solution was added to adjust the pH to approximately 7 and the mixture was let stand to portion. The organic phase was washed with water (10 mL) and saturated brine (10 mL), dried over anhydrous sodium sulfate, filtered, and concentrated in vacuo to give the crude product as pale yellow oil. The crude product was purified by high performance liquid phase preparative column (formic acid system) to obtain the formate salt of compound 50 (85.00 mg, yield: 50.2%). MS (m/z): 418.4 (M+1). $^1$H NMR (400 MHz, CD$_3$OD) δ 8.55 (br. s., 1H), 6.88 (s, 1H), 6.79 (dd, J=2.0, 10.0 Hz, 1H), 3.64 (d, J=4.4 Hz, 1H), 3.08-2.93 (m, 2H), 2.56 (br. s., 1H), 2.48 (s, 2H), 2.03-1.89 (m, 2H), 1.87-1.54 (m, 5H), 1.49 (s, 3H), 1.44-1.16 (m, 9H), 1.11 (s, 6H), 0.93 (t, J=7.2 Hz, 3H), 0.89-0.77 (m, 2H).

Example 51: Preparation of Compound 51

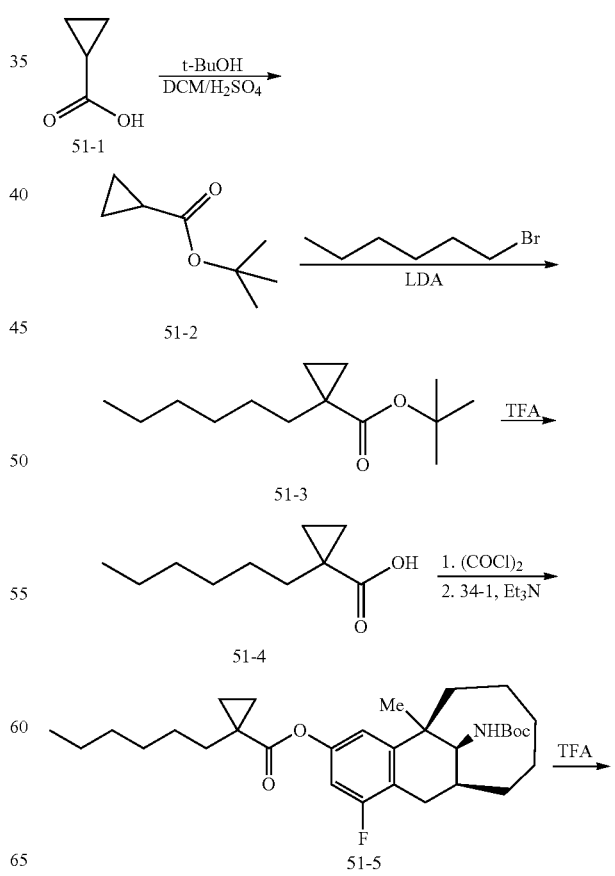

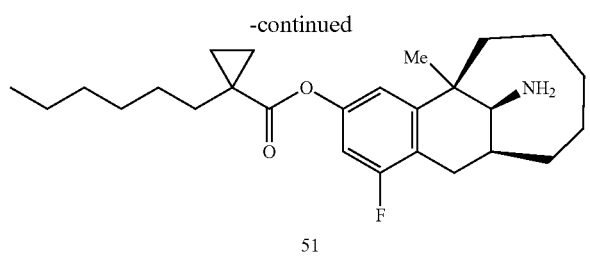

51

Step 1: Preparation of Compound 51-2

Magnesium sulfate (27.96 g, 232.32 mmol) was added to dichloromethane (100 mL), then concentrated sulfuric acid (5.70 g, 58.08 mmol) was added. After vigorous stirring for 15 minutes, cyclopropanecarboxylic acid (5.00 g, 58.08 mmol) and tert-butanol (21.52 g, 290.39 mmol) were added. After stirring at 25° C. for 12 hours, saturated sodium carbonate solution was added until magnesium sulfate was dissolved. Dichloromethane (50 mL) was added and the mixture was let stand to portion. The organic phase was washed with saturated brine (50 mL×3), dried over anhydrous sodium sulfate, filtered and concentrated in vacuo to give 51-2 as a light yellow oily liquid (4.20 g, yield: 50.9%). $^1$HNMR (400 MHz, CDCl$_3$) δ 1.56-1.47 (m, 1H), 1.45 (s, 9H), 0.93-0.89 (m, 3H), 0.80-0.72 (m, 2H).

Step 2: Preparation of Compound 51-3

Compound 51-2 (3.70 g, 26.02 mmol) was dissolved in tetrahydrofuran (5 mL). After the solution was cooled to −78° C., diisopropylaminolithium in tetrahydrofuran and n-heptane (2M, 15.61 mL) was slowly added. After stirring for 0.5 hour at this temperature, 1-bromohexane (5.15 g, 31.22 mmol) was slowly added. After the addition was completed, the temperature was slowly raised to 25° C. and the reaction solution was stirred at this temperature for 12 hours. The reaction was quenched by addition of 10 mL water and the aqueous phase was extracted with 10 mL dichloromethane. The organic phase was washed with saturated brine (10 mL×3), dried over anhydrous sodium sulfate, filtered, and concentrated in vacuo to give 51-3 (4.20 g) as a brown oily liquid. The crude product was directly used in the next step without further purification.

Step 3: Preparation of Compound 51-4

Compound 51-3 (4.2 g, 18.5 mmol) was dissolved in dichloromethane (10 mL), then trifluoroacetic acid (2.54 g, 22.27 mmol) was added. After stirring at 25° C. for 3 hours, 10 ml water and 10 ml dichloromethane were added. The mixture was let stand to portion, and the organic phase was further mixed with 10 mL saturated sodium carbonate solution and stirred. The aqueous phase was back-extracted with 10 ml dichloromethane, acidified with 5 ml of concentrated hydrochloric acid, and the aqueous phase was extracted with 10 ml dichloromethane. The organic phase was washed with saturated brine (10 mL×3), dried over anhydrous sodium sulfate, filtered and concentrated in vacuo to give 51-4 as a yellow oily liquid (800 mg, yield: 25.3%).

$^1$H NMR (400 MHz, CDCl$_3$) δ 1.54-1.41 (m, 4H), 1.36-1.22 (m, 8H), 0.88 (t, J=6.8 Hz, 3H), 0.75 (q, J=3.6 Hz, 2H).

Step 4: Preparation of Compound 51-5

Compound 51-4 (140.52 mg, 825.38 umol) was dissolved in dichloromethane (2 ml), then a drop of DMF and oxalyl chloride (125.72 mg, 990.45 umol) were added. After being stirred at 25° C. for 0.5 hours, the reaction solution was directly concentrated under vacuum. The residue was dissolved in dichloromethane (2 mL) and added to a solution of 34-1 (200.00 mg, 550.25 umol) in dichloromethane (2 mL).

After being stirred at 25° C. for 12 hours, the reaction solution was quenched by addition of dichloromethane (5 mL) and water (5 mL). The mixture was let stand to portion, and the organic phase was washed with saturated brine (10 mL×3), dried over anhydrous sodium sulfate, filtered, and concentrated in vacuo to give the crude product 51-5 (400 mg) as a yellow oil. MS m/z: 460.3 (M-56+1).

Step 5: Preparation of Compound 51

Compound 51-5 (350 mg, 678.69 umol) was dissolved in dichloromethane (3 ml), then trifluoroacetic acid (462 mg, 4.05 mmol) was added. After reacting at 25° C. for 2 hours, a saturated aqueous sodium bicarbonate solution was added to adjust the pH to approximately 7. The organic phase was washed with saturated brine (5 ml×3), dried over anhydrous sodium sulfate, filtered, and concentrated in vacuo to give the crude product. The crude product was purified by high performance liquid phase preparative column (formic acid system) to obtain the formate salt of compound 51 (120 mg, yield: 37.2%). MS (m/z): 416.3 (M+1). $^1$H NMR (400 MHz, CD$_3$OD) δ 8.55 (s, 1H), 6.88 (s, 1H), 6.80-6.74 (m, 1H), 3.66 (d, J=5.2 Hz, 1H), 3.13-2.87 (m, 2H), 2.71-2.45 (m, 1H), 2.09-1.87 (m, 2H), 1.85-1.53 (m, 9H), 1.49 (s, 3H), 1.42-1.29 (m, 8H), 1.27-1.07 (m, 1H), 0.98-0.76 (m, 7H).

Example 52: Preparation of Compound 52

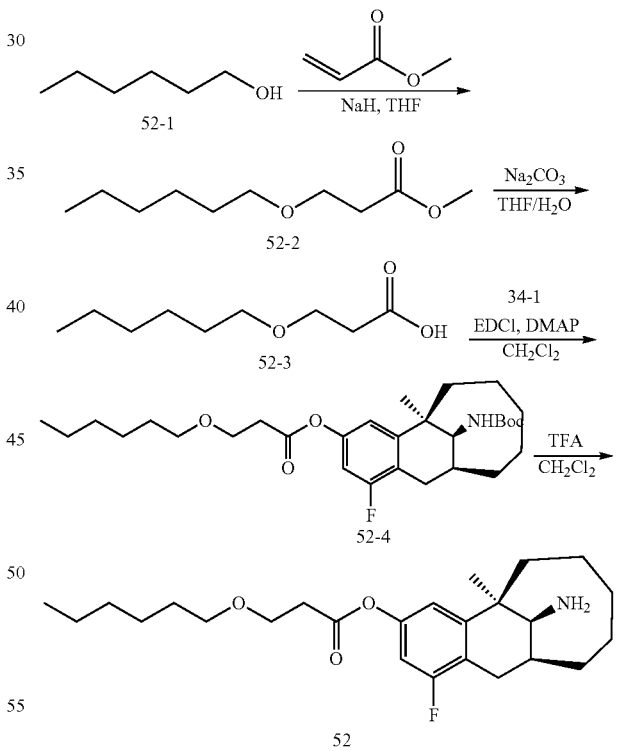

Step 1: Preparation of Compound 52-2

Compound 52-1 (5.0 g, 48.93 mmol) was dissolved in THF (30 mL). Sodium hydride (196 mg, 4.89 mmol, 60% purity) and methyl acrylate (6.30 g, 73.18 mmol) were successively added at 0° C. The solution was slowly heated to reflux, and stirred for 16 hours. After being cooled down, the reaction solution was poured into 40 mL water to be quenched, and the aqueous phase was extracted with ethyl acetate (30 mL×3). The combined organic phases were washed with 20 mL water and 20 mL saturated brine, dried over anhydrous sodium sulfate, filtered and concentrated in vacuo to give the crude product. The crude product was purified by silica gel column chromatography (eluent: petroleum ether/ethyl acetate=50/1 to 30/1) to give the crude product 52-2 (2.20 g) as a colorless liquid. $^1$H NMR (400 MHz, CDCl$_3$) δ 3.71-3.67 (m, 5H), 3.43 (t, J=6.8 Hz, 2H), 2.59 (t, J=6.4 Hz, 2H), 1.72-1.19 (m, 8H), 0.95-0.83 (m, 3H).

Step 2: Preparation of Compound 52-3

Compound 52-2 (1.00 g, 5.31 mmol) was dissolved in a mixed solution of THF (30 mL) and H$_2$O (30 mL), then Na$_2$CO$_3$ (2.25 g, 21.25 mmol) was added. After being heated to 50° C., the reaction solution was stirred for 3 hours. The reaction solution was poured into 2N aqueous NaOH solution (20 mL) to be quenched. The aqueous phase was washed with dichloromethane (40 mL), adjusted to pH 2 with 6N HCl, then extracted with dichloromethane (30 mL×3). The combined organic phases were washed with 10 mL saturated brine, dried over anhydrous sodium sulfate, filtered, and concentrated in vacuo to give 52-3 as a light yellow liquid (240 mg, yield: 25.9%). $^1$H NMR (400 MHz, CDCl$_3$) δ 3.70 (t, J=6.4 Hz, 2H), 3.46 (t, J=6.8 Hz, 2H), 2.63 (t, J=6.4 Hz, 2H), 1.63-1.51 (m, 2H), 1.38-1.22 (m, 6H), 0.88 (t, J=6.8 Hz, 3H).

Step 3: Preparation of Compound 52-4

Compound 52-3 (300 mg, 1.72 mmol) was dissolved in dichloromethane (15 mL), then 4-dimethylaminopyridine (210 mg, 1.72 mmol), 34-1 (750 mg, 2.06 mmol) and 1-(3-dimethyl aminopropyl)-3-ethylcarbodiimide hydrochloride (320 mg, 2.06 mmol) were successively added. After being stirred at 15° C. for 2 hours, the reaction was poured into 40 mL water to be quenched and the aqueous phase was extracted with dichloromethane (15 mL×3). The combined organic phases were washed with saturated brine (15 mL), dried over anhydrous sodium sulfate, filtered, and concentrated in vacuo to give the crude product. The crude product was purified by silica gel column chromatography (eluent: petroleum ether/ethyl acetate=15/1 to 5/1) to give 52-4 (775 mg, yield: 86.0%) as a colorless viscous solid. MS m/z: 420.4 (M-100+1). $^1$H NMR (400 MHz, CDCl$_3$) δ 6.75-6.68 (m, 2H), 4.92 (d, J=10.4 Hz, 1H), 4.22-3.98 (m, 1H), 3.80 (t, J=6.4 Hz, 2H), 3.49 (t, J=6.8 Hz, 2H), 2.90-2.85 (m, 2H), 2.81 (t, J=6.4 Hz, 2H), 2.40 (br. s., 1H), 1.84-1.53 (m, 10H), 1.49 (s, 9H), 1.40-1.24 (m, 9H), 1.10-0.80 (m, 5H).

Step 4: Preparation of Compound 52

Compound 52-4 (700 mg, 1.35 mmol) was dissolved in dichloromethane (10 mL), then trifluoroacetic acid (2.0 mL) was added. After being stirred at 15° C. for 3 hours, the reaction solution was poured into 60 mL ethyl acetate to be diluted, then saturated aqueous sodium bicarbonate solution was slowly added to adjust the pH to approximately 7, and the aqueous phase was extracted with ethyl acetate (30 mL×3). The combined organic phases were washed with 20 mL water and 20 mL saturated brine, dried over anhydrous sodium sulfate, filtered, and concentrated in vacuo to give the crude product. The crude product was purified by high performance liquid preparative column to obtain the hydrochloride salt of compound 52 (250 mg, yield: 44.1%). MS m/z: 420.6 (M+1). $^1$H NMR (400 MHz, CDCl$_3$) δ 8.91 (br. s., 2H), 6.84-6.66 (m, 2H), 3.79 (t, J=6.4 Hz, 2H), 3.75-3.61 (m, 1H), 3.48 (t, J=6.8 Hz, 2H), 3.00-2.85 (m, 2H), 2.81 (t, J=6.4 Hz, 2H), 2.29-2.00 (m, 2H), 1.98-1.81 (m, 2H), 1.71-1.50 (m, 9H), 1.44-1.19 (m, 6H), 0.96-0.70 (m, 5H).

In Vitro Activity Test

Experiment Objective:

Fluorescence imaging plate reader FLIPR was used to detect changes of intracellular calcium signals. EC50 and IC50 values of the compounds were used as indicators to evaluate the activation or inhibition of the compounds on μ, κ, and δ opioid receptors.

Experimental Materials:

Cell lines: HEK293-μ, HEK293-κ and HEK293-δ, stable-transfected cell lines HEK293-μ, HEK293-κ and HEK293-δ; Cell culture media (DMEM, Invitrogen #11965118, 10% fetal bovine serum Invitrogen #10099141, Geneticin Selective Antibiotic (G418) 300 μg/mL, Invitrogen #10131027, Blasticidin-S HCL 2 ug/mL Invitrogen #A1113902)

Pancreatic enzyme (Invitrogen, #25200-072)

DPBS (Hyclone, #SH30028.01B)

Fluo-4 Direct (Invitrogen# F10471)

HBSS (Invitrogen #14025126)

HEPES (Invitrogen #15630130)

384 Cell plate (Greiner #781946)

384 Compound plate (Greiner #781280)

CO$_2$ incubator (Thermo#371)

Centrifuge (Eppendorf #5810R)

Vi-cell Cell Counter (Beckman Coulter)

POD 810 Plate Assembler Automatic Microplate Pretreatment System

Labcyte FLIPR, Molecular Device

Experimental Procedures and Methods:

1. Cell Seeding (HEK293-μ, HEK293-κ and HEK293-δ Cells)

1) Preheating medium, pancreatic enzyme, and DPBS in a 37° C. water bath. Aspirating the culture medium from the cell culture flask and washing it with 10 mL DPBS;

2) Adding the preheated pancreatic enzyme solution to the cell culture flask, rotating the flask slightly to make the pancreatic enzymes evenly cover the cell surface of the flask, and then putting it into a 37° C., 5% CO$_2$ incubator to digest for 1-2 minutes;

3) Suspending the cells with 10-15 mL culture medium in each T150 cm$^2$ cell culture flask, centrifugating at 800 rpm for 5 minutes, and resuspending the cells with 10 mL culture medium, aspirating 1 mL cell resuspension to be counted with Vi-cell;

4) Diluting HEK293-μ, HEK293-κ and HEK293-δ cells to 5×10$^5$/mL with culture medium, use multichannel pipette to add diluted cells into 384 plate (Greiner #781946) (50 μL/well, 25000 cells/well for HEK293-μ, HEK293-κ and HEK293-δ cells). Placing the cell plate in a 37° C., 5% CO$_2$ incubator overnight.

2. Adding Compound Samples:

1) Diluting the compound to 20 mM with DMSO, 3 fold diluted, 8 gradients, double reduplicative wells, and adding it to the compound plate using an Echo ultrasonic liquid handler device (Echo liquid handler).

3. FLIPR Experiment:

1) Washing off the cell culture medium in 384 plate with vacuum pump, adding 20 μL Fluo-4 Direct fluorescent dye, then incubating in a 37° C., 5% CO$_2$ incubator for 50 minutes, followed by equilibrating at room temperature for 10 minutes.

2) EC50 test: Adding 20 uL HBSS buffer (containing 20 mM HEPES) to the compound plate, mixing well and centrifugating. Placing the cell plate and compound plate into FLIPR and reading the fluorescence value.

3) After the EC50 test, placing the cell plate into a 37° C., 5% CO$_2$ incubator to be incubated for 25 minutes. Calculating the EC80 value with the EC50 value of the positive agonist, preparing 4× EC80 solution, adding it to the 384 compound plate by multichannel pipette, and mixing well and centrifugating.

4) IC50 test: In FLIPR, successively placing 4× EC80 plate, cell plate, FLIPR tip, running the program and reading the fluorescence value.

4. Data Analyzing: Using Prism 5.0 to Analyze the Data and Calculate the EC50 and IC50 Values of the Compounds.

TABLE 1

In vitro activity test results

| Test sample | Mu receptor $EC_{50}$ (uM) | Mu receptor $IC_{50}$ (uM) | Kapp receptor $EC_{50}$ (uM) | Kapp receptor $IC_{50}$ (uM) | Delt receptor $EC_{50}$ (uM) | Delt receptor $IC_{50}$ (uM) |
|---|---|---|---|---|---|---|
| Compound 1 | E | A | E | B | E | C |
| Compound 2 | A | B | E | C | E | E |
| Compound 3 | B | B | E | B | E | C |
| Compound 4 | B | B | E | C | E | E |
| Compound 5 | C | D | C | D | E | E |
| Compound 6 | A | B | E | C | E | C |
| Compound 7 | E | C | E | C | E | E |
| Compound 8 | B | C | E | C | E | E |
| Compound 9 | E | C | E | C | E | E |
| Compound 10 | E | D | E | D | E | E |
| Compound 11 | E | E | D | E | E | E |
| Compound 12 | D | D | E | E | E | E |
| Compound 13 | D | D | D | D | E | E |
| Compound 14 | D | D | E | D | E | E |
| Compound 15 | E | E | D | E | E | E |
| Hydrochloride of Compound 16 | D | C | E | C | E | E |
| Hydrochloride of Compound 17 | C | C | E | D | E | E |
| Compound 18 | E | C | E | E | E | E |
| Compound 19 | E | E | E | E | E | E |
| Compound 20 | E | D | E | D | E | E |
| Compound 21 | A | A | E | C | E | C |
| Compound 22 | C | B | E | C | E | D |
| Compound 23 | A | A | E | C | E | E |
| Compound 24 | D | B | E | C | E | C |
| Compound 25 | B | C | E | C | E | C |
| Compound 26 | E | D | E | E | E | E |
| Compound 27 | E | C | E | D | E | E |
| Compound 28 | A | B | E | B | E | C |
| Compound 29 | A | B | E | C | E | D |
| Compound 30 | B | B | E | B | E | D |
| Compound 31 | D | D | E | D | E | E |
| Compound 32 | B | B | B | B | E | C |
| Compound 33 | B | C | B | B | C | C |

Note:
A ≤ 0.1 uM;
0.1 uM < B ≤ 1 uM;
1 uM < C ≤ 10 uM;
10 uM < D ≤ 100 uM;
E > 100 uM.

In vitro activity tests demonstrated: the compounds of the present disclosure have agonistic and antagonistic dual effect on the Mu receptor, and weaker antagonistic effect on the Kapp receptor.

Drug Metabolism Experiment

Experiment Objective:

Through the in vivo drug metabolism test in rats, values such as $C_{max}$, $t_{1/2}$, AUC, MRT and B/P ratio of the compound in vivo were used as indicators to evaluate the metabolism of the compound in rats.

1. Pharmacokinetic Study of Intravenous Injection of Dezocine and Analogues Thereof in Rats Mixing the test compound with an appropriate amount of physiological saline solution of 20% polyethylene glycol 400, followed by vortex and sonicate, and adjusting the pH to 4-5 with hydrochloric acid to obtain 5 mg/mL approximately clear solution, filtering the solution by microporous filtering film to be used. Selecting 6 to 9 weeks old SD rats (Shanghai Sleek Laboratory Animal Co., Ltd.) and intravenously injecting the test compound solution at a dose of 1 mg/kg. Collecting whole blood in certain time to prepare and obtain plasma. Analyzing drug concentrations by LC-MS/MS method and calculating pharmacokinetic parameters using Phoenix WinNonlin software (Pharsight, USA).

2. Brain Distribution Study of Intravenous Injection of Dezocine and Analogues Thereof in Rats Intravenously injecting the test compound solution in the same manner as example 1 at a dose of 1 mg/kg. Executing animals with carbon dioxide 15 minutes and 2 hours after dosing, collecting whole blood and brain tissue sample, centrifugating the whole blood to obtain plasma, and homogenizing the brain tissue with triple volumes of deionized water. Analyzing drug concentration of the plasma and brain homogenate samples by LC-MS/MS method, and calculating the concentration ratio of brain tissue to plasma (B/P ratio).

3. Pharmacokinetics of Intramuscular Injection of Compound 21 and Prodrug Thereof in Rats Mixing the test compound with an appropriate amount of sesame oil, followed by vortex and sonicate, to prepare and obtain 25 μmol/mL homogeneous suspension. Selecting 6 to 9 weeks old SD rats (Shanghai Sleek Laboratory Animal Co., Ltd.), intramuscularly injecting the suspension of the test compound at a dose of 20 μmol/kg or 40 μmol/kg. Collecting whole blood in certain time, adding precipitant (acetonitrile, methanol and analytical internal standard) and centrifugating. Analyzing drug concentration (if the test drug is a prodrug, drug concentrations of the prodrug and hydrolyzed parent drug are simultaneously analyzed) of the supernatant solution by LC-MS/MS method, and calculating pharmacokinetic parameters using Phoenix WinNonlin software (Pharsight, USA).

TABLE 2

Results of intravenous pharmacokinetics test of dezocine and analogues thereof

| Compound number | Dezocine | Compound 21 | Compound 23 |
|---|---|---|---|
| $C_0$ (nM) | 684 | 493 | 362 |
| $T_{1/2}$ (hr) | 1.26 | 1.42 | 1.60 |
| $Vd_{ss}$ (L/kg) | 12.2 | 16.2 | 20.6 |
| Cl (mL/min/kg) | 139 | 155 | 165 |
| $AUC_{0-last}$ (nM · hr) | 485 | 387 | 341 |
| $MRT_0$-last (hr) | 1.22 | 1.35 | 1.65 |
| B/P ratio (0.25 h/2 h) | 9.29/12.9 | 13.3/19.8 | 16.7/27.9 |

Note:
All compounds were administered at dose of 1 mg/kg.

Intravenous injection pharmacokinetic data indicates that: the compounds of the present disclosure have a higher B/P ratio than dezocine and are easier to penetrate the blood-brain barrier.

TABLE 3

Results of intramuscular injection pharmacokinetic test of Compound 21

| Compound number | Compound 21 |
|---|---|
| $C_{max}$ (nM) | 1753 |
| $T_{max}$ (hr) | 0.50 |

TABLE 3-continued

Results of intramuscular injection pharmacokinetic test of Compound 21

| Compound number | Compound 21 |
|---|---|
| $t_{1/2}$ (hr) | 4.20 |
| $AUC_{0\text{-}last}$ (nM · hr) | 3989 |
| $MRT_0$-last (hr) | 2.82 |

Note:
the dose was 40 μmol/kg.

TABLE 4

Results of intramuscular injection of Compound 21 carboxylic diester prodrug

| | Compound number | | | | | |
|---|---|---|---|---|---|---|
| | Compound 34 | | Compound 35 | | Compound 38 | |
| | Compound 34 | Parent compound 21 | Compound 25 | Parent compound 21 | Compound 38 | Parent compound 21 |
| $C_{max}$ (nM) | 3.91 | 399 | ND | 222 | ND | 192 |
| $T_{max}$ (hr) | 0.25 | 2.33 | ND | 4.33 | ND | 2.17 |
| $t_{1/2}$ (hr) | ND | 7.2 | ND | 5.51 | ND | 33.7 |
| $AUC_{0\text{-}last}$ (nM · hr) | 2.95 | 3699 | ND | 2660 | ND | 3235 |
| $MRT_0$-last (hr) | 0.539 | 8.12 | ND | 9.15 | ND | 18.0 |

Note:
All compounds were administered at dose of 20 μmol/kg. Every 20 μmol carboxylic diester prodrug theoretically hydrolyzes 40 μmol active ingredient of compound 21.
ND = cannot be determined (parameters cannot be determined because the end-elimination phase cannot be fully defined).

TABLE 5

Results of intramuscular injection of Compound 21 carboxylic monoester prodrug

| | Compound number | | | | | |
|---|---|---|---|---|---|---|
| | Compound 43 | | Compound 44 | | Compound 45 | |
| | Compound 43 | Parent compound 21 | Compound 44 | Parent compound 21 | Compound 45 | Parent compound 21 |
| $C_{max}$ (nM) | ND | 322 | ND | 130 | ND | 48.3 |
| $T_{max}$ (hr) | ND | 2.67 | ND | 3.33 | ND | 10.0 |
| $t_{1/2}$ (hr) | ND | 4.07 | ND | 11.9 | ND | 39.8 |
| $AUC_{0\text{-}last}$ (nM · hr) | ND | 2286 | ND | 1692 | ND | 1547 |
| $MRT_0$-last (hr) | ND | 5.89 | ND | 13.0 | ND | 21.9 |

Note:
All compounds were administered at dose of 40 μmol/kg. Every 40 μmol carboxylic acid monoester prodrug theoretically hydrolyzes 40 μmol active ingredient of compound 21.
ND = cannot be determined (parameters cannot be determined because the end-elimination phase cannot be fully defined).

The results of intramuscular injection pharmacokinetic test showed that: after the sesame oil suspensions of carboxylic diester prodrug and carboxylic monoester prodrug of Compound 21 were administered by intramuscular injection, both of them can be slowly released in vivo, followed by being quickly hydrolyzed to the parent drug compound 21, which can significantly prolong the retention time of the parent drug compound 21 in rats, and reduce the $C_{max}$ so as to achieve the purpose of prolonging the drug action time and improving the safety.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are to be regarded as a departure from the disclosure, and all such modifications are intended to be included within the scope of the disclosure.

What is claimed is:

1. A compound represented by formula (I), (II) or (III), or a pharmaceutically acceptable salt or tautomer thereof,

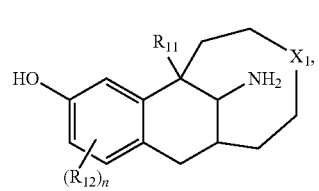
(I)

-continued

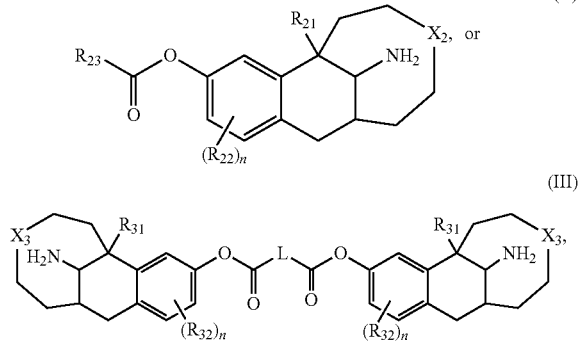
(II)

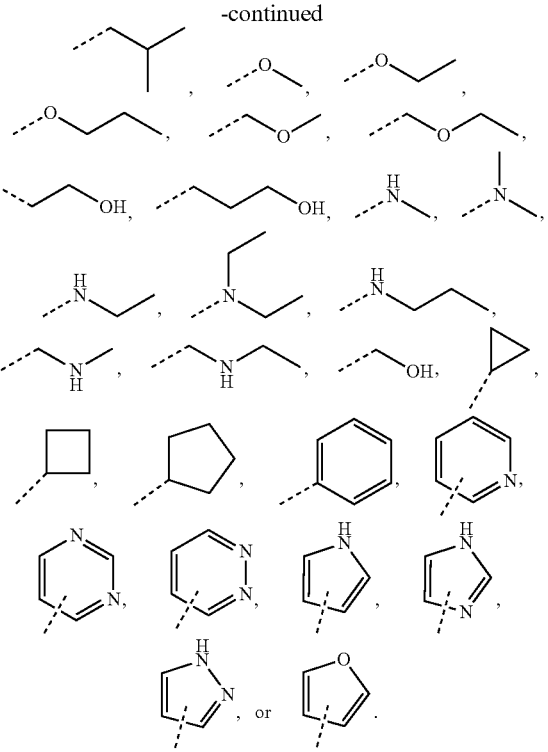

wherein,
each of $X_1$, $X_2$, $X_3$ is independently single bond, $CH_2$, $C(RR)$, $NH$, $N(R)$, $O$, or $S$;
$R_{12}$ is F, Cl, Br, I, CN, OH, or $NH_2$, or $R_{12}$ is selected from the group consisting of $C_{1-6}$ alkyl or heteroalkyl, 3-7 membered cycloalkyl or heterocycloalkyl, and 5-7 membered aryl or heteroaryl, each of which is optionally substituted by 1, 2, or 3 R;
each of $R_{22}$ and $R_{32}$ is independently F, Cl, Br, I, CN, OH, or $NH_2$, or each of $R_{22}$ and $R_{32}$ is independently selected from the group consisting of $C_{1-6}$ alkyl or heteroalkyl, 3-7 membered cycloalkyl or heterocycloalkyl, and 5-7 membered aryl or heteroaryl, each of which is optionally substituted by 1, 2, or 3 R;
n is 1, 2, or 3;
each of $R_{11}$, $R_{21}$ and $R_{31}$ is independently selected from the group consisting of $C_{1-6}$ alkyl and $C_{1-6}$ heteroalkyl, each of which is optionally substituted by 1, 2, or 3 R;
$R_{23}$ is selected from the group consisting of $C_{1-12}$ alkyl, $C_{1-12}$ heteroalkyl, $C_{3-7}$ cycloalkyl, and 3-7 membered heterocycloalkyl, each of which is optionally substituted by 1, 2, or 3 R;
L is selected from the group consisting of $C_{1-12}$ alkyl, $C_{1-12}$ heteroalkyl, $C_{3-7}$ cycloalkyl, and 3-7 membered heterocycloalkyl, each of which is optionally substituted by 1, 2, or 3 R;
said "hetero" represents O, S, or N, the number of which is 1, 2 or 3 in any of the above cases;
said R is F, Cl, Br, I, CN, OH, $NH_2$, $C_{1-3}$ alkyl, or $C_{1-3}$ heteroalkyl;
said $C_{1-3}$ alkyl or $C_{1-3}$ heteroalkyl is optionally substituted by 1, 2, or 3 substituents selected from the group consisting of F, Cl, Br, I, CN, OH, and $NH_2$;
two geminal or ortho R optionally connect to the same atom forming 3-6 membered cycloalkyl or heterocycloalkyl.

2. The compound, the pharmaceutically acceptable salt or tautomer thereof according to claim 1, wherein $R_{12}$ is F, Cl, Br, I, CN, OH, or $NH_2$, or $R_{12}$ is selected from the group consisting of $C_{1-5}$ alkyl or heteroalkyl, 3-5 membered cycloalkyl or heterocycloalkyl, and 5-6 membered aryl or heteroaryl, each of which is optionally substituted by 1, 2, or 3 R.

3. The compound, the pharmaceutically acceptable salt or tautomer thereof according to claim 2, wherein $R_{12}$ is F, Cl, Br, I, CN, OH, $NH_2$, Me,

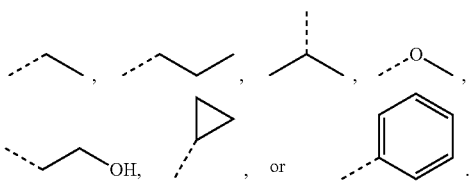

-continued

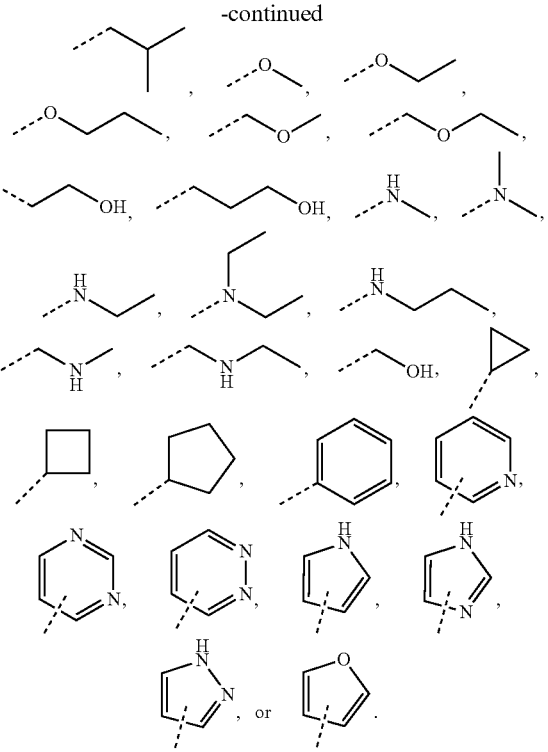

4. The compound, the pharmaceutically acceptable salt or tautomer thereof according to claim 2, wherein $R_{12}$ is F, Cl, Br, I, CN, OH, $NH_2$, Me,

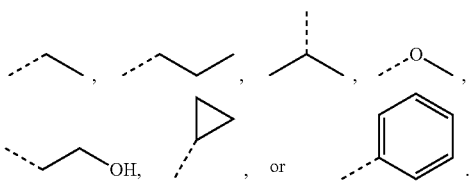

5. The compound, the pharmaceutically acceptable salt or tautomer thereof according to claim 1, wherein each of $R_{22}$ and $R_{32}$ is independently F, Cl, Br, I, CN, OH, or $NH_2$, or each of $R_{22}$ and $R_{32}$ is independently selected from the group consisting of $C_{1-5}$ alkyl or heteroalkyl, 3-5 membered cycloalkyl or heterocycloalkyl, and 5-6 membered aryl or heteroaryl, each of which is optionally substituted by 1, 2, or 3 R.

6. The compound, the pharmaceutically acceptable salt or tautomer thereof according to claim 5, wherein each of $R_{22}$ and $R_{32}$ is independently F, Cl, Br, I, CN, OH, $NH_2$, Me,

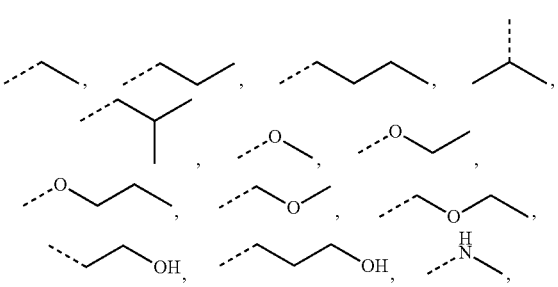

-continued

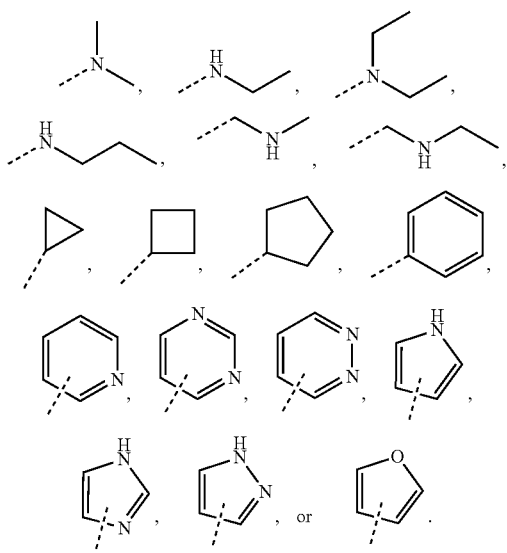

7. The compound, the pharmaceutically acceptable salt or tautomer thereof according to claim 6, wherein each of $R_{22}$ and $R_{32}$ is independently F, Cl, Br, I, CN, OH, $NH_2$, Me,

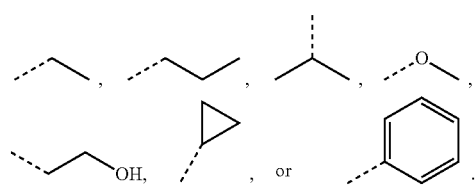

8. The compound, the pharmaceutically acceptable salt or tautomer thereof according to claim 1, wherein each of $R_{11}$, $R_{21}$ and $R_{31}$ is independently Me,

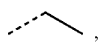

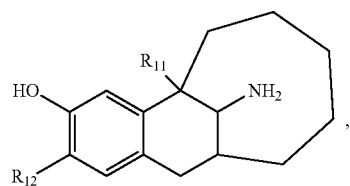

I-1

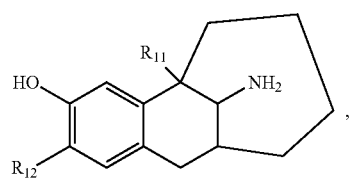

I-3 trifluoromethyl, monofluoromethyl,

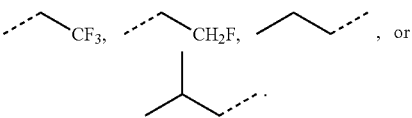, or

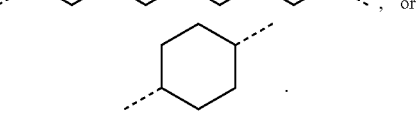

9. The compound, the pharmaceutically acceptable salt or tautomer thereof according to claim 1, wherein L is $(CH_2)_4$, $(CH_2)_5$, $(CH_2)_6$, $(CH_2)_7$, $(CH_2)_8$, $(CH_2)_9$, $(CH_2)_{10}$,

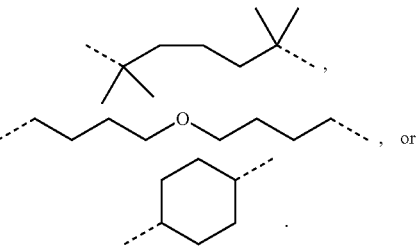, or

10. The compound, the pharmaceutically acceptable salt or tautomer thereof according to claim 1, wherein $R_{23}$ is

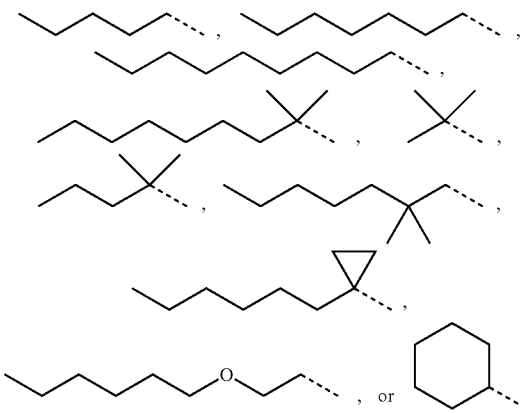, or

11. The compound, the pharmaceutically acceptable salt or tautomer thereof according to claim 1, which is selected from the group consisting of

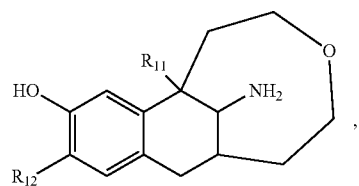

I-2

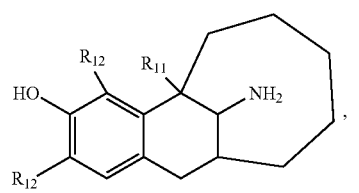

I-4

-continued
I-5
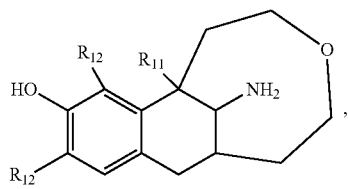
I-6
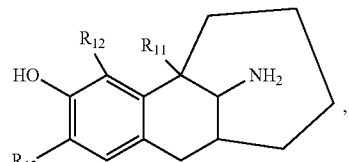
I-7
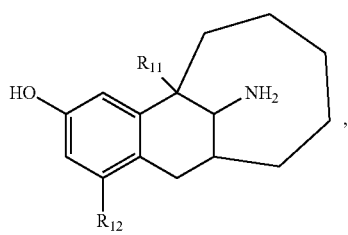
I-8
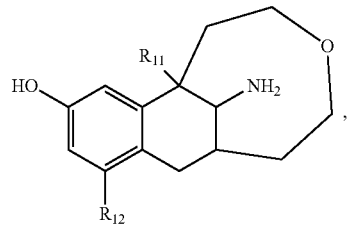
I-9
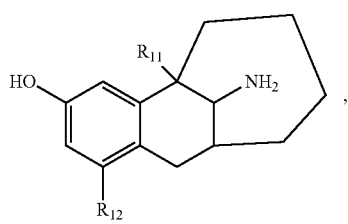
II-1
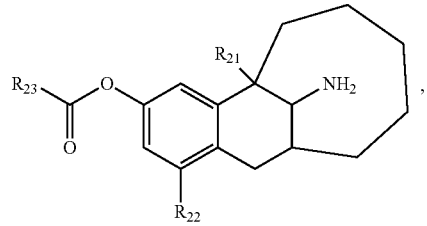
II-2
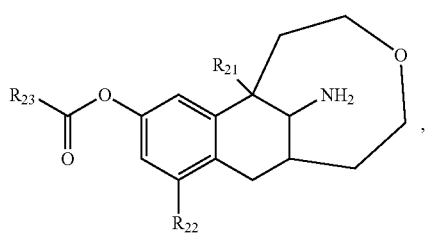
II-3
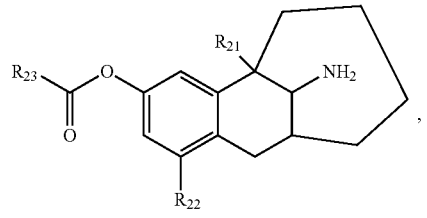
III-1
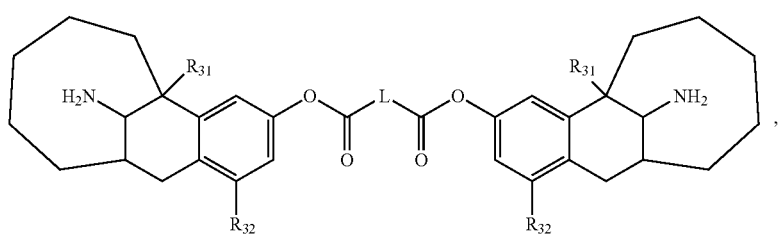
III-2
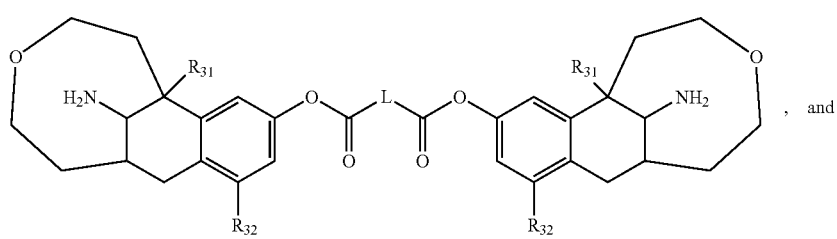
, and
III-3
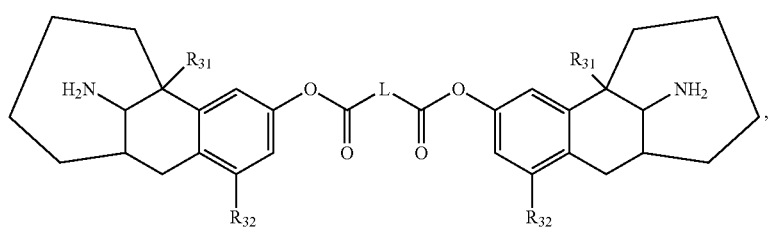
, wherein, L, $R_{11}$, $R_{12}$, $R_{21}$, $R_{22}$, $R_{23}$, $R_{31}$ and $R_{32}$ are defined as in claim 1.
12. A compound selected from the group consisting of
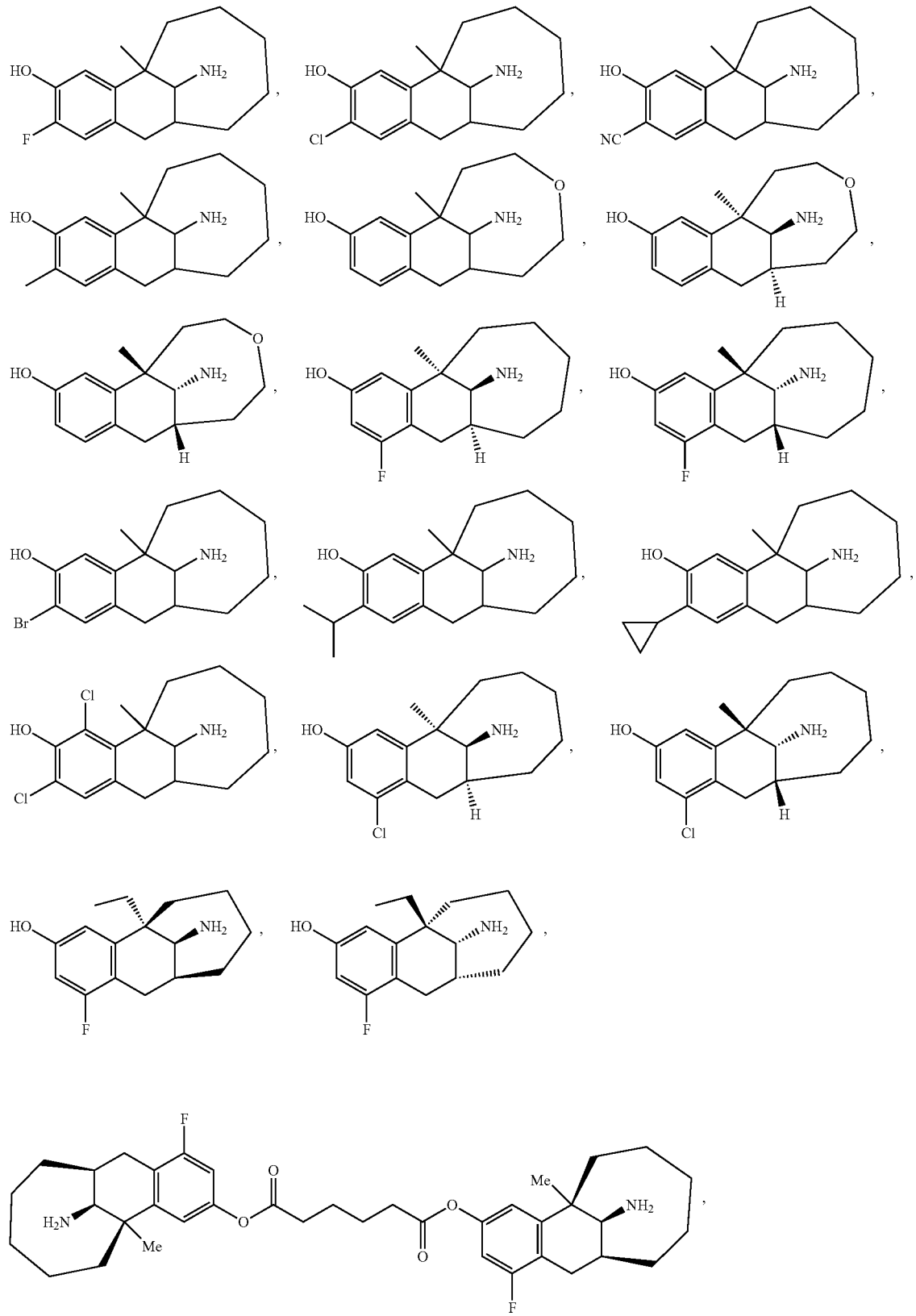

-continued
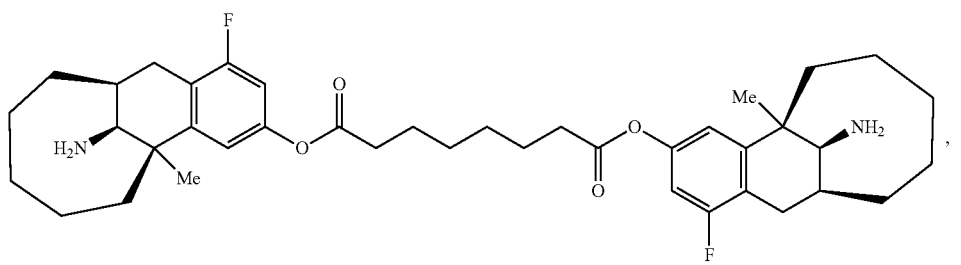
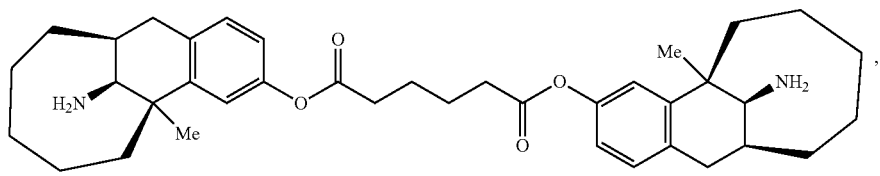
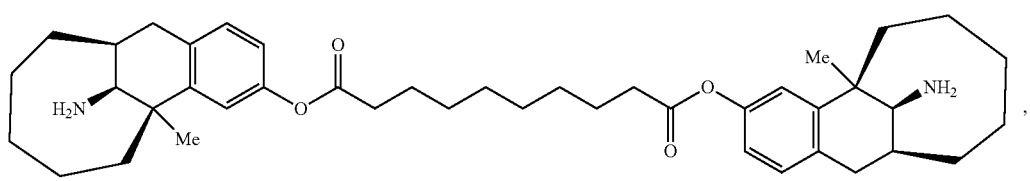
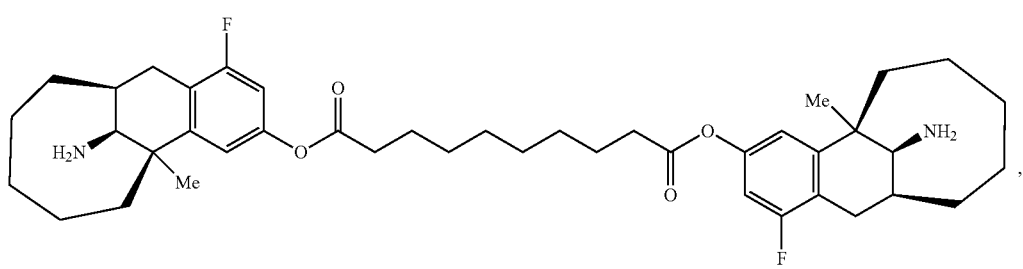
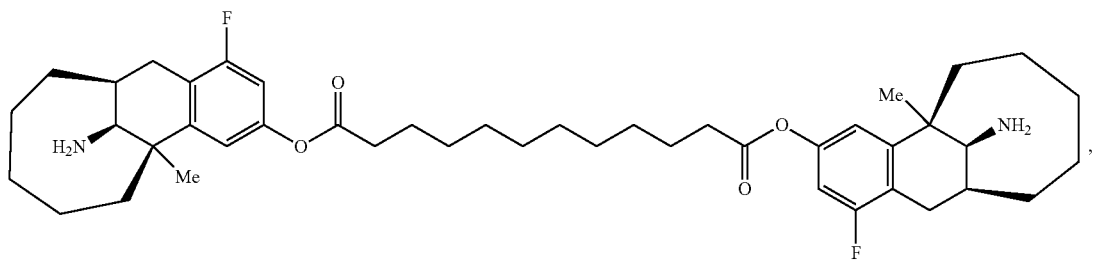
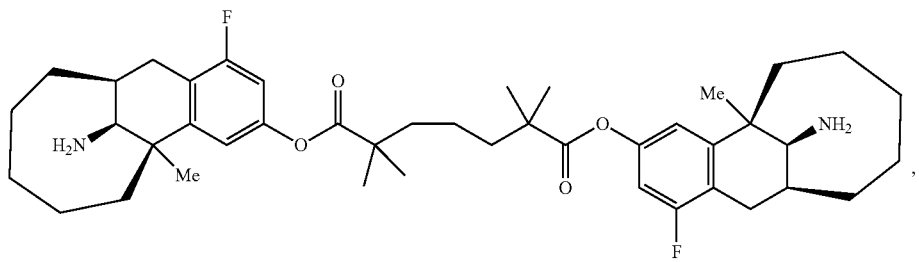
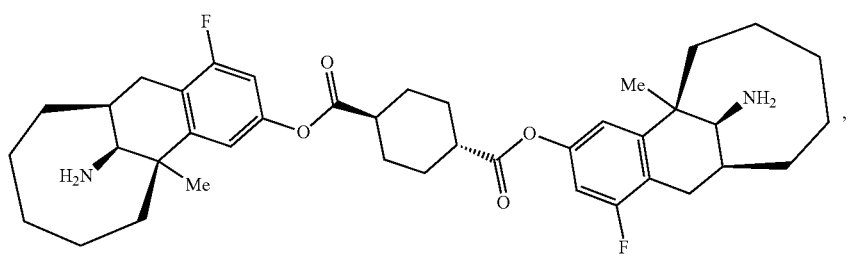

117 118
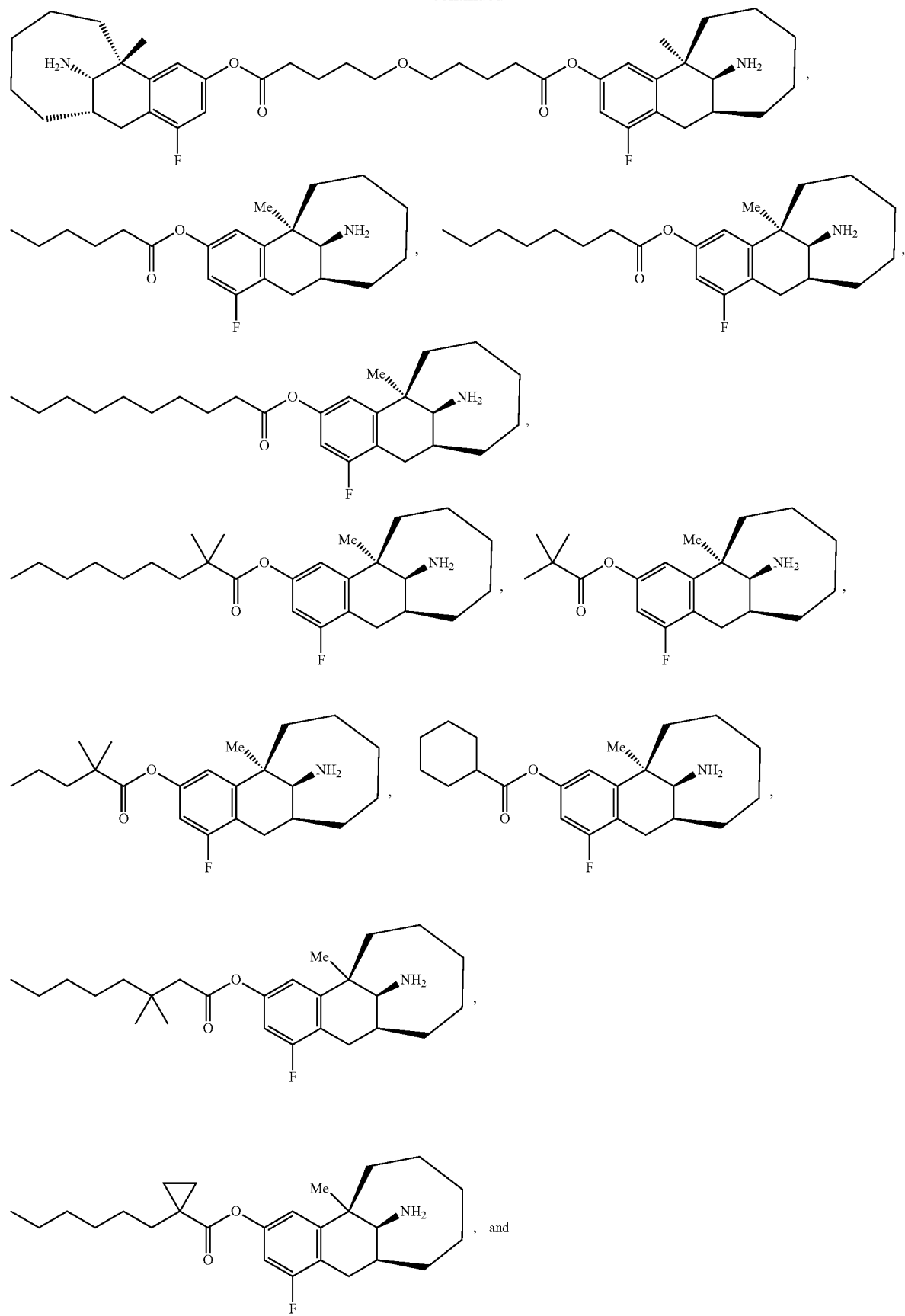
-continued

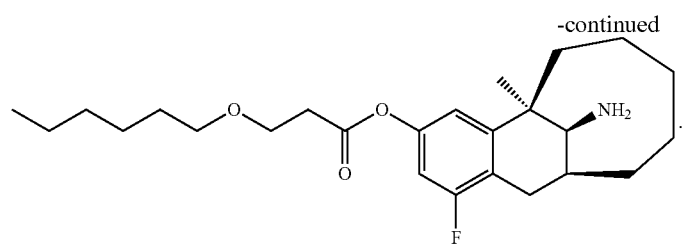
13. A compound selected from the group consisting of
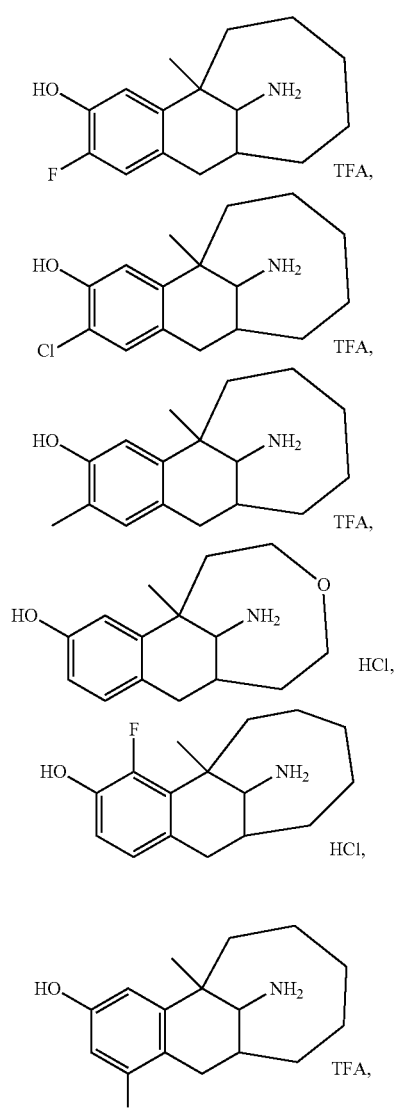
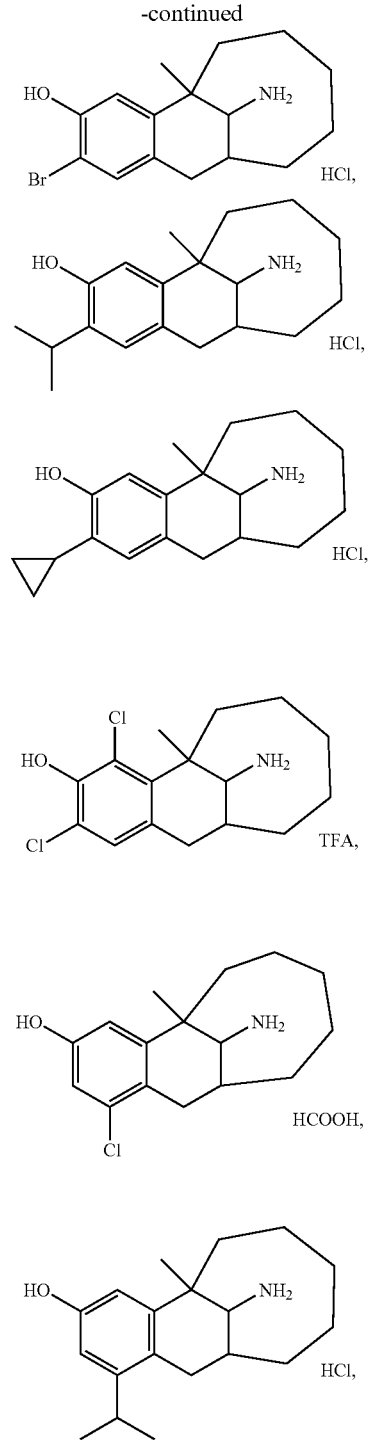

-continued
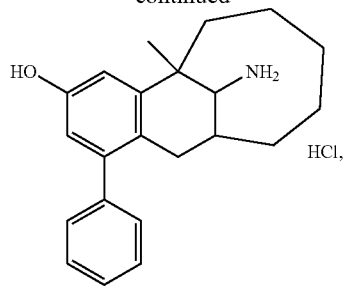 HCl,
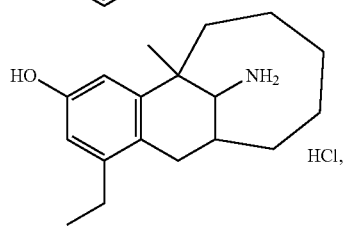 HCl,
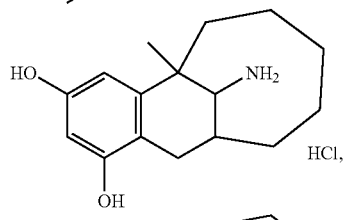 HCl,
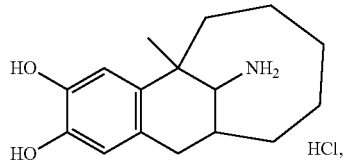 HCl,
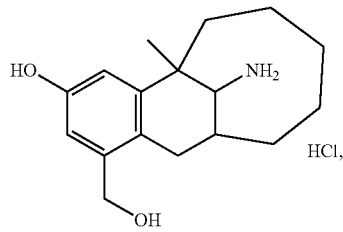 HCl,
-continued
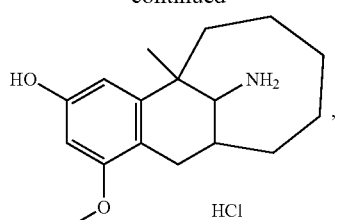 HCl,
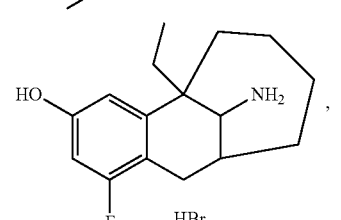 HBr,
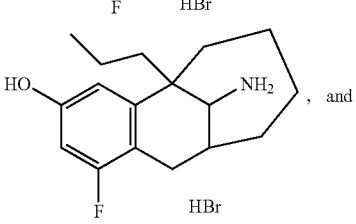 HBr, and
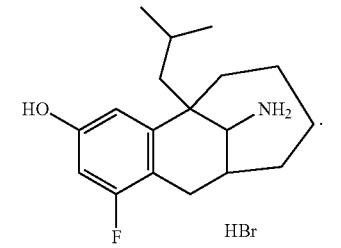 HBr.
14. A method for treating pain in a subject in need thereof, comprising: administering an effective amount of the compound, the pharmaceutically acceptable salt or tautomer thereof according to claim 1 to the subject.
* * * * *